(12) United States Patent
Sasisekharan et al.

(10) Patent No.: US 7,504,247 B2
(45) Date of Patent: *Mar. 17, 2009

(54) 2-O SULFATASE COMPOSITIONS AND METHODS OF DEGRADATION THEREWITH

(75) Inventors: Ram Sasisekharan, Bedford, MA (US); James Myette, Belmont, MA (US); Zachary Shriver, Boston, MA (US); Ganesh Venkataraman, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/433,340

(22) Filed: May 11, 2006

(65) Prior Publication Data

US 2006/0292673 A1 Dec. 28, 2006

Related U.S. Application Data

(62) Division of application No. 10/753,761, filed on Jan. 7, 2004, now Pat. No. 7,270,815.

(60) Provisional application No. 60/438,810, filed on Jan. 8, 2003.

(30) Foreign Application Priority Data

Jul. 7, 2003 (JP) ............................. 2003-271653

(51) Int. Cl.
*C12N 9/16* (2006.01)
(52) U.S. Cl. ................. 435/196; 435/252.3; 435/320.1; 536/23.2
(58) Field of Classification Search ................. 435/196, 435/252.3, 320.1; 536/23.2
See application file for complete search history.

(56) References Cited

U.S. PATENT DOCUMENTS

| | | | |
|---|---|---|---|
| 5,198,355 | A | 3/1993 | Kikuchi et al. |
| 5,254,801 | A | 10/1993 | Dotson et al. |
| 5,798,239 | A | 8/1998 | Wilson et al. |
| 5,932,211 | A | 8/1999 | Wilson et al. |
| 6,153,188 | A | 11/2000 | Wilson et al. |
| 6,217,863 | B1 | 4/2001 | Godavarti et al. |
| 6,597,996 | B1 | 7/2003 | Venkataraman et al. |
| 6,869,789 | B2 | 3/2005 | Liu et al. |
| 6,962,699 | B2 | 11/2005 | Pojasek et al. |
| 7,056,504 | B1 | 6/2006 | Sasisekharan et al. |
| 7,083,937 | B2 | 8/2006 | Sasisekharan et al. |
| 7,105,334 | B2 | 9/2006 | Pojasek et al. |
| 7,110,889 | B2 | 9/2006 | Venkataraman et al. |
| 7,117,100 | B2 | 10/2006 | Venkataraman et al. |
| 7,129,335 | B2 | 10/2006 | Pojasek et al. |
| 7,139,666 | B2 | 11/2006 | Venkataraman et al. |
| 7,150,981 | B2 | 12/2006 | Habuchi et al. |
| 7,247,445 | B2 | 7/2007 | Sasisekharan et al. |
| 7,270,815 | B2 | 9/2007 | Sasisekharan et al. |
| 2002/0128225 | A1 | 9/2002 | Liu et al. |
| 2003/0008820 | A1 | 1/2003 | Kwan et al. |
| 2003/0099628 | A1 | 5/2003 | Liu et al. |
| 2003/0147875 | A1* | 8/2003 | Rosen et al. ................ 424/94.6 |
| 2003/0191587 | A1 | 10/2003 | Venkataraman et al. |
| 2004/0091471 | A1 | 5/2004 | Myette et al. |
| 2004/0092037 | A1 | 5/2004 | Sasisekharan et al. |
| 2005/0037376 | A1 | 2/2005 | Sasisekharan et al. |
| 2005/0214276 | A9 | 9/2005 | Myette et al. |
| 2005/0227320 | A1 | 10/2005 | Pojasek et al. |
| 2005/0233402 | A1 | 10/2005 | Liu et al. |
| 2006/0024664 | A1 | 2/2006 | Sasisekharan et al. |
| 2006/0057638 | A1 | 3/2006 | Bosques et al. |
| 2006/0067927 | A1 | 3/2006 | Chandrasekaran et al. |
| 2006/0067928 | A1 | 3/2006 | Liu et al. |
| 2006/0078959 | A1 | 4/2006 | Prabhakar et al. |
| 2006/0083711 | A1 | 4/2006 | Berry et al. |
| 2006/0105430 | A1 | 5/2006 | Sasisekharan et al. |

(Continued)

FOREIGN PATENT DOCUMENTS

EP 0355831 2/1990

(Continued)

OTHER PUBLICATIONS

Boltes et al., 1.3 A structure of arylsulfatase from Pseudomonas aeruginosa establishes the catalytic mechanism of sulfate ester cleavage in the sulfatase family. Structure. Jun. 2001;9(6):483-91.
Bond et al., Structure of a human lysosomal sulfatase. Structure. Feb. 15, 1997;5(2):277-89.
Cohlberg et al., Heparin and other glycosaminoglycans stimulate the formation of amyloid fibrils from alpha-synuclein in vitro. Biochemistry. Feb. 5, 2002;41(5):1502-11.
Folkman et al., Control of angiogenesis by heparin and other sulfated polysaccharides. Adv Exp Med Biol. 1992;313:355-64.
Higgins et al., Using Clustal for multiple sequence alignments. Methods Enzymol. 1996;266:383-402.

(Continued)

*Primary Examiner*—Tekchand Saidha
(74) *Attorney, Agent, or Firm*—Wolf, Greenfield & Sacks, P.C.

(57) ABSTRACT

The invention relates to 2-O sulfatase and uses thereof. In particular, the invention relates to recombinantly produced 2-O sulfatase, functional variants and nucleic acid molecules that encode these molecules. The invention also provides methods of using 2-O sulfatase for a variety of purposes, including degrading and analyzing glycosaminoglycans (GAGs) present in a sample. For instance, 2-O sulfatase may be used for determining the purity, identity, composition and sequence of glycosaminoglycans present in a sample. The invention also relates to methods of inhibiting angiogenesis and cellular proliferation as well as methods for treating cancer, neurodegenerative disease, atherosclerosis and microbial infection using 2-O sulfatase and/or GAG fragments produced by degradation with 2-O sulfatase.

32 Claims, 20 Drawing Sheets

U.S. PATENT DOCUMENTS

| | | | |
|---|---|---|---|
| 2006/0127950 | A1 | 6/2006 | Bosques et al. |
| 2006/0154894 | A1 | 7/2006 | Berry et al. |
| 2006/0177885 | A1 | 8/2006 | Myette et al. |
| 2006/0177910 | A1 | 8/2006 | Myette et al. |
| 2006/0177911 | A1 | 8/2006 | Myette et al. |
| 2006/0182734 | A1 | 8/2006 | Liu et al. |
| 2006/0183713 | A1 | 8/2006 | Liu et al. |
| 2006/0183891 | A1 | 8/2006 | Myette et al. |
| 2006/0292130 | A1 | 12/2006 | Sasisekharan et al. |
| 2006/0292655 | A1 | 12/2006 | Sasisekharan et al. |
| 2006/0292673 | A1 | 12/2006 | Sasisekharan et al. |
| 2007/0004012 | A1 | 1/2007 | Sasisekharan et al. |
| 2007/0020243 | A1 | 1/2007 | Sengupta et al. |
| 2007/0065424 | A1 | 3/2007 | Pojasek et al. |
| 2007/0065921 | A1 | 3/2007 | Sasisekharan et al. |
| 2007/0066769 | A1 | 3/2007 | Venkataraman et al. |
| 2007/0072268 | A1 | 3/2007 | Habuchi et al. |
| 2007/0148157 | A1 | 6/2007 | Prabhakar et al. |
| 2007/0148158 | A1 | 6/2007 | Sasisekharan et al. |
| 2007/0148740 | A1 | 6/2007 | Prabhakar et al. |
| 2007/0161073 | A1 | 7/2007 | Sasisekharen et al. |
| 2007/0202563 | A1 | 8/2007 | Prabhakar et al. |
| 2007/0224670 | A1 | 9/2007 | Prabhakar et al. |

FOREIGN PATENT DOCUMENTS

| | | |
|---|---|---|
| EP | 0423818 A1 | 4/1991 |
| JP | 69006619 B | 12/1965 |
| WO | WO-9716556 A1 | 5/1997 |
| WO | WO-0026393 A1 | 5/2000 |
| WO | WO-0121640 A1 | 3/2001 |
| WO | WO-0218539 A2 | 3/2002 |
| WO | WO 2002/059327 A2 | 8/2002 |
| WO | WO 2004/031365 A2 | 4/2004 |
| WO | WO 2005/017118 A2 | 2/2005 |
| WO | WO-2006089206 A2 | 8/2006 |
| WO | WO 2007/044471 A2 | 4/2007 |

OTHER PUBLICATIONS

Ishikawa et al., Inhibition of glomerular cell apoptosis by heparin. Kidney Int. Sep. 1999;56(3):954-63.

Liu et al., Cell surface heparan sulfate and its roles in assisting viral infections. Med Res Rev. Jan. 2002;22(1):1-25.

Lukatela et al., Crystal structure of human arylsulfatase A: the aldehyde function and the metal ion at the active site suggest a novel mechanism for sulfate ester hydrolysis. Biochemistry. Mar. 17, 1998;37(11):3654-64.

Nielsen et al., Identification of prokaryotic and eukaryotic signal peptides and prediction of their cleavage sites. Protein Eng. Jan. 1997;10(1):1-6.

Perrimon et al., Specificities of heparan sulphate proteoglycans in developmental processes. Nature. Apr. 13, 2000;404(6779):725-8.

Sehayek et al., Binding to heparan sulfate is a major event during catabolism of lipoprotein lipase by HepG2 and other cell cultures. Atherosclerosis. Apr. 7, 1995;114(1):1-8.

Vlodavsky et al., Mammalian heparanase as mediator of tumor metastasis and angiogenesis. Isr Med Assoc J. Jul. 2000;2 Suppl:37-45.

Von Bulow et al., Crystal structure of an enzyme-substrate complex provides insight into the interaction between human arylsulfatase A and its substrates during catalysis. J Mol Biol. Jan. 12, 2001;305(2):269-77.

Genbank Submission; NIH/NCBI, Accession No. AAG05721.1, AE004659_7; Stover et al.; Jul. 7, 2006.

Genbank Submission; NIH/NCBI, Accession No. AL355753; Redenbach et al.; May 12, 2002.

Genbank Submission; NIH/NCBI, Accession No. BAB38042.1; Makino et al.; May 26, 2006.

Genbank Submission; NIH/NCBI, Accession No. AAF72520.1, AF248951_1; Wright et al.; May 29, 2000.

Genbank Submission; NIH/NCBI, Accession No. AAL45442.1; Wood et al.; May 28, 2004.

Genbank Submission; NIH/NCBI, Accession No. AAL18999.1; McClelland et al.; Aug. 9, 2005.

Genbank Submission; NIH/NCBI, Accession No. CAA51272.1; Modaressi et al.; Jun. 25, 1997.

Genbank Submission; NIH/NCBI, Accession No. AAA51784.1; Peters et al.; Oct. 31, 1994.

Genbank Submission; NIH/NCBI, Accession No. AAB03341.1; Loftus et al.; Feb. 3, 2000.

Genbank Submission; NIH/NCBI, Accession No. AAG03573.1, AE004456_4; Stover et al.; Jul. 7, 2006.

Genbank Submission; NIH/NCBI, Accession No. CAA88421.2; Beil et al.; Jun. 30, 2006.

Genbank Submission; NIH/NCBI, Accession No. NP_248873.1; Stover et al.; Aug. 3, 2006.

Genbank Submission; NIH/NCBI, Accession No. P51691; Beil et al.; Sep. 19, 2006.

Genbank Submission; NIH/NCBI, Accession No. AAC51350.1; Morris et al.; Oct. 11, 2005.

Genbank Submission; NIH/NCBI, Accession No. AAA63197.1; Wilson et al.; Mar. 7, 1995.

Genbank Submission; NIH/NCBI, Accession No. AA605721; Ekker et el.; Sep. 29, 1997.

Genbank Submission; NIH/NCBI, Accession No. BAB79937; Shimizu et al.; Oct. 21, 2004.

Genbank Submission; NIH/NCBI, Accession No. AAF72520; Wright et al.; May 29, 2000.

Genbank Submission; NIH/NCBI, Accession No. AAL45441; Wood et al.; May 28, 2004.

Genbank Submission; NIH/NCBI, Accession No. AAL19003; McClelland et al.; Aug. 9, 2005.

[No Author Listed] Iduronate-2-sulfatase. Glyko Catalogue No. GAG-5009. Revised Sep. 2000.

Berteau et al.; A new type of bacterial sulfatase reveals a novel maturation pathway in prokaryotes. J Biol Chem. Aug. 11, 2006;281(32):22464-70.

Bielicki et al., Human liver iduronate-2-sulphatase. Purification, characterization and catalytic properties. Biochem J. Oct. 1, 1990;271(1):75-86.

Boltes et al., 1.3 A structure of arylsulfatase from Pseudomonas aeruginosa establishes the catalytic mechanism of sulfate ester cleavage in the sulfatase family. Structure. Jun. 2001;9(6):483-91. Abstract Only.

Bond et al., Structure of a human lysosomal sulfatase. Structure. Feb. 15, 1997;5(2):277-89. Abstract Only.

Bruce et al., Flavobacterium heparinum 6-O-sulphatase for N-substituted glucosamine 6-O-sulphate. Eur J Biochem. Oct. 1, 1985;152(1):75-82.

Bruce et al., Flavobacterium heparinum sulphamidase for D-glucosamine sulphamate. Purification and characterisation. Eur J Biochem. Jun. 15, 1987;165(3):633-8.

Cohlberg et al., Heparin and other glycosaminoglycans stimulate the formation of amyloid fibrils from alpha-synuclein in vitro. Biochemistry. Feb. 5, 2002;41(5):1502-11. Abstract Only.

Dietrich et al., Enzymic degradation of heparin. A sulphamidase and a sulphoesterase from Flavobacterium heparinum. Biochem J. Jan. 1969;111(1):91-5.

Dietrich et al., Sequential degradation of heparin in Flavobacterium heparinum. Purification and properties of five enzymes involved in heparin degradation. J Biol Chem. Sep. 25, 1973;248(18):6408-15.

Ernst et al., Enzymatic degradation of glycosaminoglycans. Crit Rev Biochem Mol Biol. 1995;30(5):387-444.

Ernst et al., Expression in *Escherichia coli*, purification and characterization of heparinase I from Flavobacterium heparinum. Biochem J. Apr. 15, 1996;315( Pt 2):589-97.

Esko et al., Molecular diversity of heparan sulfate. J Clin Invest. Jul. 2001;108(2):169-73.

Folkman et al., Control of angiogenesis by heparin and other sulfated polysaccharides. Adv Exp Med Biol. 1992;313:355-64. Abstract Only.

Freeman et al., Human liver glucuronate 2-sulphatase. Purification, characterization and catalytic properties. Biochem J. Apr. 1, 1989;259(1):209-16.

Higgins et al., Using Clustal for multiple sequence alignments. Methods Enzymol. 1996;266:383-402. Abstract Only.

Homans et al., A molecular mechanical force field for the conformational analysis of oligosaccharides: comparison of theoretical and crystal structures of Man alpha 1-3Man beta 1-4GlcNAc. Biochemistry. Oct. 2, 1990;29(39):9110-8.

Huige et al., Force field parameters for sulfates and sulfamates bases on Ab Initio calculations: Extensions of Amber and CHARMm fields. J Comp Chem. 1995;16(1):56-79.

Ishikawa et al., Inhibition of glomerular cell apoptosis by heparin. Kidney Int. Sep. 1999;56(3):954-63. Abstract Only.

Jandik et al., Action pattern of polysaccharide lyases on glycosaminoglycans. Glycobiology. Jun. 1994;4(3):289-96. Abstract Only.

Kapila et al., The heparin-binding domain and V region of fibronectin regulate apoptosis by suppression of p53 and c-myc in human primary cells. J Biol Chem. Mar. 8, 2002;277(10):8482-91.

Kertesz et al., Riding the sulfur cycle-metabolism of sulfonates and sulfate esters in gram-negative bacteria. FEMS Microbiol Rev. Apr. 2000;24(2):135-75. Abstract Only.

Law et al., Studies on the particle-bound carbohydrate sulphoamide sulphohydrolase and carbohydrate sulphate sulphohydrolase of flavobacterium heparinum. Proceedings of the Biochemical Society. 1969;115:10P.

Lindahl et al., Regulated diversity of heparan sulfate. J Biol Chem. Sep. 25, 1998;273(39):24979-82.

Liu et al., Heparan sulfate D-glucosaminyl 3-O-sulfotransferase-3A sulfates N-unsubstituted glucosamine residues. J Biol Chem. Dec. 31, 1999;274(53):38155-62.

Liu et al., Cell surface heparan sulfate and its roles in assisting viral infections. Med Res Rev. Jan. 2002;22(1):1-25. Abstract Only.

Lukatela et al., Crystal structure of human arylsulfatase A: the aldehyde function and the metal ion at the active site suggest a novel mechanism for sulfate ester hydrolysis. Biochemistry. Mar. 17, 1998;37(11):3654-64. Abstract Only.

Lyon et al., Bio-specific sequences and domains in heparan sulphate and the regulation of cell growth and adhesion. Matrix Biol. Nov. 1998;17(7):485-93.

McLean et al., Enzymic removal of 2-O-sulphato-?4,5-glycuronic acid residues from heparin oligosaccharides. Proceedings of the 7th International Symposium of Glycoconjugates. Lund, Sweden. 1983;68-9.

McLean et al., Flavobacterium heparinum 2-O-sulphatase for 2-O-sulphato-delta 4,5-glycuronate-terminated oligosaccharides from heparin. Eur J Biochem. Dec. 17, 1984;145(3):607-15.

Morimoto-Tomita et al., Cloning and characterization of two extracellular heparin-degrading endosulfatases in mice and humans. J Biol Chem. Dec. 20, 2002;277(51):49175-85.

Myette et al., Expression in *Escherichia coli*, purification and kinetic characterization of human heparan sulfate 3-O-sulfotransferase-1. Biochem Biophys Res Commun. Feb. 1, 2002;290(4):1206-13.

Myette et al., The heparin/heparan sulfate 2-O-sulfatase from Flavobacterium heparinum. Molecular cloning, recombinant expression, and biochemical characterization. J Biol Chem. Apr. 4, 2003;278(14):12157-66. Epub Jan. 7, 2003.

Myette et al., Molecular cloning of the heparin/heparan sulfate delta 4,5 unsaturated glycuronidase from Flavobacterium heparinum, its recombinant expression in *Escherichia coli*, and biochemical determination of its unique substrate specificity. Biochemistry. Jun. 11, 2002;41(23):7424-34.

Nielsen et al., Identification of prokaryotic and eukaryotic signal peptides and prediction of their cleavage sites. Protein Eng. Jan. 1997;10(1):1-6. Abstract Only.

Parenti et al., The sulfatase gene family. Curr Opin Genet Dev. Jun. 1997;7(3):386-91.

Perrimon et al., Specificities of heparan sulphate proteoglycans in developmental processes. Nature. Apr. 13, 2000;404(6779):725-8. Abstract Only.

Raman et al., The heparin/heparan sulfate 2-O-sulfatase from Flavobacterium heparinum. A structural and biochemical study of the enzyme active site and saccharide substrate specificity. J Biol Chem. Apr. 4, 2003;278(14):12167-74. Epub Jan. 7, 2003.

Raman et al., Identification of structural motifs and amino acids within the structure of human heparan sulfate 3-O-sulfotransferase that mediate enzymatic function. Biochem Biophys Res Commun. Feb. 1, 2002;290(4):1214-9.

Rhomberg et al., Mass spectrometric and capillary electrophoretic investigation of the enzymatic degradation of heparin-like glycosaminoglycans. Proc Natl Acad Sci U S A. Apr. 14, 1998;95(8):4176-81.

Sasisekharan et al., Roles of heparan-sulphate glycosaminoglycans in cancer. Nat Rev Cancer. Jul. 2002;2(7):521-8.

Sasisekharan et al., Cloning and expression of heparinase I gene from Flavobacterium heparinum. Proc Natl Acad Sci U S A. Apr. 15, 1993;90(8):3660-4.

Sehayek et al., Binding to heparan sulfate is a major event during catabolism of lipoprotein lipase by HepG2 and other cell cultures. Atherosclerosis. Apr. 7, 1995;114(1):1-8. Abstract Only.

Selva et al., Role of heparan sulfate proteoglycans in cell signaling and cancer. Adv Cancer Res. 2001;83:67-80.

Shaklee et al., A sulfatase specific for glucuronic acid 2-sulfate residues in glycosaminoglycans. J Biol Chem. Aug. 5, 1985;260(16):9146-9.

Shriver et al., Emerging views of heparan sulfate glycosaminoglycan structure/activity relationships modulating dynamic biological functions. Trends Cardiovasc Med. Feb. 2002;12(2):71-7.

Simeon et al., Expression of glycosaminoglycans and small proteoglycans in wounds: modulation by the tripeptide-copper complex glycyl-L-histidyl-L-lysine-Cu(2+). J Invest Dermatol. Dec. 2000;115(6):962-8.

Sugahara et al., Specificity studies of bacterial sulfatases by means of structurally defined sulfated oligosaccharides isolated from shark cartilage chondroitin sulfate D. Eur J Biochem. Aug. 1, 1996;239(3):865-70. Abstract Only.

Toida et al., Enzymatic preparation of heparin oligosaccharides containing antithrombin III binding sites. J Biol Chem. Dec. 13, 1996;271(50):32040-7.

Tumova et al., Heparan sulfate proteoglycans on the cell surface: versatile coordinators of cellular functions. Int J Biochem Cell Biol. Mar. 2000;32(3):269-88.

Venkataraman et al., Sequencing complex polysaccharides. Science. Oct. 15, 1999;286(5439):537-42.

Vlodavsky et al., Mammalian heparanase as mediator of tumor metastasis and angiogenesis. Isr Med Assoc J. Jul. 2000;2 Suppl:37-45. Abstract Only.

Von Bulow et al., Crystal structure of an enzyme-substrate complex provides insight into the interaction between human arylsulfatase A and its substrates during catalysis. J Mol Biol. Jan. 12, 2001;305(2):269-77. Abstract Only.

Von Figura et al., A novel protein modification generating an aldehyde group in sulfatases: its role in catalysis and disease. Bioessays. Jun. 1998;20(6):505-10. Abstract Only.

Waldow et al., Amino acid residues forming the active site of arylsulfatase A. Role in catalytic activity and substrate binding. J Biol Chem. Apr. 30, 1999;274(18):12284-8.

Warnick et al., Purification of an unusual -glycuronidase from flavobacteria. Biochemistry. Feb. 15, 1972;11(4):568-72.

Zhang et al., 6-O-sulfotransferase-1 represents a critical enzyme in the anticoagulant heparan sulfate biosynthetic pathway. J Biol Chem. Nov. 9, 2001;276(45):42311-21.

Desai et al., Specificity studies on the heparin lyases from Flavobacterium heparinum. Biochemistry. Aug. 17, 1993;32(32):8140-5.

Dietrich et al., Enzymic degradation of heparin. A glucosaminidase and a glycuronidase from Flavobacterium heparinum. Biochemistry. May 1969;8(5):2089-94.

Feingold et al., Conformational aspects of the reaction mechanisms of polysaccharide lyases and epimerases. FEBS Lett. Nov. 2, 1987;223(2):207-11.

Gacesa, Alginate-modifying enzymes: a proposed unified mechanism of action for the lyases and epimerases. FEBS Letters. 1987;212(2):199-202.

Gu et al., Purification, characterization and specificity of chondroitin lyases and glycuronidase from Flavobacterium heparinum. Biochem J. Dec. 1, 1995;312 ( Pt 2):569-77.

Hovingh et al., Specificity of flavobacterial glycuronidases acting on disaccharides derived from glycosaminoglycans. Biochem J. Aug. 1, 1977;165(2):287-93.

Linhardt et al., Examination of the substrate specificity of heparin and heparan sulfate lyases. Biochemistry. Mar. 13, 1990;29(10):2611-17.

Linhardt et al., Polysaccharide lyases. Appl Biochem Biotechnol. Apr. 1986;12(2):135-76.

Linker et al., The enzymatic degradation of heparin and heparitin sulfate. I. The fractionation of a crude heparinase from flavobacteria. J Biol Chem. Oct. 1965;240(10):3724-8.

Lohse et al., Purification and characterization of heparin lyases from Flavobacterium heparinum. J Biol Chem. Dec. 5, 1992;267(34):24347-55.

Vlodavsky et al., Mammalian heparanase: gene cloning, expression and function in tumor progression and metastasis. Nat Med. Jul. 1999;5(7):793-802.

Wishart et al., A single mutation converts a novel phosphotyrosine binding domain into a dual-specificity phosphatase. J Biol Chem. Nov. 10, 1995;270(45):26782-5.

Witkowski et al., Conversion of a beta-ketoacyl synthase to a malonyl decarboxylase by replacement of the active-site cysteine with glutamine. Biochemistry. Sep. 7, 1999;38(36):11643-50.

Wright et al., Cloning of a mucin-desulfating sulfatase gene from Prevotella strain RS2 and its expression using a Bacteroides recombinant system. J Bacteriol. Jun. 2000;182(11):3002-7.

Yang et al., Purification and characterization of heparinase from Flavobacterium heparinum. J Biol Chem. Feb. 10, 1985;260(3):1849-57.

* cited by examiner

```
                   1                  10                  20      ↓
                   S K H N M K M Y K S K G W L I A M L I L A G F G D A G A Q T
  1   agtaaacataacatgaagatgtacaaatcgaaaggctggttgatagccatgcttatacttgcaggttttggagatgcagggggcgcaaacc 90
                         30                40                50
                   S K V A A S R P N I I I I M T D Q Q T A D A M S N A G N K D
 91   tcaaaagtagcagcttccaggcctaacatcattatcatcatgacagatcagcaaacagctgatgccatgagcaatgctggtaataaggac 180
                         60                70                80  ★
                   L H T P A M D V L A A N G T R F T R A Y C A Q P L C T P S R
181   ctgcatacacctgcaatggatgttttggctgcaaacggtacccgttttacacgtgcctattgtgcccagccgctctgtacaccttcacgc 270
                         90               100               110
                   S A I F S G K M P H E T G F T G N T P E K D G Q W P D S V L
271   tccgcgatatttagcggaaaaatgccacatgaaaccggctttacggggaatacaccggaaaaggacggacagtggcccgattctgtgctg 360
                        120               130               140
                   M M G K I F K A G G Y K T G Y V G K W H L P V P V T K V A Q
361   atgatgggcaaaatatttaaggcaggaggctataaaaccggctacgtcggaaaatggcacctgcctgttcctgttactaaagtagcacaa 450
                        150               160               170
                   H G F E T I E N T G M G D Y T D A V T P S Q C A N F N K K N
                   →
451   catggatttgagactattgagaatacaggtatgggcgattataccgatgcagttaccccatcgcaatgcgccaacttcaataaaaagaat 540
                        180               190               200
                   K D N P F L L V A S F L N P H D I C E W A R G D N L K M D V
541   aaagacaacccatttttactggtagcatcctttttgaacccacacgatatttgtgaatgggcaagggtgataatttgaaaatggatgtt 630
                        210               220               230
                   L D A A P D T A F C P K L P A N W P I P A F E P A I V R E Q
631   ctggatgcagcgccggatacagcattttgtccgaaattacctgccaactggccaattccggcttttgagcctgccattgtaagggaacag 720
                        240               250               260
                   Q K V N P R T Y P S V G W N E S Q W R K Y R W A Y N R L V E
721   caaaaggtgaacccgcgtacttatccttcggtaggctggaacgaaagccagtggcgcaaataccgctgggcctataaccgcctggtagag 810
                        270               280               290
                   K V D N Y M A M V L G S L K K Y G I E D N T I I I F T S D H
810   aaggtagacaattatatggccatggtattgggttcgttaaaaaaatatggtatagaagacaataccatcatcatctttaccagcgatcat 900
                        300               310               320
                   G D G Y A A H E W N Q K Q I L Y E E A A R I P F I I S K I G
910   ggtgatggttatgcggcacatgagtggaaccagaagcagattttgtatgaggaggctgccaggataccttttatcatctcgaagatcgga 990
                        330               340               350
                   Q W K A R T D D Q L V C N G I D I I P T I C G F A G I A K P
                                                                           ←
991   caatggaaagccagaaccgatgatcagctggtttgcaatggcatcgatattatccccacatatgtggctttgccggaattgctaaacct 1080
                        360               370               380
                   V G L K G L D L S K R I A N P S V K L R D T L V I E T D F A
1081  gttggtttaaaaggcctggatttaagtaaacgtattgccaaccccttcggttaaactacgggatactttagtgatagaaaccgattttgct 1170
                        390               400               410
                   D N E L L L G I K G R A V I T K D F K Y I V Y D K G E I R E
1171  gataacgaactgttgctgggtattaagggcagggcagtgattaccaaagattttaaatacattgtttatgacaaggggggagatccgggaa 1260
                        420               430               440
                   Q L F D L E K D A G E M D N L A V K P A Y K K K L N E M R A
1261  caattgtttgacctggaaaaagacgcaggagaaatggataacctggctgttaaaccgcctataaaaagaaattgaatgaaatgcgcgct 1350
                        450               460
                   Y L K L W C K Q H Q D S F Y A L K K stop
1351  tacctgaaactatggtgtaaacagcaccaggattcgttttatgcattaaaaaaataa
```

Fig. 2

```
                                 10              20              30              40              50
Flavobact. 2-O sulf   MKMYKSKGWIIAMLILAGFG-----------DAGAQTSKVAASRPNIHIIMTDQQTADAMSNA
Pseudomonas  sulf    ------------MSQPKP-------------------------IRNVLVIMCDQLRRDYLSCY
Streptomyces sulf    --MTRTNEPGAQPGPQAGAESGVQTGAESGAQACDQAGASRKNILFLMTDQHRTDTLGAY
E. coli O157:H7 sulf --MKRP---------------------------------------NLFIMTDTQAPNMVGCY
Prevotella AptA      --MKSDNMRFYSAMLMAGCG----------LHAAAQTQRPNIVFITDDHSFQTHSAY
Agrobact.    sulf    --MPRP------------------------------NILIHMADQFNGTFFPDG
Salmonella   sulf    -MKRTVVASMIGLALCAGCVLS--------TAQAATAKRPNLVIEADDLGYGDLATY
         consensus   ------------m--p--ag-------------------r--NilyimtDq-----l--y 60              70              80*             90              100
Flavobact. 2-O sulf  G---NKDLHTPAMDVLAANGTRDTRAYCAQPLCTDSRSAFSGKMPHELGFTGNTPEKDG
Pseudomonas  sulf    G---HPYLHTPNIDRLAEGMRLARAYTQGTLCGHMSSYTRYVSSHQVAWNAVP---
Streptomyces sulf    G---NPLAHTPALDELAATGTRDRWYTPTAICTARASLLTQAPFRHKELANHERNVG
E. coli O157:H7 sulf S---GKPLNTQNIDSLAEGHRENSAYTCSPVCTDARAGLFTCIYANQSGPWTNNVAP---
Prevotella AptA      GSEVSKLAPTPNIDRLANEGARLDDAEVENSLSTDARACLLTLYSHQNGQRTLGKG---
Agrobact.    sulf    P---ADFLHAPHEKALAERSVRDANTYTASPLCADARASFMSQLPSRDRVYDNAAEF---
Salmonella   sulf    G---HRIVKTPNIDKLAQEGVAKHTDYYAPAPLCSPSRAGLLTGRMPFFRLGIRSWIPEGKD
         consensus   g---k--lhtpnid-LAaegvrF----ayt--plctPaRa--lltg--p--sgv--n----

110             120             130             140
Flavobact. 2-O sulf  --QWPDSVLMMGKIFKAGYKTGYVGKWILPVP---------VTKVAQ
Pseudomonas  sulf    --LPEELTGGDYLRAAGLVGKTATANLEGMRRLGIDPASARGAALAEAGFEP
Streptomyces sulf    YLEDLAEDQFAFSRALREHCYNCGEFCGKWAGN---------RRTAADYG-------FDGPELP
E. coli O157:H7 sulf --GKNISTMGRYFKDAGYHTCYEGKWILDG---------HDY---------FGTGECP
Prevotella AptA      --IDSTKTFMSELLQDACYQTGVACKWIMQCRPKGFDFFRIFEGQGD-------YYNPLVL
Agrobact.    sulf    --ASDIPTYAHHLRAAGYYTGESGKMFVGP-----------DQLHGFE
Salmonella   sulf    --VAEGRNELTANLLKQQGYDTAMMGKLILNAG------------GDRTDQP
         consensus   --la----tlg--lr-aGy-tglvGkwHl-a--------------------p
```

Fig 3-1

```
                     150            160            170            180
Flavobact. 2-O sulf  HGFETIENTGMGDYTDAVTP--SQCANFNKKNKDNP-----------------------
  Pseudomonas sulf   YDRNDGVMPDDPAFADKRER--APYTHMLRRLGFTGDNPWHDWANAAAGADGEILSGWRM
   Streptomyces sulf GWHNPVDHPDYLAYLDERGL--PPYEISDRVRGTLPN----------------GGPGNLLAARLH
    E.coli O157:H7 sulf PEWDADYWFDGANYLSETTE--KEISLWRNGLNSMED----------------------LQANH
       Prevotella AptA SHDSNGKMEREQGYATDHVT--EHAVEFLNQRDEQKP-----FFLLVEHKAPHRTWMPNL
         Agrobact. sulf ERLTTDIMPADFGWTPDYTKPGERIDWMYHNLGSVTG------------------------A
        Salmonella sulf QAKDMGFDYTLVNPAGFVTDATLDNAKERPYGVVHP----------------------TGW
           consensus   ----------y----ay--elt-----y----g-l-----------------------

190            200            210            220            230            240
Flavobact. 2-O sulf  FLLVASFLNPHDICEWARGDNLKMDVLDAAPDTAFCPKLPANWPIPAFEPAIVREQQKVN
  Pseudomonas sulf   RHAGLPTRLPEAHSETAYTTRRAMDFIDEQGERPWCLHLSMIKPHWPMIAPAPYHALYRA
   Streptomyces sulf QPVEATFEHYLATRAIERLEHYAADAHDR--DRPFFLALHEFGPHLPYILPDEYFDLVDP
    E.coli O157:H7 sulf IDETFWAHRISNRAVDFLQQPAR-----AEEPFLMVMSYDEPHHPFTCPVEYLEKYAD
       Prevotella AptA KYLGLYDKVEFPLPTTFWDDYATRGTCASQQEMTIARHMQLAYDNKVEIDNAMRTRMLD
         Agrobact. sulf GVAEITNQMEYDDEVAYHATRKLYDLSRRLDDRPWCLTVSFTHPHDPVARRKFWDLYED
        Salmonella sulf IRNGQHIGRADKMSGEFVSSEVVNWLDNKKDDNPFFLYVAFTEVHSPLASPKKYLDMYSQ
           consensus   -----d------------d--pf-l-l-y--ph-py--p--y-dly--

250            260            270
Flavobact. 2-O sulf  PRTYPSVGWNES-----------QWRKKYRWAYNRLVEKVDNYMAMV
  Pseudomonas sulf   DQVLPALRAAPGEESDHPVYRAFREHRESLNFSRE-DVRRQVIPTMGLIRQVDQLGRE
   Streptomyces sulf ADVELPRSVSETTEGKPPVQRNYSAHWTFDTMPIE-TTR-KLIAVWGYVALTDRQIGRV
    E.coli O157:H7 sulf FYYELGEKAQDLANKPEHHRLWAQAMPS---PVG-DDGLYHPLYFACNDFVDDQLGRV
       Prevotella AptA RMDRLQKQAWDAMYS--PRNRAMLDAHLTDSALTV-WKYQRYMHDVLSTIHSVDESVGEI
         Agrobact. sulf CAALDPQSKAIAFEEQDPHSKRLLEACDHEAFEITGEQIRRARRGYFANISYIDEKIGEI
        Salmonella sulf YMTDYQKQHPDLTYG---------DWADKPWRGTGEVXANISYMDEQVGKV
           consensus   -----e--f----p--r------d----k-----Ywg-i--vDdqlgrv
```

Fig 3-2

```
                          280             290             300             310             320
Flavobact. 2-O sulf   EGSLKKYGIEDNLIHFFTSDHCDGYAAH------------EWNQK-QIEYEEAARLFL
   Pseudomonas sulf   FQHMRASGRWDDLETVFTSDHCDFEGDH------------GLGEK-EFELESAVGVLL
    Streptomyces sulf MAAMERLGLVDDLAVFFTCDHGEFTGSH------------RLHDKGPAMYEDIYRTGL
     E.coli O157:H7 sulf ENALKPE-QRENLWVALYTSDHCEMMGAH------------KLISKGAAMYDDITRLPLI
      Prevotella AptA YEYLKNHNLLDNLIDVYCSDQGFYMGEH------------GWFDKR-FMYEESLRTPLV
       Agrobact. sulf EDVLNATR-MEDIILFLSDHGDMLGER-------------GLWFK-MCFEEGSARVRLM
       Salmonella sulf LDKIKAMGEEDNLIVAFTSDNCPVTREARKVYELNLAGETDGLRGRKDNLWEGGIRVPAH
             consensus m--lk--g--dnTiivftsDhGd-lgdh------------gl--k---lyed--rvPll 330             340             350             360             370
Flavobact. 2-O sulf   ISKIG---QWKARTDDQLVCNGIDLLPTDCGFAGHAKP---VGLKGLDLSKREANPSVK
   Pseudomonas sulf   IRDPRPEADATRGRVEEALVQS-IDVLPSTEBAFAVEPAS--HRTEGRSLLPFVHGAPPA
    Streptomyces sulf LRVPG----APGGQVRDEFVSL-LDCTATHELAGLDPK---PAVDSRSLLPLMRGET--
     E.coli O157:H7 sulf IRSPQ----GERRQVTDVDTPVSH-IDLLPTMMALADIEKP---EILPGENLLAVKEPRG--
      Prevotella AptA VRYPK---AIKPGTVDKHLVQN-IDFAPTEDVAGVTKP---ETMSGRSFLDLFDGKGQD
       Agrobact. sulf IAAPG----WQPALIDAPVST-LDVTPTHCGEAGLDITSLKRWTDGEDLAALAAGTGGR
       Salmonella sulf IKYGK----HIPQGMVTDTPVYG-LDWDPTEANMMDFKLPT-DRTYDGQSLVPLLKDKTLK
             consensus ir-p-------g-v-d--v----iDvlptil-lagve-p----ieg-sll-lv-g---
```

Fig 3-3

```
                                                      42 43                         82  86
F2OS:  ASRPNIIIIMTDQQTADAMSNAGNKDLHTPAMDVLAANGTRFTRAYCAQPLCTPSRSAIFSGKMPHETGFTGNTPEKD---------GQ   109
ARSB:  SRPPHLVFLLADDLGWNDVGFHGS-RIRTPHLDALAAGGVLLDNYYTQP-LCTPSRSQLLTGRYQIRTGLHQIIWPC-------QPSC    121
ARSA:  ARPPNIVLIFADDLGYGDLGCYGHPSSTTPNLDQLAAGGLRFTDFYVPVSLCTPSRAALLTGRLPVRMGMYPGVLVPS------SRGG    99
PARS:  SKRPNFLVIVADDLGFSDIGAFGG-EIATPNLDALAIAGLRLTDFHTAS-TCSPTRSMLLTGTDHHIAGIGTMAEALTPELEGKPGYEGH  89

134 136
F2OS:  WPDSVLMMGKIFKAGGYKTGYVGKWHLPVP---VTKVAQHGFETIENTGMDYTDAVTPSQCANFNKKNKDNPFLLVASFLNPHDICEWA   197
ARSB:  VPLDEKLLPQLLKEAGYTTHMVCKWHLGMYR-KECLPTRRGFDTYFGYLLGSED------YYSHERCTLIDALNVTRCALDFRDGEEV    202
ARSA:  LPLEEVTVAEVLAARGYLTGMAGKWHLGVGPEGAFLPPHQGFHRFLGIPYSHDQGPCQNLTCFPPATPCDGGCDQGLVPIPLLANLSVEA  189
PARS:  LNERVVALPELLREAGYQTLMAGKWHLGLKP--EQTPHARGFERSFSLLPGAAN------HYGFEPPYDESTPRILKGTPALYVEDERYL  171

237
F2OS:  RGDNLKMDVLDAAPDTAFCPKLPANWPIPAFEPAIVREQQKVNPRTYPSVGWNESQWRKY-------------------------      257
ARSB:  ATGYKNMYSTNIFTKRAIALITNHPPEKPLFLYLALQSVHEPLQVPEEYLKPYDFIQDKN-------------------------      262
ARSA:  QPPWLPGLEARYMAFAHDLMADAQRQDRPFFLYYASHHTHYPQFS-----GQSFAERSG-----------------------           243
PARS:  DTLPEGFYSSDAFGDKLLQYLKERDQSRPFFAYLPFSAPHWPLQAPREIVEKYRGRYDAGPEALRQERLARLKELGLVEADVEAHPVLAL  261

295    308
F2OS:  -----------------RWAYNRLVEKVDNYMAMVLGSLKKYGIEDNTIIFTSDHG----------DGYAAHEWNQKQILYEEAARIPF   320
ARSB:  -----------------RHHYAGMVSLMDEAVGNVTAALKSSGLWNNTVFIFSTDNGGQ-TLAG--GNNWPLRGRKWSLWEGGVRGVG    330
ARSA:  -----------------RGPFGDSLMELDAAVGTLMTAIGDLGLLEETLVIFTADNGPE-TMRMSRGGCSGLLRCGKGTTYEGGVREPA   314
PARS:  TREWEALEDEERAKSARAMEVYAAMVERMDWNIGRVVDYLRRQGELDNTFVLFMSDNGAEGALLEAFPKFGPDLLGFLDRHYDNSLENIG   351

F2OS:  IISKIGQWKARTDDQLVCNGIDIIPTICGFAGIAKP--VGLKGLDLSKRIANPSVKLR-------DTLVIETDFADNELLGIKGRAVIT   401
ARSB:  FVASPLLKQKGVKNRELIHISDWLPTLVKLARGHTNGTKPLDGFDVWKTISEGSPSPRIELLHNIDPNFVDSSPCPRNSMAPAKDDSSLP  420
ARSA:  LAFWPGHIAPGVT-HELASSLDLLPTLAALAGAPLP-NVTLDGFDLSPLLGTGKSPRQSLFF--YPSYPDEVRGVFAVRTGKYKAHFFT    400
PARS:  RANSYVWYGP------RWAQAATAPSRLYKAFTTQGGIRVPALVRYPRLSRQGAISHAFATVMDVTPTLLDLAGVRHPGKRWRGREIAEP  435
```

```
              150
FH2S   QHGFETENTGMGDYT-------------------------DAVTPSQCANFNKKNK-DNPFLLVASELNP HDICEWAR-------
PARS   TPAEYVEDERYLDTLPEGFYS--------------------SDAEGDKLEQMLKERDQ-SRPFFAYLPESAPHWPLQAPREIVE
MDSA   DSNGKYEREQGYAT-----------------------------DIVTEHAVEEFLNQRDE-QKPFFLLVEHKAPHRTWMPNLKYLG
HGal6S EMVGRYYEEFPPNLKTGEAN-----------------------LTQIMLQEALDEIKRQAR-HHPFFLYWAVDATHAPVYASKPELG
HARSA  GCDQGLMPIPLTANLSVEAQPPWLPGLEARYMAFAHDLMADAQRQDRFFLYYASHHTHYPQFSGQSEAE
HARSB  RCAEDFRDGEEVATGYKNMYS--------------------TNIETIKRATALITNHPP-EKPLFLYLALQSVHEPLQVPEEMLK
HI2S   ANLECPNVDVLDMPEGTLPDKQ----------------------STEQAIQLLEKMKTSAS FFLAVGMHKPHIPFRYPKEFQK
cons.  -----l---ve---ia--t--------------------------yt--aldfl-----r-drPfflylaf--pH-p---pkefl- 200
FH2S   ------------GDNLKMDVLDAAPDTAFCPKLPAN-----------------------------------WPIPAFE
PARS   KYRGRYDAGPEALRQERLARLKEIGLMEADVEA------HPVLALTREWEALEDEERAKSARAMEVYAAMVER
MDSA   LYDKVEFPLPTTEWDDYATRGTCASQQEMTHAR------HMQLAYDNKVFEIDNAMRTRMLDRMDRLQKQAWD
HGal6S ------------TSQRGRMGDAVREIDDSTGKHLELLQD---LHVADNTFVFFTSDN---------GAALTSAPEQGGSN
HARSA  ------------RSGRGPEGDSLMELDAAVGTLMTAIGD---LGLLEETLVIFSTDN---------GPETMRMS-RGGCS
HARSB  PYDFIQDKNRHHMAGMVSLMDEAMGNVIAALKS------SGLWNNTVFIFSTDN---------GGQTLAG----GNN
HI2S   LYPLENITLAPDPEVPDGLPPVAYNPWMDIRQREDVQALNISVPYGPIPVDFQRKIRQSYFASVSYLDTQ
cons.  -----y-------------y-dev----ig-i--l--------vl--t--dn---i--------f--g-n 250
FH2S   PAIVREQQKVNPRTYPSVGWNESQWRKYRWAYNRLMEKVDNYMAMVLGSLKKYGIEDNTILFTSDHGDG
PARS   MDWNIGRVVDMLRRQGELDNTFVLFMSDNGAEGALLEAFPKFGPDLLGFLDRH--YDNSLENIGRANSYV
MDSA   AYYSPRNRAMLDAHLTDSALTVWKYQRYMHDYLSTIHSVDESMGETYEYLKNHNLLDNTHLVYCSDQGFY
HGal6S GPFLCGKQTTEGGMREPALAWPGHVTAGQVSHQLGSIMDLFTTSLALAGLT--PPSDRAEDGLNLLPT
HARSA  GLLRCGKGTTMEGGVREPALAFWPGHIAPG-VTHELASSLDLLPTLAALAGAP--LPN-VTLDGFDLSPL
HARSB  WPLRGRKWSLWEGGVRGVGFVASPLLKQKGVKNRELIHISDWLPTLVKLARGH--TNGTKPLDGFDVWKT
HI2S   VGRLLSALDDLQLANSTHIAFTSDHGWALGEHGEWAKYSNFDVATHVPLHFYVPGRTASLPEAGEKLFPY
cons.  g-------k-----feggm-eva----------g---------l--i-d-lptlall------ntv-i-g-dl-p-
```

Fig. 16-2

```
                 300                                                                350
FH2S   YAAHEWNQKQIDLMEEAAARIPFIISKTGQWKARTDDQ------------LVCNGEDIIPTICGFAGIAKPVGLK
PARS   WYGPRWAQAATAPSRLYKAFTTQGGTRVPALVRYPRLSRQGAISHAFATVMDVTPTLLDLAGVRHPGKR-
MDSA   MGEHGWFDKRFMYEESLRTPLVRYPKAIKPGTVDK-----------HLVQNIDFAPTLLDMAGVTKPETMS
HGal6S LQGRLMDRPIFYYRG----DTLMAAT-LGQHK-----------AHFWTWTNSWENFRQGIDFCPGQN-
HARSA  LGTGKSPSPRQSDEFYPSYPDEVRGVFAVR-TGKYK-----------AHFFTQGSAHSDTTADPACHASSS-
HARSB  SEGSPSPRIELLHNIDPNFVDSSPCPRNSMAPAK-----------DDSSLPEYSAFNTSVHAAIRHGNW-
HI2S   DPFDSASQLMEPGRQSMDLMELVSLFPTLAGLAGLQ-----------VPPRCPVPSFHVELCREGKNLLKHFR
cons.  1-g----r--ly----------g---------me--ps---vgg--rp--

400
FH2S   GLDLSKRIANPSVKLRDTLVIETDFADNELLEG---IKGRAVITKDFKYIVYDKGETREQLEDLEKDAGE
PARS   WRGREIAEPRGRSWLGWLSGETEAAHDENTVTGWELFGMRAIRQGDWKAVYLPAPVGPATWQLYDLARD
MDSA   GRSFLDLFDGKGQDWRQSHYYHYYDYPAEHHVRRHDGVRTDRYKLIHFYGAPMEGDHDTVDMEELYDMQN
HGal6S VSGVTTHNLEDHTKLPLIEHLGRDPGERFPLS----FASAEYQEALSRITSVQQHQEALVPAQPQINV
HARSA  LT------AHEPPLLYDLSKDPGENYNLLGGVAGATPEVLQALKQLQLLKAQLDAAVTFGPSQVAR
HARSB  KLLTGYPGCGYWFPPPSQYNVSEIPSSDPPTKTLWLFDIDRDPEERHDLSREYPHIVTKLLSRLQFYHK
HI2S   FRDLEEDPYLPGNPRELIAYSQYPRPSDIPQWNSDKPSLKDIKIMGYSIRTIDYRYTVWGENPDEFLAN
cons.  ---ly--s--p-ed---l----l-a-d-v---a-i---v-a--l---lw---l--

450
FH2S   MDNLAVKPAYKKKLNEMRAYIKLWCKQHQDSFYALKK---
PARS   PGEIHDLADSQPGKLAEELIEHWKRYVSETGVVEGASPFLV
MDSA   DPNELNNLYGKKGYEKTTKEEKKALKDYRKNLKVDEY----
HGal6S CN-WAVMNWAPPGCEKLGKCETPPESIPKKCLWSH-----
HARSA  GEDPALQICCHPGCTPRPACCHCPDPHA------------
HARSB  HSVPVYFPAQDPRCDPKATGWGPWM---------------
HI2S   FSDIHAGELYFVDSDPLQDHNMYNDSQGDLFQLLMP----
cons.  --pg-e-l--l-----------------------------
```

2-O SULFATASE COMPOSITIONS AND METHODS OF DEGRADATION THEREWITH

RELATED APPLICATIONS

This application is a divisional application of U.S. patent application Ser. No. 10/753761 filed on Jan. 7, 2004, now U.S. Pat. No. 7,270,815, and which claims the benefit under 35 U.S.C. §119 of U.S. provisional application No. 60/438,810, filed Jan. 8, 2003. Foreign priority benefits are claimed under 35 U.S.C. §119(a)-(d) or 35 U.S.C. §365(b) to Japanese application number 2003-271653, filed Jul. 7, 2003. Each of these applications is incorporated herein by reference in its entirety.

GOVERNMENT SUPPORT

Aspects of the invention may have been made using funding from National Institutes of Health Grants GM 57073 and CA90940. Accordingly, the Government may have rights in the invention.

FIELD OF THE INVENTION

The invention relates to 2-O sulfatase, related compositions, and methods of use thereof.

BACKGROUND OF THE INVENTION

Sulfated glycosaminoglycans such as heparin and the related heparan sulfate (HSGAGs) are complex, linear carbohydrates possessing considerable chemical heterogeneity (Esko, J. D., and Lindahl, U. (2001) *J Clin Invest* 108(2), 169-73, Shriver, Z., Liu, D., and Sasisekharan, R. (2002) *Trends Cardiovasc Med* 12(2), 71-72). Their structural diversity is largely a consequence of the variable number and position of sulfates present within a single HSGAG chain. Because of their highly anionic character, these polysaccharides historically have been relegated to an exclusively structural role, namely as a sort of hydration gel and scaffold comprising the extracellular matrix (ECM). Contrary to this limited perception, however, HSGAGs actually play an important and dynamic function in many critical biological processes ranging from development (Perrimon, N., and Bernfield, M. (2000) *Nature* 404(6779), 725-8) and tissue repair (Simeon, A., Wegrowski, Y., Bontemps, Y., and Maquart, F. X. (2000) *J Invest Dermatol* 115(6), 962-8) to apoptosis (Ishikawa, Y., and Kitamura, M. (1999) *Kidney Int* 56(3), 954-63, Kapila, Y. L., Wang, S., Dazin, P., Tafolla, E., and Mass, M. J. (2002) *J Biol Chem* 277(10), 8482-91). These polysaccharides are also central players in several pathological conditions such as cancer (Selva, E. M., and Perrimon, N. (2001) *Adv Cancer Res* 83, 67-80, Sasisekharan, R., Shriver, Z., Venkataraman, G., and Narayanasami, U. (2002) *Nat Rev Cancer* 2(7), 521-8), angiogenesis (Folkman, J., and Shing, Y. (1992) *Adv Exp Med Biol* 313, 355-64, Vlodavsky, I., Elkin, M., Pappo, O., Aingorn, H., Atzmon, R., Ishai-Michaeli, R., Aviv, A., Pecker, I., and Friedmann, Y. (2000) *Isr Med Assoc J 2 Suppl*, 37-45), certain neurodegenerative diseases such as Alzheimers (Cohlberg, J. A., Li, J., Uversky, V. N., and Fink, A. L. (2002) *Biochemistry* 41(5), 1502-11), athleroscelerosis (Sehayek, E., Olivecrona, T., Bengtsson-Olivecrona, G., Vlodavsky, I., Levkovitz, H., Avner, R., and Eisenberg, S. (1995) *Atherosclerosis* 114(1), 1-8), and microbial infectivity (Liu, J., and Thorp, S. C. (2002) *Med Res Rev* 22(1), 1-25). HSGAGs do so as part of proteoglycans found at the cell surface and within the ECM where they mediate signaling pathways and cell-cell communication by modulating the bioavailability and temporal-spatial distribution of growth factors, cytokines, and morphogens (Tumova, S., Woods, A., and Couchman, J. R. (2000) *Int J Biochem Cell Biol* 32(3), 269-88) in addition to various receptors and extracellular adhesion molecules (Lyon, M., and Gallagher, J. T. (1998) *Matrix Biol* 17(7), 485-93). HSGAG structure and function are inextricably related.

A study of the HSGAG structure-function paradigm (Gallagher, J. T. (1997) *Biochem Soc Trans* 25(4), 1206-9) requires the ability to determine both the overall composition of biologically relevant HSGAGs as well as ultimately ascertaining their actual linear sequence (fine structure). Therefore the availability of several chemical and enzymatic reagents which are able to cleave HSGAGs in a structure-specific fashion have proven to be valuable. One example of an important class of GAG degrading enzymes is the heparin lyases (heparinases) originally isolated from the gram negative soil bacterium *F. heparinum* (Ernst, S., Langer, R., Cooney, C. L., and Sasisekharan, R. (1995) *Crit Rev Biochem Mol Biol* 30(5), 387-444). Each of the three heparinases encoded by this microorganism cleave both heparin and heparan sulfate with a substrate specificity that is generally based on the differential sulfation pattern which exists within each GAG chain (Ernst, S., Langer, R., Cooney, C. L., and Sasisekharan, R. (1995) *Crit Rev Biochem Mol Biol* 30(5), 387-444, Rhomberg, A. J., Ernst, S., Sasisekharan, R., and Biemann, K. (1998) *Proc Natl Acad Sci USA* 95(8), 4176-81). In fact, *F. heparinum* uses several additional enzymes in an apparently sequential manner to first depolymerize and then subsequently desulfate heparin/heparan sulfate. In addition to heparinase I (Sasisekharan, R., Bulmer, M., Moremen, K. W., Cooney, C. L., and Langer, R. (1993) *Proc Natl Acad Sci USA* 90(8), 3660-4), we have recently cloned one of these enzymes, the Δ4,5 unsaturated glycuronidase (Myette, J. R., Shriver, Z., Kiziltepe, T., McLean, M. W., Venkataraman, G., and Sasisekharan, R. (2002) *Biochemistry* 41(23), 7424-7434). This enzyme has been recombinantly expressed in *E. coli* as a highly active enzyme. Because of its rather unique substrate specificity (Warnick, C. T., and Linker, A. (1972) *Biochemistry* 11(4), 568-72), this enzyme has already proven to be a useful addition to our PEN-MALDI based carbohydrate sequencing methodology (Venkataraman, G., Shriver, Z., Raman, R., and Sasisekharan, R. (1999) *Science* 286 (5439), 537-42).

SUMMARY OF THE INVENTION

2-O sulfatase has been cloned from the *F. heparinum* genome and its subsequent recombinant expression in *E. coli* as a soluble, highly active enzyme has been accomplished. Thus in one aspect the invention provides for a recombinantly produced 2-O sulfatase.

Recombinant expression may be accomplished in one embodiment with an expression vector. An expression vector may be a nucleic acid for SEQ ID NO:1, optionally operably linked to a promoter. In another embodiment the expression vector may be a nucleic acid for SEQ ID NO: 3 or a variant thereof also optionally linked to a promoter. In one embodiment the recombinantly expressed 2-O sulfatase is produced using a host cell comprising the expression vector. In another embodiment the expression vector may comprise any of the isolated nucleic acid molecules provided herein. In some embodiments the protein yields using the recombinantly expressed 2-O sulfatases provided herein exceed 100 mg of sulfatase enzyme per liter of induced bacterial cultures. In other embodiments the protein yield is 110, 115, 120, 125, 130, 150, 175, 200 mg or more per liter of induced bacterial culture. In other aspects methods of achieving such protein yields are provided comprising recombinantly expressing 2-O sulfatase and using at least one chromatographic step.

In another aspect of the invention isolated nucleic acid molecules are provided. The nucleic acid molecules may be (a) nucleic acid molecules which hybridize under stringent conditions to a nucleic acid molecule having a nucleotide sequence set forth as SEQ ID NO: 1 or SEQ ID NO: 3, and which code for a 2-O sulfatase, (b) nucleic acid molecules that differ from the nucleic acid molecules of (a) in codon sequence due to degeneracy of the genetic code, or (c) complements of (a) or (b). In one embodiment the isolated nucleic acid molecule comprises the nucleotide sequence set forth as SEQ ID NO: 1. In another embodiment the isolated nucleic acid molecule comprises the nucleotide sequence set forth as SEQ ID NO: 3. In still other embodiments the isolated nucleic acid molecule codes for SEQ ID NO: 2, and in yet other embodiments the isolated nucleic acid molecule codes for SEQ ID NO: 4.

The isolated nucleic acid molecules of the invention are also intended to encompass homologs and alleles. In one aspect of the invention, the isolated nucleic acid molecules are at least about 90% identical to the nucleotide sequence set forth as SEQ ID NO: 1 or 3. In other embodiments, isolated nucleic acid molecules that are at least 91%, 92%, 93%, 94%, 95%, 96%, 97%, 98%, or 99% identical to SEQ ID NO: 1 or 3 are given. In still other embodiments the isolated nucleic acid molecules are at least 99.5% or 99.9% identical to the nucleotide sequence set forth as SEQ ID NO: 1 or 3.

Therefore, in one aspect of the invention a 2-O sulfatase molecule produced by expressing the nucleic acid molecules provided herein is given. In some embodiments, as described above, the nucleic acid molecule is expressed recombinantly. In one embodiment the recombinant expression is carried out in E. coli.

In another aspect the 2-O sulfatase of the invention is a polypeptide having an amino acid sequence of SEQ ID NO: 2, or a functional variant thereof. In yet another aspect the polypeptide has an amino acid sequence of SEQ ID NO: 4, or a functional variant thereof. In still another aspect of the invention the 2-O sulfatase is an isolated 2-O sulfatase. In yet another embodiment the isolated 2-O sulfatase is synthetic. In yet another aspect of the invention an isolated polypeptide which comprises a 2-O sulfatase is also provided. The isolated polypeptide in some embodiments comprises a 2-O sulfatase having an amino acid sequence set forth as SEQ ID NO: 2. In other embodiments, the isolated polypeptide comprises a 2-O sulfatase which has the amino acid sequence as set forth as SEQ ID NO: 4. In still other embodiments the isolated polypeptide comprises a 2-O sulfatase which has the amino acid sequence as set forth as SEQ ID NO: 2 or 4 or functional variants thereof.

In one aspect of the invention, therefore, 2-O sulfatase functional variants are provided. In one embodiment the 2-O sulfatase functional variants include 2-O sulfatases that contain at least one amino acid substitution. In another embodiment the 2-O sulfatase functional variants contain 1, 2, 3, 4, 5, 6, 7, 8, 9, 10, 11, 12, 13, 14, 15, 16, 17, 18, 19, 20, 25, 30, 40 or more amino acid substitutions. In some of these embodiments the 2-O sulfatase functional variants are 2-O sulfatases that function similarly to the native 2-O sulfatase. In other embodiments the 2-O sulfatase functional variants are 2-O sulfatases that function differently than the native 2-O sulfatase. The different function can be, for instance, altered enzymatic activity or different substrate affinity. For example, as described herein, there are specific active site amino acids that are positioned to interact with specific constituents of glycosaminoglycans (e.g., Lys 175, Lys 238 with the planar carboxyl group of the uronic acid; Lys 107 and possibly Thr 104 with the 6-O sulfate of the glucosamine; and Lys 134, Lys 308 with the 2-O sulfate). Therefore, 2-O sulfatase functional variants can maintain these residues or contain amino acid substitutions at these residues to maintain or alter, respectively, the enzyme's function on a specific substrate. In yet other embodiments the amino acid substitutions occur outside of the active and binding sites as described herein. In still other embodiments the active and binding sites are targeted for substitution. In some of the foregoing embodiments the amino acid substitutions occur outside of the catalytic domain given in SEQ ID NO: 6. In other embodiments the amino acid substitutions occur within this catalytic domain. In still other embodiments the choice of amino acid substitutions can be based on the residues that are found to be conserved between the various sulfatase enzymes (e.g., see the sequence alignments provided in FIGS. 3, 9 and 16) (e.g., highly conserved His 136, His 191, Asp 42, Asp 63, Asp 295). Amino acid substitutions can be conservative or non-conservative.

In one aspect of the invention the amino acid sequence of the isolated polypeptide contains (a) at least one residue selected from Arg 86, Asp 42, Asp 159, Asp 295, Cys 82, FGly 82, Gln 43, Gln 237, Glu 106, Gln 309, His 136, His 296, Leu 390, Leu 391, Leu 392, Lys 107, Lys 134, Lys 175, Lys 238, Lys 308 or Thr 104 and (b) at least one amino acid substitution. In one embodiment of the invention the amino acid sequence of the isolated polypeptide contains a Cys 82 residue and at least one amino acid substitution. In another embodiment the isolated polypeptide contains a Cys 82 residue which is subsequently modified to formyl glycine and at least one amino acid substitution. In still other embodiments the isolated polypeptide contains a FGly 82 residue and at least one amino acid substitution.

In another aspect of the invention functional variants include a 2-O sulfatase which contains at least one amino acid residue that has been substituted with a different amino acid than in native 2-O sulfatase and wherein the residue that has been substituted is selected from Arg 86, Asp 42, Asp 159, Asp 295, Gln 43, Gln 237, Glu 106, Gln 309, His 136, His 296, Leu 390, Leu 391, Leu 392, Lys 107, Lys 134, Lys 175, Lys 238, Lys 308 and Thr 104.

In another aspect, the invention is a composition comprising, an isolated 2-O sulfatase having a higher specific activity than native 2-O sulfatase. In some embodiments, the 2-O sulfatase has a specific activity that is at least about 5- fold higher than native 2-O sulfatase. The specific activity of the 2-O sulfatase in other embodiments may be 6-, 7-, 8-, 9-, 10-, 11-, 12-, 13-, 14-, 15-, 16-, 17-, 18-, or 19-fold higher than the specific activity of the native enzyme. In other embodiments the specific activity may be about 20-, 25-, 30-, 40- or 50-fold higher. In one embodiment the 2-O sulfatase has a specific activity that is about ten fold higher than the specific activity of the native enzyme.

In another aspect the invention also provides a method of degrading a glycosaminoglycan. The method may be performed by contacting the glycosaminoglycan with a 2-O sulfatase of the invention in an effective amount to degrade the glycosaminoglycan. In other embodiments the method may be performed by contacting the glycosaminoglycan with at least one other glycosaminoglycan degrading enzyme. In some embodiments the at least one other glycosaminoglycan degrading enzyme is heparinase or glycuronidase. In other embodiments the glycosaminoglycan is contacted with the at least one other glycosaminoglycan degrading enzyme concomitantly with the 2-O sulfatase. In still other embodiments the glycosaminoglycan is contacted with the at least one other glycosaminoglycan degrading enzyme prior to or subsequent to contacting the glycosaminoglycan with 2-O sulfatase. In still another embodiment the glycosaminoglycan is contacted with a heparinase prior to contact with a 2-O sulfatase.

In some embodiments the glycosaminoglycan is a long chain saccharide. In such embodiments the glycosaminoglycan is a tetrasaccharide or a decasaccharide. In other embodiments the glycosaminoglycan contains a 2-O sulfated uronic acid at the non-reducing end. In still other embodiments the glycosaminoglycan contains a β1→4 linkage.

In yet another embodiment the glycosaminoglycan is a chondroitin sulfate. In other embodiments the glycosaminoglycan is a highly sulfated glycosaminoglycan. In such embodiments the highly sulfated glycosaminoglycan contains a 6-O sulfated glucosamine. In yet other embodiments the highly sulfated glycosaminoglycan contains a glucosamine sulfated at the N-position.

In some aspects of the invention degraded glycosaminoglycans prepared by the methods described herein are provided. In still other aspects of the invention a composition which contains a degraded glycosaminoglycan is given. In still another aspect of the invention the composition is a pharmaceutical preparation which also contains a pharmaceutically acceptable carrier.

The present invention also provides methods for the analysis of a glycosaminoglycan or group of glycosaminoglycans. In one aspect the invention is a method of analyzing a glycosaminoglycan by contacting a glycosaminoglycan with the 2-O sulfatase of the invention in an effective amount to analyze the glycosaminoglycan.

The present invention also provides 2-O sulfatase immobilized on a solid support. In another embodiment at least one other glycosaminoglycan degrading enzyme is also immobilized on the solid support.

In one aspect of the invention a method for identifying the presence of a particular glycosaminoglycan in a sample is provided. In another aspect of the invention a method for determining the identity of a glycosaminoglycan in a sample is provided. In yet another aspect of the invention a method for determining the purity of a glycosaminoglycan in a sample is also provided. In still a further aspect of the invention a method for determining the composition of a glycosaminoglycan in a sample is provided. Yet another aspect of the invention is a method for determining the sequence of saccharide units in a glycosaminoglycan. In some embodiments, these methods can further comprise an additional analytical technique such as mass spectrometry, gel electrophoresis, capillary electrophoresis or HPLC.

In another aspect the invention is a method of inhibiting angiogenesis by administering to a subject in need thereof an effective amount of any of the pharmaceutical preparations described herein for inhibiting angiogenesis.

In another aspect a method of treating cancer by administering to a subject in need thereof an effective amount of any of the pharmaceutical preparations described herein for treating cancer is also provided.

Yet another aspect of the invention is a method of inhibiting cellular proliferation by administering to a subject in need thereof an effective amount of any of the pharmaceutical preparations described herein for inhibiting cellular proliferation.

In yet another aspect of the invention a method of treating neurodegenerative disease by administering to a subject in need thereof an effective amount of any of the pharmaceutical preparations described herein for treating neurodegenerative disease is provided. In one embodiment the neurodegenerative disease is Alzheimer's disease.

Another aspect of the invention is a method of treating atherosclerosis by administering to a subject in need thereof an effective amount of any of the pharmaceutical preparations described herein for treating atherosclerosis.

In another aspect of the invention a method of treating or preventing microbial infection by administering to a subject in need thereof an effective amount of any of the pharmaceutical preparations described herein for treating or preventing microbial infection is given.

In yet another aspect of the invention a method of controlling apoptosis by administering to a subject in need thereof an effective amount of any of the pharmaceutical preparations described herein for controlling apoptosis is provided.

In other aspects of the invention methods of repairing tissue or controlling development are also provided.

In some embodiments of the methods of the invention the 2-O sulfatase is used concurrently with, prior to or following treatment with at least one other glycosaminoglycan degrading enzyme. In some embodiments the at least one other glycosaminoglycan degrading enzyme is heparinase or glycuronidase. In some embodiments of the compositions or pharmaceutical preparations of the invention other enzymes such as heparinase and/or glycuronidase may be included.

In other aspects of the invention, compositions, pharmaceutical preparations and therapeutic methods are provided with/using the 2-O sulfatase or the degraded glycosaminoglycans alone or in combination.

Compositions of any of the 2-O sulfatases, degraded glycosaminoglycans, nucleic acids, polypeptides, host cells or vectors described herein are also encompassed in the invention. Pharmaceutical preparations of any composition provided herein are also provided in some embodiments. In these embodiments the pharmaceutical preparations contain a pharmaceutically acceptable carrier.

In still another aspect of the invention, a substantially pure, non-recombinantly produced 2-O sulfatase that has a purity that is about 3000-fold greater than crude bacterial lysate is provided. In some embodiments the purity of the substantially pure, non-recombinantly produced 2-O sulfatase is about 4000-, 5000-, 6000-, 7000-, 8000-, 9000- or 10,000-fold more pure than crude bacterial lysate. In some embodiments the substantially pure, non-recombinantly produced 2-O sulfatase is obtained by a multi-step fractionation method. In one embodiment the method is a five-step fractionation method. In this aspect of the invention, the term "substantially pure" means that the proteins are essentially free of other substances to an extent practical and appropriate for their intended use.

Each of the limitations of the invention can encompass various embodiments of the invention. It is, therefore, anticipated that each of the limitations of the invention involving any one element or combinations of elements can be included in each aspect of the invention.

These and other aspects of the invention, as well as various advantages and utilities, will be more apparent with reference to the detailed description of the preferred embodiments.

BRIEF DESCRIPTION OF THE FIGURES

FIG. 2 provides the *F. heparinum* 2-O sulfatase coding sequence (open reading frame from genomic clone S4A. The nucleic acid and amino acid sequence (SEQ ID NOs: 1 and 2, respectively) of the full length gene for the 2-O sulfatase begins with the first methionine (the nucleic acid and amino acid sequences including the sequence upstream of the first methionine are provided as SEQ ID NOS: 38 and 39, respectively). The nucleic acid and amino acid sequence of the truncated 2-O sulfatase which lacks the first 24 amino acids (herein referred to as 2-O $\Delta N^{1-24}$) of the full length gene are given as SEQ ID NOs: 3 and 4, respectively. Translation initiation and termination codons are shown in bold. Primers used in original PCR screen are noted by horizontal arrows. Internal Nde 1 site is double underscored. Corresponding amino acid sequence of select sulfatase peptides are boxed. Sulfatase consensus sequence CXPXRXXXXS/TG (SEQ ID NO: 5) is boxed and shaded with active site cysteine at position 82 noted by an asterisk. Putative signal sequence is overscored with predicted peptidase cleavage site represented by a vertical arrow.

FIG. 3 depicts a 2-O sulfatase multiple sequence alignment (SEO ID NOs: 40-58). The flavobacterial enzyme is a member of a large sulfatase family. Alignment shown excludes 2-O sulfatase carboxy terminus (amino acids 374-468). The putative active site is boxed with critically modified cysteine noted by an asterisk. Invariant residues are shaded in dark gray, partial identity in light gray, conservative substitutions in charcoal. Multiple sequence alignment was generated by ClustalW using only select bacterial sequences identified from a BLASTP search of the protein database. Mammalian sulfatases are not included. Most sequences listed correspond to the open reading frame of genes to which only a putative sulfatase function has been ascribed. GenBank accession numbers are as follows: AA605721 (*Pseudomonas aeruginoasa.*); AL355753 (*Streptomyces coelicolor*); BAB79937 (*E. coli* O 157: H7); AAF72520 (*Prevotella sp.* MdsA gene); AAL:45441 (*Agrobacterium tumefaciens*); AAL19003 (*Salmonella typhimurium*).

FIG. 9. illustrates the multiple sequence alignment of sulfatases using ClustalW (SEQ ID NOs: 59-62). The sequence of *F. heparinum* 2-O sulfatase (F2OS) was aligned with human arylsulfatase B (ARSB), human arylsulfatase A (ARSA) and *P. aeruginosa* arylsulfatase (PARS). The amino and carboxyl termini are not shown. The sequence numbers for each sulfatase are listed on the right. The numbers listed above the alignment correspond specifically to F2OS sequence positions (see FIG. 2 above). The critical active site cysteines are highlighted in black. Other highly conserved amino acids are highlighted in gray.

FIG. 16 shows a multiple sequence alignment of the sulfatases using ClustalW (SEQ ID NOs: 2 and 63-83). The putative active site is boxed, with critically modified cysteine noted by an asterisk. Invariant residues are shaded in dark gray, those with partial identity in light gray, and conservative substitutions in charcoal. Multiple sequence alignment was generated by ClustalW using only select sequences identified from a BLASTP search of the protein data base. Mammalian sulfatases are included. Enzymes are abbreviated as follows. FH2S, *F. heparinum* 2-O-sulfatase; PARS, *P. aeruginosa* arylsulfatase; MDSA, *Prevotella sp.* MdsA gene; HGal6S, human N-acetylgalactosamine- 6-sulfate sulfatase (chondroitin 6-sulfatase); HARSA, human cerebroside-3-sulfate sulfatase (arylsulfatase A); HARSB, human N-acetylgalactosamine-4 sulfate sulfatase (arylsulfatase B); HI2S, human iduronate-2-sulfate sulfatase; cons, consensus sequence. The GenBankTM protein accession numbers for sulfatases listed are as follows: CAA88421, *P. aeruginosa arylsulfatase*; AAF72520, *Prevotella sp.* MdsA mucin desulfating gene; AAC51350, Homo sapiens N-acetylgalactosamine-6-sulfate sulfatase; AAB03341, H. sapiens cerebroside-3-sulfate sulfatase (arylsulfatase A); AAA51784, H. sapiens N-acetylgalactosamine-4-sulfate sulfatase (arylsulfatase B); AAA63197, H. sapiens iduronate-2-sulfate sulfatase.

DETAILED DESCRIPTION OF THE INVENTION

Figure 1A:
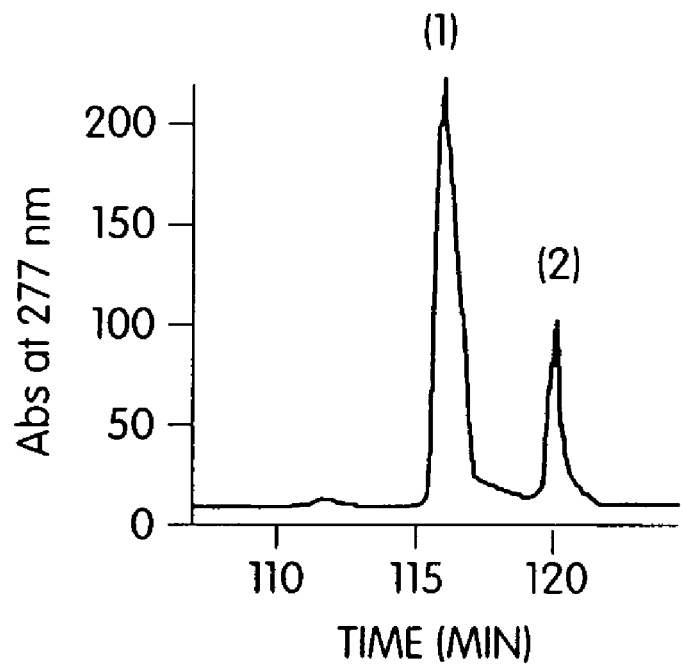
FIG. 1 provides the results of Flavobacterium 2-O sulfatase purification and proteolysis. Panel (A) provides the final RP-HPLC chromatography of blue-Sepharose CL-6B purified sulfatase. Panel (B) illustrates the C4 RP-HPLC chromatographic resolution of sulfatase peptides generated by a limit trypsin digestion of the major peak shown in Panel (A).

Heparin and heparin sulfate glycosaminoglycans (HS-GAGs) are structurally complex linear polysaccharides (Esko, J. D., and Lindahl, U. (2001) *J Clin Invest* 108(2), 169-73, Lindahl, U., Kusche-Gullberg, M., and Kjellen, L. (1998) *J Biol Chem* 273(39), 24979-82) comprised of repeating disaccharides of uronic acid (α-L-iduronic or β-D-glucuronic) linked 1→4 to α-D-glucosamine. The extensive chemical heterogeneity of these biopolymers derives from both the variable number of their constituent disaccharides as well as the combinatorial potential for chemical modification at specific positions within each of these building blocks. Such modifications include acetylation or sulfation at the N-position of the glucosamine, epimerization of glucuronic acid to iduronic acid and additional sulfations at the 2-O position of the uronic acid in addition to the 3-O, 6-O position of the adjoining glucosamine. It is a highly variable sulfation pattern, in particular, that ascribes to each GAG chain a unique structural signature. In turn, this signature dictates specific GAG-protein interactions underlying critical biological processes related to cell and tissue function.

One of the more formidable challenges currently facing the glycobiology field is the design of effective analytical methods to study this structure-function relationship at the molecular level. Given this critical structure-function relationship of GAG sulfation, enzymes which can hydrolyze these sulfates in a structurally-specific manner become important in several ways. To begin with, the systematic desulfation of GAGs at discrete positions is central to GAG catabolism that occurs in divergent organisms ranging from bacteria to mammals. In addition, the in vivo desulfation of intact GAG chains both at discrete chemical positions and in a cell specific, temporally relevant context is also likely to serve as an important molecular switch for abrogating targeted GAG-protein interactions. 2-O sulfatase is a desulfating enzyme that can be now added to the repertoire of enzymes used to analyze GAGs and degrade them in a specific manner. As used herein, the term "degraded glycosaminoglycan" or "GAG fragment" is intended to encompass a glycosaminoglycan that has been altered from its original form by the activity of a 2-O sulfatase or other enzyme that can act thereon. The degraded glycosaminoglycan includes glycosaminoglycans that have been altered by the activity of a 2-O sulfatase in some combination with other glycosaminoglycan degrading enzymes as described herein. The degraded glycosaminoglycan may be desulfated, cleaved or desulfated and cleaved. Any of the degraded products produced by the activity of the 2-O sulfatase and/or other enzymes on the glycosaminoglycan are intended to be used in the compositions, pharmaceutical preparations and methods of the invention. In addition, this sulfatase can be used in treatment methods along with the GAG fragments they degrade. 2-O sulfatase is a member of a large enzyme family that hydrolyze a wide array of sulfate esters (for a review, see (Parenti, G., Meroni, G., and Ballabio, A. (1997) *Curr Opin Genet Dev* 7(3), 386-91, von Figura, K., Schmidt, B., Selmer, T., and Dierks, T. (1998) *Bioessays* 20(6), 505-10)). This enzyme exhibits 2-O specific sulfatase activity as measured using the trisulfated, unsaturated heparin disaccharide $\Delta U_{2S}H_{NS,6S}$ as a substrate (described below). The activity of the enzyme is not limited to 2-O desulfation alone, however, as 2-O sulfatase was found to hydrolyze at the 6-O and 2N positions of glucosamine. 2-O sulfatase can be used to hydrolyze heparin and chondroitin disaccharides and can also desulfate GAGs with longer chain lengths such as tetra- and decasaccharides. Furthermore, 2-O sulfatase has been found to work with other GAG degrading enzymes such as heparinases and Δ 4,5 glycuronidase and can be used in conjunction with these other enzymes as described herein.

Like the Δ 4,5 glycuronidase, which we have recently cloned and expressed (Myette, J. R., Shriver, Z., Kiziltepe, T., McLean, M. W., Venkataraman, G., and Sasisekharan, R. (2002) *Biochemistry* 41(23), 7424-7434), we have successfully cloned from *Flavobacterium heparinum* and expressed the 2-O sulfatase in *E. coli*, from which milligram quantities of highly active, soluble enzyme were readily purified. As was also the case for the glycuronidase, we found that the yield of soluble recombinant enzyme was greatly improved by the engineered removal of the hydrophobic N-terminal signal sequence comprised of the first 24 amino acids. This signal sequence was predicted by the von Heinje method which also identified the likely signal peptidase cleavage recognition sequence AXAXA. By engineering a 2-O sulfatase N-terminal truncation lacking this sequence (herein referred to as 2-O $\Delta N^{1-24}$), we achieved protein yields exceeding 100 mg of relatively pure sulfatase per liter of induced bacterial cultures using a single chromatographic step.

The invention, therefore, provides, in part, a recombinantly produced 2-O sulfatase. As used herein, a "recombinant 2-O sulfatase" is a 2-O sulfatase that has been produced through human manipulation of the nucleic acid that encodes the enzyme. The human manipulation usually involves joining the nucleic acid that encodes the 2-O sulfatase to the genetic material of a different organism and, generally, a different species. "Recombinant" is a term of art that is readily known to one of skill, and techniques for the recombinant expression of 2-O sulfatase are readily available to those of skill in the art and include those described in Sambrook et al., Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998). Other techniques for recombinant expression including examples of expression systems are described further below.

As provided herein, recombinant technology can be used to produce a 2-O sulfatase encoded by the nucleic acid sequence of SEQ ID NO: 1 or having the amino acid sequence of SEQ ID NO: 2. In other aspects of the invention a 2-O sulfatase encoded by the nucleic acid sequence of SEQ ID NO: 3 or having the amino acid sequence of SEQ ID NO: 4 can be prepared. The 2-O sulfatase as provided herein is, in general, produced through the manipulation of isolated nucleic acids.

The invention also provides the isolated nucleic acid molecules that code for a 2-O sulfatase as described herein. The term "isolated nucleic acid", as used herein, means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

According to the invention, isolated nucleic acid molecules that code for a 2-O sulfatase include: (a) nucleic acid molecules which hybridize under stringent conditions to a molecule selected from a group consisting of the nucleotide sequences set forth as SEQ ID NO: 1 and 3 and which code for a 2-O sulfatase or parts thereof, (b) deletions, additions and substitutions of (a) which code for a 2-O sulfatase or parts thereof, (c) nucleic acid molecules that differ from the nucleic acid molecules of (a) or (b) in codon sequence due to the degeneracy of the genetic code, and (d) complements of (a), (b) or (c). The isolated nucleic acid molecules include isolated nucleic acid molecules that code for a 2-O sulfatase which has an amino acid sequence set forth as SEQ ID NOs: 2 and 4.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating 2-O sulfatase. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The isolated nucleic acid molecules of the invention are also intended to encompass homologs and alleles which can be identified by conventional techniques. Identification of human and other organism homologs of 2-O sulfatase polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode a 2-O sulfatase identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "stringent conditions" as used herein refers to parameters with which the art is familiar. Such parameters include salt, temperature, length of the probe, etc. The amount of resulting base mismatch upon hybridization can range from near 0% ("high stringency") to about 30% ("low stringency"). Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F.M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5mM NaH2PO4(pH7), 0.5% SDS, 2mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

The skilled artisan also is familiar with the methodology for screening cells for expression of such molecules, which then are routinely isolated, followed by isolation of the pertinent nucleic acid. Thus, homologs and alleles of the 2-O sulfatase of the invention, as well as nucleic acids encoding the same, may be obtained routinely, and the invention is not intended to be limited to the specific sequences disclosed. It will be understood that the skilled artisan will be able to manipulate the conditions in a manner to permit the clear identification of homologs and alleles of the 2-O sulfatase nucleic acids of the invention. The skilled artisan also is familiar with the methodology for screening cells and libraries for expression of such molecules which then are routinely isolated, followed by isolation of the pertinent nucleic acid molecule and sequencing.

In general, homologs and alleles typically will share at least 90% nucleotide identity and/or at least 95% amino acid identity to the sequences of 2-O sulfatase nucleic acids and polypeptides, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for 2-O sulfatase related genes, such as homologs and alleles of 2-O sulfatase, a Southern blot may be performed using the foregoing conditions, together with a radioactive probe. After washing the membrane to which the DNA is finally transferred, the membrane can be placed against X-ray film or a phosphoimager plate to detect the radioactive signal.

The recombinantly produced 2-O sulfatase as provided herein exhibited robust, 2-O specific sulfatase activity. The success with expressing a highly active 2-O sulfatase clearly validates our use of E. coli as a recombinant expression system for the large-scale production of active enzyme. Therefore, active isolated 2-O sulfatase polypeptides (including whole proteins and partial proteins) are provided herein which include isolated 2-O sulfatase polypeptides that have the amino acid sequence of SEQ ID NO: 2 or SEQ ID NO: 4.

Polypeptides can be isolated from biological samples, and can also be expressed recombinantly in a variety of prokaryotic and eukaryotic expression systems, such as those described above, by constructing an expression vector appropriate to the expression system, introducing the expression vector into the expression system, and isolating the recombinantly expressed protein. Polypeptides can also be synthesized chemically using well-established methods of peptide synthesis.

As used herein, "isolated polypeptide" means the polypeptide is separated from its native environment and present in sufficient quantity to permit its identification or use. This means, for example: (i) selectively produced by expression cloning or (ii) purified as by chromatography or electrophoresis. Isolated proteins or polypeptides may be, but need not be, substantially pure. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, i.e., isolated from other proteins.

As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations. As used herein, a "substantially pure 2-O sulfatase" is a preparation of 2-O sulfatase which has been isolated or synthesized and which is greater than about 90% free of contaminants. Preferably, the material is greater than 91%, 92%, 93%, 94%, 95%, 96%, 97%, 98%, or even greater than 99% free of contaminants. The degree of purity may be assessed by means known in the art. One method for assessing the purity of the material may be accomplished through the use of specific activity assays.

The cloned, full-length gene of the 2-O sulfattase encodes an open reading frame (ORF) of 468 amino acids (FIG. 2), with a predicted molecular mass of 51.9 kDa. This theoretical molecular weight is approximately 10 kDa less than the value reported in the literature (McLean, M. W., Bruce, J. S., Long, W. F., and Williamson, F. B. (1984) *Eur J Biochem* 145(3), 607-15). Based on its amino acid composition, the encoded protein is quite basic (theoretical pI of 8.75). A further analysis of its primary amino acid sequence unequivocally places this ORF as a member of a larger sulfatase family. As members of a large enzyme family, the sulfatases hydrolyze a wide array of sulfate esters (for a review, see (Parenti, G., Meroni, G., and Ballabio, A. (1997) *Curr Opin Genet Dev* 7(3), 386-91, von Figura, K., Schmidt, B., Selmer, T., and Dierks, T. (1998) *Bioessays* 20(6), 505-10)). Their respective substrates include sulfated complex carbohydrates such as the glycosaminoglycans (GAGs), steroids, sphingolipids, xenobiotic compounds, and amino acids such as tyrosine. Additionally, many of these enzymes are able to hydrolyze in vitro smaller synthetic substrates (e.g., 4-nitrophenyl sulfate and catechol sulfate). It is for this reason that these enzymes are often generically described as "arylsulfatases" (even when their preferred in vivo substrate is ill-defined). Despite their disparate substrate specificities, the members of this enzyme family share both considerable structural homology and a common catalytic mechanism with one another (Waldow, A., Schmidt, B., Dierks, T., von Bulow, R., and von Figura, K. (1999) *J Biol Chem* 274(18), 12284-8).

The flavobacterial 2-O sulfatase possesses considerable sequence homology to other bacterial (and non-bacterial) sulfatases, especially within its amino terminus in which resides a highly conserved sulfatase domain. This signature catalytic domain is readily identified by the consensus sequence C/SXPXRXXXXS/TG (SEQ. ID NO: 6). The conserved cysteine (or less commonly serine) within this sulfatase motif is of particular functional importance as it is covalently modified to a L-Cα-formylglycine (L-2-amino-3-Oxo-propionic acid). The ubiquitous importance of this chemical modification was first functionally identified by its relationship to the etiology of multiple sulfatase deficiency (MSD), a genetically recessive disorder in which there is a complete loss of sulfatase activity due to a lack of this critical aldehyde (FGly) within the active site of all expressed sulfatases (Kolodny, E. H. a. F., A. L. (1995) in *The Metabolic and Molecular Bases of Inherited Disease* (Scriver, C. R., Beaudet, A. L., Sly, W. S., and Valle, D., ed), pp. 2693-2741, McGraw-Hill, N.Y.). We have identified the conserved sulfatase active site by sequence homology which we have found includes a cysteine and not a serine as the critical amino acid predicted to be chemically modified as a formylglycine in vivo. An empirical demonstration of this active-site aldehyde at this position is presented in Examples.

While the cloned flavobacterial sulfatase exhibits the highest sequence similarity to the bacterial arylsulfatases (especially the arylsulfatase from *Pseudomonas aeruginosa*), we point out that a limited homology of the 2-O sulfatase does extend to the mammalian glycosaminoglycan sulfatases functioning in the lysosomal degradation pathway. As is the case for the bacterial enzymes, this sequence homology is strongest in the $NH_2$-terminus where the putative sulfatase domain resides. Among the human lysosomal enzymes, it is the galactosamine (N-acetyl)-6-sulfate sulfatase (chondroitin 6-O sulfatase) which exhibits the closest similarity with the flavobacterial 2-O sulfatase; the two enzymes possess approximately 26% identity when comparing their entire protein sequences. There are also two functionally related lysosomal sulfatases which specifically hydrolyze the 2-OH position of uronic acid. These enzymes are the iduronate 2-sulfate sulfatase (IDS) (Bielicki, J., Freeman, C., Clements, P. R., and Hopwood, J. J. (1990) *Biochem J* 271(1), 75-86) and the glucuronic-2-sulfate sulfatase (Freeman, C., and Hopwood, J. J. (1989) *Biochem J* 259(1), 209-16). The IDS and flavobacterial 2-O sulfatase exhibit only a limited sequence homology (less than 22% identity), however.

Both of these enzymes desulfate heparan sulfate, the iduronate-2-sulfate sulfatase (IDS) also acts on dermatan sulfate. Both enzymes possess an acidic pH optima for activity, a fact consistent with their location within the lysosome. The two sulfatases initially exist as precursors which must be proteolytically processed for activity. The native molecular weight of the human IDS precursor has been reported in the range of 42 to 65 kDa (Bielicki, J., Freeman, C., Clements, P. R., and Hopwood, J. J. (1990) *Biochem J* 271(1), 75-86), while its theoretical mass based entirely on its amino acid composition is approximately 62 kDa. As such, the mammalian lysosomal IDS is somewhat larger than its flavobacterial counterpart, while also requiring substantial posttranslational modification for maximal enzyme activity. The acidic pH optima for the lysosomal enzymes would also appear to limit their in vitro use for the determination of HSGAG composition, at least when used in tandem with other flavobacterial HSGAG degrading enzymes such as the heparinases or the Δ 4,5 glycuronidase; these latter enzymes all possess a pH optima much closer to neutrality.

A homology-based structural model of the 2-O sulfatase active site was constructed using as a framework the available crystallographic data for three highly related arylsulfatases. In this model, we have identified important structural parameters within the enzyme active site relevant to enzyme function, especially as relates to its substrate specificity (substrate binding and catalysis). By docking various disaccharide substrates, we were also able to make specific predictions concerning structural determinants present within these potential substrates that would complement this unique active site architecture. These determinants included the position and number of sulfates present on the glucosamine, oligosaccharide chain length, the presence of a Δ 4,5 unsaturated double bond, and the exolytic vs. endolytic potential of the enzyme. These predictions were then tested against biochemical and kinetic data which largely validated our substrate specificity predictions. Our modeling approach was further complemented experimentally using aldehyde-specific chemical labeling, peptide mapping in tandem with mass spectrometry and site-directed mutagenesis to physically demonstrate the presence of a covalently modified cysteine (formyl glycine (FGly)) within the active site. This combinatorial approach of structure modeling and biochemical studies has provided insight into the molecular basis of enzyme function.

The crystal structures of two human lysosomal sulfatases, cerebroside-3-sulfate 3-sulfohydrolase (arylsulfatase A), (Lukatela, G., Krauss, N., Theis, K., Selmer, T., Gieselmann, V., von Figura, K., and Saenger, W. (1998) *Biochemistry* 37(11), 3654-64, von Bulow, R., Schmidt, B., Dierks, T., von Figura, K., and Uson, I. (2001) *J Mol Biol* 305(2), 269-77) N-acetylgalactosamine-4-sulfate 4-sulfohydrolase (arylsulfatase B) (Bond, C. S., Clements, P. R., Ashby, S. J., Collyer, C. A., Harrop, S. J., Hopwood, J. J., and Guss, J. M. (1997) *Structure* 5(2), 277-89), and a bacterial arylsulfatase from *Pseudomonas aeruginosa* (Boltes, I., Czapinska, H., Kahnert, A., von Bulow, R., Dierks, T., Schmidt, B., von Figura, K., Kertesz, M. A., and Uson, I. (2001) *Structure* (Camb) 9(6), 483-91) have been solved. These three sulfatases share an identical alkaline-phosphatase like structural fold (according to Structural Classification of Proteins database (www.p-db.org)) comprised of a series of mixed parallel and antiparallel β strands flanked by long and short a helices on either side (Lukatela, G., Krauss, N., Theis, K., Selmer, T., Gieselmann, V., von Figura, K., and Saenger, W. (1998) *Biochemistry* 37(11), 3654-64, Bond, C. S., Clements, P. R., Ashby, S. J., Collyer, C. A., Harrop, S. J., Hopwood, J. J., and Guss, J. M. (1997) *Structure* 5(2), 277-89, Boltes, I., Czapinska, H., Kahnert, A., von Bulow, R., Dierks, T., Schmidt, B., von Figura, K., Kertesz, M. A., and Uson, I. (2001) *Structure* (Camb) 9(6), 483-91, von Bulow, R., Schmidt, B., Dierks, T., von Figura, K., and Uson, I. (2001) *J Mol Biol* 305(2), 269-77). In addition to their common structural fold, these sulfatase structures also possess a high degree of homology within their respective active sites, especially in the region localized around the modified cysteine (FGly). Taken together, these crystal structures present a clear and consistent description of conserved active site residues at least as it relates to a likewise conserved mechanism of sulfate ester hydrolysis. At the same time, this strong structural homology is somewhat surprising considering that at least two of these sulfatases act on notably different substrates, e.g., sulfated sphingolipid vs. sulfated glycosaminoglycan (GAG).

It was discovered that 2-O sulfatase has a relatively high cysteine content. Apart from the catalytic cysteine at position 82, none of the remaining seven cysteines appeared to be highly conserved among other members of the sulfatase family. Enzyme activity was not inhibited with the addition of DTNB (Ellman's reagent) or DTT. This general lack of inhibition by these two cysteine-reactive agents suggests at least two probabilities. First, the 2-O sulfatase does not require intramolecular disulfide linkages to critically stabilize a catalytically active conformation. Second, free sulfhydryls are not directly participating in catalysis. It is possible, however, that a few of these cysteines are buried and therefore not accessible to sulfhydryl exchange. At least five of the eight cysteines, however, do react with DTNB under nondenaturing conditions. This latter fact suggests an alternate role for these solvent-accessible cysteines (along with specific histidines) i.e., metal-coordinating thiolates. Comparison between the 2-O sulfatase and alkaline phosphatase reveals that these enzymes are esterases with similar catalytic mechanisms, including the presumptive formation of a covalent intermediate. The two hydrolytic enzymes also possess structurally related domains, in particular, a highly superimposible active site that includes a divalent metal binding pocket. In the case of alkaline phosphatase, it is zinc rather than calcium (or $Mg^{+2}$) that is coordinated within this pocket.

The 2-O sulfatase possesses 67 basic amino acids, including the catalytic histidine at position 136, a proximal lysine at position 134 and an invariant arginine at position 86 found within the defining sulfatase consensus sequence. Moreover, crystal structures of the active site of related sulfatases each clearly show at least four basic residues participating in catalysis which was also found in our homology model. A masking of these important charges by exogenous ions would interfere with their catalytic function.

Of the 8 histidines present in the flavobacterial 2-O sulfatase, H136 is invariantly conserved among the structurally related bacterial sulfatases examined. For each of these enzymes, this highly conserved histidine is found within a putative consensus sequence GKWHX (SEQ. ID NO: 7) (where X is a hydrophobic amino acid). Other conserved histidines include His 296 and His 303. Catalytically important histidines have been observed within the active site of several sulfatase crystal structures including human lysosomal N-acetylgalactosamine-4 sulfatase (arylsulfatase B) (Bond, C. S., Clements, P. R., Ashby, S. J., Collyer, C. A., Harrop, S. J., Hopwood, J. J., and Guss, J. M. (1997) *Structure* 5(2), 277-89) and arylsulfatase A (Lukatela, G., Krauss, N., Theis, K., Selmer, T., Gieselmann, V., von Figura, K., and Saenger, W. (1998) *Biochemistry* 37(11), 3654-64) as well as the arysulfatase from *Pseudomonas aeriginosa* (Boltes, I., Czapinska, H., Kahnert, A., von Bulow, R., Dierks, T., Schmidt, B., von Figura, K., Kertesz, M. A., and Uson, I. (2001) *Structure* (Camb) 9(6), 483-91) to which the flavobacterial 2-O sulfatase appears to be most closely related. In the latter case, His 211 appears to hydrogen bond with the sulfate oxygen (O4) contributing perhaps to proper sulfate coordination. Additionally, the Nδ1 of His 115 of *P. aeruginosa* (His 242 in the human 4-S sulfatase) is within hydrogen bonding distance to the Oγ2 of the catalytic formylglycine. The presence of His 136 in the active site and its participation in catalysis is strongly supported by our homology studies.

The flavobacterial 2-O sulfatase possesses 52 acidic amino acids, several of which are highly conserved (e.g., Asp 42, Asp 269, Asp 286, Asp 295, and Asp 342). Interestingly, four acidic side chains are also found in a consensus active site also observed in known crystal structures. In this snapshot, these four carboxylates appear to coordinate a divalent metal ion (typically calcium). This divalent metal in turn coordinates with the formylglycine hydroxylate and possibly the Oγ1 group of the sulfate.

Based on the understanding of the important residues involved in the function of 2-O sulfatase, the invention also embraces functional variants. As used herein, a "functional variant" of a 2-O sulfatase polypeptide is a polypeptide which contains one or more modifications to the primary amino acid sequence of a 2-O sulfatase polypeptide. The polypeptide can contain 1, 2, 3, 4, 5, 6, 7, 8, 9, 10, 11, 12, 13, 14, 15, 16, 17, 18, 19, 20, 25, 30, 35, 40, 50 or more amino acid modifications. These modifications are intended to encompass modifications that result in a 2-O sulfatase with altered activity relative to the native 2-O sulfatase but also include modifications that do not result in altered activity relative to the native enzyme. The term "native" as used herein refers to the 2-O sulfatase as it would be found in nature. Modifications which create a 2-O sulfatase polypeptide functional variant are typically made to the nucleic acid which encodes the 2-O sulfatase polypeptide, and can include deletions, point mutations, truncations, amino acid substitutions and addition of amino acids or non-amino acid moieties to: 1) enhance a property of a 2-O sulfatase polypeptide, such as protein stability in an expression system or the stability of protein-protein binding; 2) provide a novel activity or property to a 2-O sulfatase polypeptide, such as addition of a detectable moiety; or 3) to provide equivalent or better interaction with other molecules (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the 2-O sulfatase amino acid sequence. One of skill in the art will be familiar with methods for predicting the effect on protein conformation of a change in protein sequence, and can thus "design" a functional variant 2-O sulfatase polypeptide according to known methods. One example of such a method is described by Dahiyat and Mayo in Science 278:82-87, 1997, whereby proteins can be designed de novo. The method can be applied to a known protein to vary only a portion of the polypeptide sequence. By applying the computational methods of Dahiyat and Mayo, specific variants of a polypeptide can be proposed and tested to determine whether the variant retains a desired conformation.

Functional variants can include 2-O sulfatase polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a 2-O sulfatase polypeptide by eliminating proteolysis by proteases in an expression system (e.g., dibasic amino acid residues in yeast expression systems in which KEX2 protease activity is present). Functional variants, therefore, can also include variant 2-O sulfatase that maintain the same enzymatic function as the native 2-O sulfatase but include some modification to the amino acid sequence that does not alter native enzyme activity. These modifications include conservative amino acid substitutions as well as non-conservative amino acid substitutions that are remote from the binding and catalytic sites of the enzyme.

Mutations of a nucleic acid which encodes a 2-O sulfatase polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant 2-O sulfatase polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a 2-O sulfatase gene or cDNA clone to enhance expression of the polypeptide.

In the description that follows, reference will be made to the amino acid residues and residue positions of native 2-O sulfatase disclosed in SEQ ID NO: 1. In particular, residues and residue positions will be referred to as "corresponding to" a-particular residue or residue position of 2-O sulfatase. As will be obvious to one of ordinary skill in the art, these positions are relative and, therefore, insertions or deletions of one or more residues would have the effect of altering the numbering of downstream residues. In particular, N-terminal insertions or deletions would alter the numbering of all subsequent residues. Therefore, as used herein, a residue in a recombinant modified heparinase will be referred to as "corresponding to" a residue of the full 2-O sulfatase if, using standard sequence comparison programs, they would be aligned. Many such sequence alignment programs are now available to one of ordinary skill in the art and their use in sequence comparisons has become standard (e.g., "LALIGN" available via the Internet at http://phaedra.crbm.cnrs-mop.fr/fasta/lalign-query.html). As used herein, this convention of referring to the positions of residues of the recombinant modified heparinases by their corresponding 2-O sulfatase residues shall extend not only to embodiments including N-terminal insertions or deletions but also to internal insertions or deletions (e.g, insertions or deletions in "loop" regions).

One type of amino acid substitution is referred to as a "conservative substitution." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

Even when it is difficult to predict the exact effect of a substitution in advance of doing so, one skilled in the art will appreciate that the effect can be evaluated by routine screening assays, preferably the biological assays described herein. Modifications of peptide properties including thermal stability, enzymatic activity, hydrophobicity, susceptibility to proteolytic degradation or the tendency to aggregate with carriers or into multimers are assayed by methods well known to the ordinarily skilled artisan. For additional detailed description of protein chemistry and structure, see Schulz, G. E. et al., Principles of Protein Structure, Springer-Verlag, New York, 1979, and Creighton, T. E., Proteins: Structure and Molecular Principles, W. H. Freeman & Co., San Francisco, 1984.

Additionally, some of the amino acid substitutions are non-conservative substitutions. In certain embodiments where the substitution is remote from the active or binding sites, the non-conservative substitutions are easily tolerated provided that they preserve a tertiary structure characteristic of, or similar to, native 2-O sulfatase, thereby preserving the active and binding sites. Non-conservative substitutions, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain.

Nearly every active, recombinantly expressed sulfatase reported in the literature possesses a cysteine (and not a serine) within the active site sequence C/SXPXRXXXXS/TG (SEQ. ID NO: 6) (Lukatela, G., Krauss, N., Theis, K., Selmer, T., Gieselmann, V., von Figura, K., and Saenger, W. (1998) *Biochemistry* 37(11), 3654-64). It seemed likely, therefore, that a cysteine-specific modifying machinery functionally exists in *E. coli*. This idea was supported by our initial attempts to produce a recombinant cysteine→serine 2-O sulfatase variant which led to the production of insoluble protein when expressed in *E. coli*. We note that the *E. coli* genome encodes for at least three different putative sulfatase genes in addition to the atsB gene which, by homology, has been proposed to encode for this cysteine-specific modifying activity. All of these genes are located as a cluster within the bacterial chromosome (Kertesz, M. A. (2000) *FEMS Microbiol Rev* 24(2), 135-75). It would appear, however, that the *E. coli* sulfatase genes are normally cryptic. At the very least, *E. coli* lacks the specific enzymes for desulfating heparin/heparan sulfate glycosaminoglycans, but the bacterium fortuitously provides the necessary enzymology to effectively modify select heterologous sulfatases such as the 2-O sulfatase. Therefore, the 2-O sulfatases as described herein can be produced recombinantly in *E. coli*. However, the recombinant production of the 2-O sulfatases provided are not limited to their expression in *E. coli*. The 2-O sulfatases can also be recombinantly produced in other expression systems described below.

The 2-O sulfatases, can be recombinantly produced using a vector including a coding sequence operably joined to one or more regulatory sequences. As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5'regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria, in addition to *E. coli, Flavobacterium heparinum, Bacillus, Streptomyces, Pseudomonas, Salmonella, Serratia*, and the like.

To express the 2-O sulfatase of the invention in a prokaryotic cell, it is desirable to operably join the nucleic acid sequence of a 2-O sulfatase of the invention to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI and gal promoters of *E. coli*, the α-amylase (Ulmanen et al., *J. Bacteriol.* 162:176-182 (1985)) and the ζ-28-specific promoters of *B. subtilis* (Gilman et al., *Gene sequence* 32:11-20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468-478 (1986)).

Prokaryotic promoters are reviewed by Glick (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365-404 (1981)).

Because prokaryotic cells may not produce the 2-O sulfatase of the invention with normal eukaryotic glycosylation, expression of the 2-O sulfatase of the invention of the eukaryotic hosts is useful when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3×63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in *Drosophila* larvae. Using insect cells as hosts, the *Drosophila* alcohol dehydrogenase promoter can be used (Rubin, *Science* 240:1453-1459 (1988)). Alternatively, baculovirus vectors can be engineered to express large amounts of the 2-O sulfatase of the invention in insect cells (Jasny, *Science* 238:1653 (1987); Miller et al., In: *Genetic Engineering* (1986), Setlow, J. K., et al., eds., Plenum, Vol. 8, pp. 277-297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals that are temperature-sensitive so that by varying the temperature, expression can be repressed or initiated, or which are subject to chemical (such as metabolite) regulation.

As discussed above, expression of the 2-O sulfatase of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature (London)* 290:304-310 (1981)); the yeast gal4 gene sequence promoter (Johnston et al., *Proc. Natl. Acad. Sci. (USA)* 79:6971-6975 (1982); Silver et al., *Proc. Natl. Acad. Sci. (USA)* 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the 2-O sulfatase of the invention does not contain any intervening codons which are capable of encoding a methionine (i.e., AUG). The presence of such codons results either in the formation of a fusion protein (if the AUG codon is in the same reading frame as the 2-O sulfatase of the invention coding sequence) or a frame-shift mutation (if the AUG codon is not in the same reading frame as the 2-O sulfatase of the invention coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfection. Additional elements may also be needed for optimal synthesis of the 2-O sulfatase mRNA. These elements may include splice signals, as well as transcription promoters, enhancers, and termination signals. cDNA expression vectors incorporating such elements include those described by Okayama, *Molec. Cell. Biol.* 3:280 (1983).

In another embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, and πVX). Such plasmids are, for example, disclosed by Sambrook, et al. (*Molecular Cloning: A Laboratory Manual*, second edition, edited by Sambrook, Fritsch, & Maniatis, Cold Spring Harbor Laboratory, 1989)). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable Streptomyces plasmids include pIJ101 (Kendall et al., *J. Bacteriol.* 169:4177-4183 (1987)), and streptomyces bacteriophages such as φC31 (Chater et al., In: *Sixth International Symposium on Actinomycetales Biology*, Akademiai Kaido, Budapest, Hungary (1986), pp. 45-54). Pseudomonas plasmids are reviewed by John et al. (*Rev. Infect. Dis.* 8:693-704 (1986)), and Izaki (*Jpn. J. Bacteriol.* 33:729-742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265-274 (1982); Broach, In: *The Molecular Biology of the Yeast Saccharomyces. Life Cycle and Inheritance*, Cold Spring Harbor Laboratory, Cold Spring Harbor, N.Y., p. 445-470 (1981); Broach, *Cell* 28:203-204 (1982); Bollon et al., *J. Clin. Hematol. Oncol.* 10:39-48 (1980); Maniatis, In: *Cell Biology. A Comprehensive Treatise*, Vol. 3, Gene Sequence Expression, Academic Press, NY, pp. 563-608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. Additionally, DNA or RNA encoding the 2-O sulfatase of the invention may be directly injected into cells or may be impelled through cell membranes after being adhered to microparticles. After the introduction of the vector, recipient cells are grown in a selective medium, which selects for the growth of vector-containing cells. Expression of the cloned gene sequence(s) results in the production of the 2-O sulfatase of the invention. This can take place in the transformed cells as such, or following the induction of-these cells to differentiate (for example, by administration of bromodeoxyuracil to neuroblastoma cells or the like).

One of skill in the art may also substitute appropriate codons to produce the desired amino acid substitutions in SEQ ID NOs: 2 or 4 by standard site-directed mutagenesis techniques. One may also use any sequence which differs from the nucleic acid equivalents of SEQ ID NO: 2 or 4 only due to the degeneracy of the genetic code as the starting point for site directed mutagenesis. The mutated nucleic acid sequence may then be ligated into an appropriate expression vector and expressed in a host such as *E. coli*.

Figure 5A:
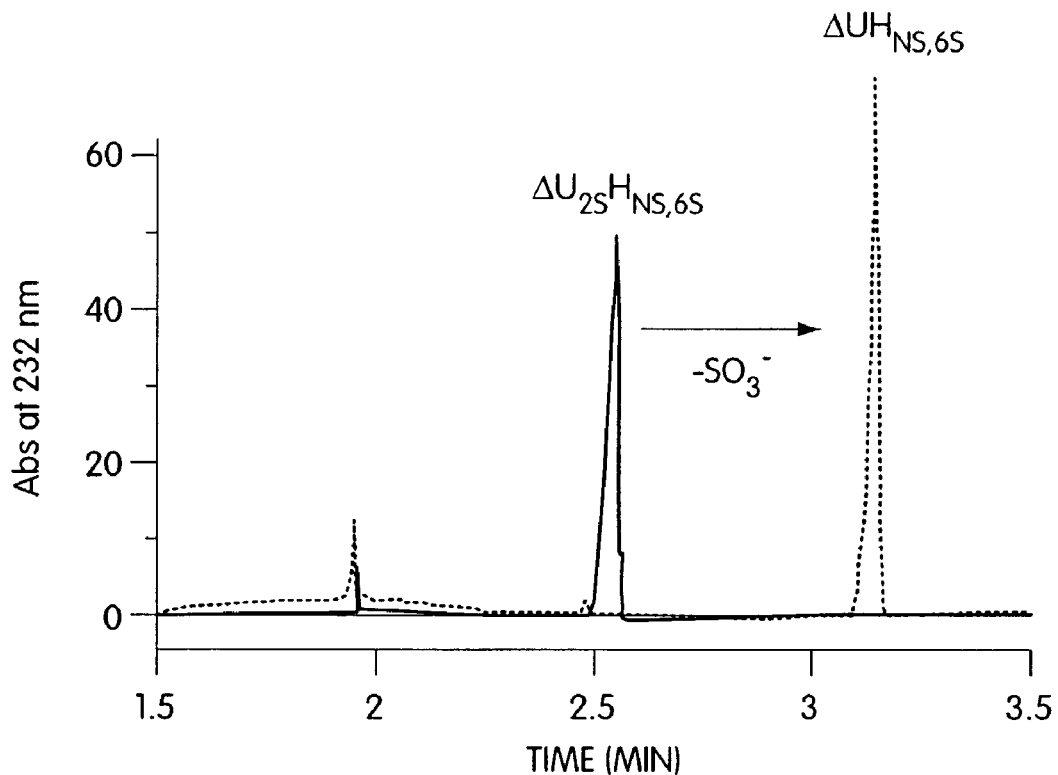
FIG. 5 illustrates the exclusive desulfation of the 2-OH position by the recombinant sulfatase. Panel (A) depicts the enzyme desulfating activity assayed by capillary electrophoresis using the 2-O containing trisulfated heparin disaccharide $\Delta U_{2S}H_{NS,6S}$. Panel (B) depicts the activity using its disulfated counterpart to $\Delta U_{2S}H_{NS,6S}$ lacking a sulfate at the 2-OH position. Only in Panel (A) is a loss of sulfate observed. Minus enzyme control is shown as a dotted line.
Figure 5B:
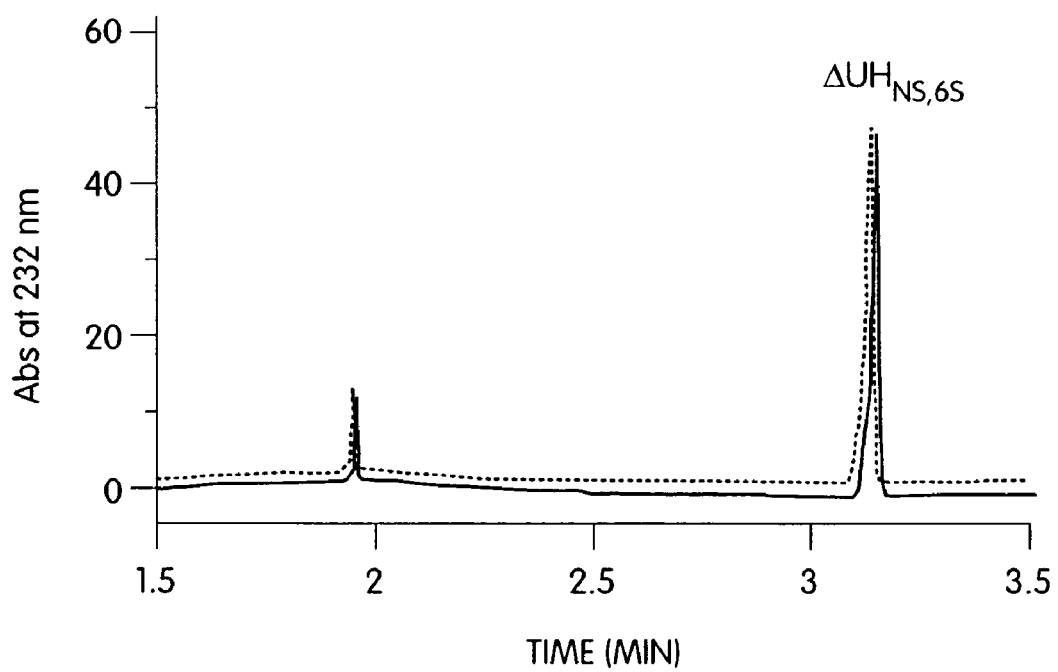

Our initial assessment of 2-O sulfatase activity was based upon the use of a few select unsaturated heparin disaccharide substrates. Desulfation was unequivocally specific for the 2-O position (FIG. 5). This substrate discrimination was based on the extent of sulfation and largely manifested as a $K_m$ effect. In particular, the presence of a 6-0 sulfate on the adjoining glucosamine conferred a significantly lower $K_m$ relative to its counterpart lacking such a sulfate ester. In terms of catalytic efficiency, the trisulfated disaccharide ($\Delta U_{2S} H_{NS,6S}$) was the more efficient substrate whereas the monosulfated disaccharide ($\Delta U_{2S} H_{NAc}$) was less efficient.

The 2-O sulfated chondroitin disaccharide $\Delta U_{2S} Gal_{NAc,6S}$, however, was also, albeit negligibly, hydrolyzed under the same kinetic conditions. The enzyme did desulfate this disaccharide to an appreciable extent, however, under reaction conditions involving a 4× higher enzyme concentration and a longer incubation time. Under these conditions, approximately 40% of the substrate was desulfated over a 20 minute period. In contrast, less than 10% of chondroitin disaccharide $\Delta U_{2S}Gal_{NAc,4S}$ was hydrolyzed during the same time period. Under exhaustive conditions, both chondroitin disaccharides were greater than 95% desulfated at the 2-O position. The apparent kinetic discrimination points to an underlying structural determinant, namely a preference for glucosamine sulfated at the 6-OH and 2N positions.

Figure 6A:
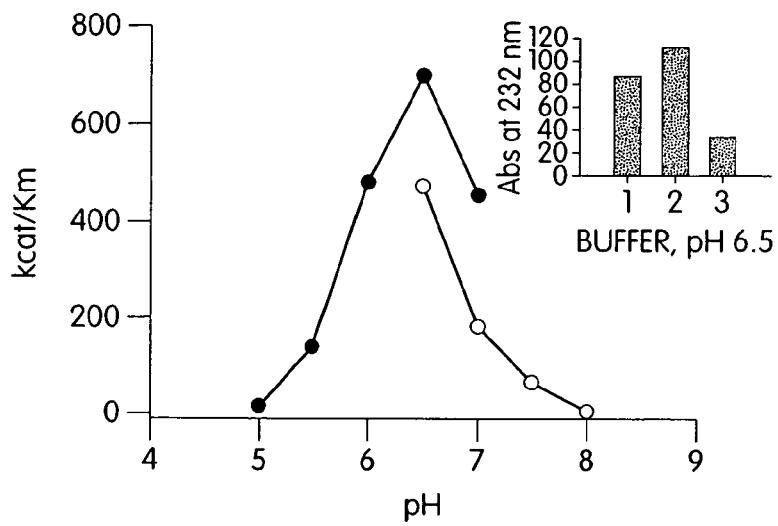
FIG. 6 provides the in vitro biochemical reaction conditions for the recombinant 2-O sulfatase. Panel (A) illustrates the effect of pH. Sulfatase catalytic efficiency ($k_{cat}/K_m$) was measured as a function of varying pH from 5 to 8 using two overlapping buffers: 50 mM MES (solid circles) and 50 mM MOPS (open circles). Inset: Relative effect of three different assay buffers (each at pH 6.5) on optimal enzyme activity. 1. 50 mM MES; 2. 50 mM imidazole; 3. 50 mM sodium phosphate. Panel (B) illustrates the effect of ionic strength. Shown here is % activity normalized to 50 mM NaCl. Panel (C) illustrates the effect of reaction temperature. Data is normalized to 30° C. activity (100%). The unsaturated disaccharide $\Delta U_{2S}H_{NS}$ was used in all three experiments.
Figure 6B:
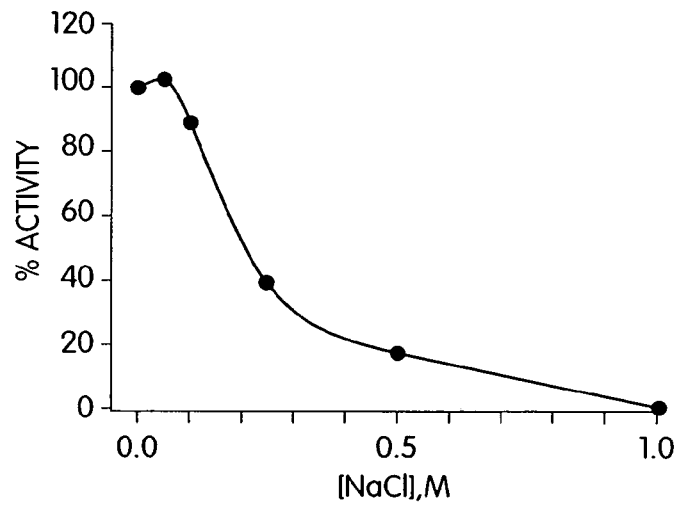
Figure 6C:
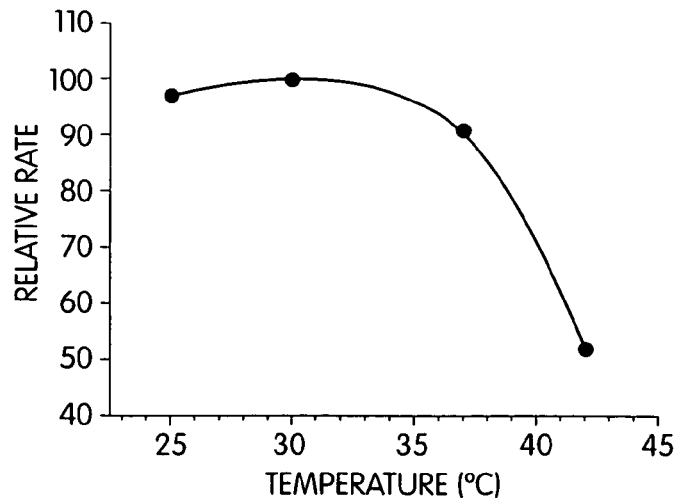

In addition, examination of the biochemical conditions for optimal enzymatic activity yielded several observations. First, 2-O sulfatase activity exhibited a pH profile with a narrower pH range (6.0-7.0) in which the enzyme was most active. The enzyme exhibited maximal catalytic efficiency at pH 6.5 with essentially no activity observed at the outlying pH values of 5 and 8 (FIG. 6, Panel (A)). A sharply defined pH optima of 6.5 implicates a catalytic role of one or more histidines. Second, the observed NaCl titration profile (FIG. 6, Panel (B)) demonstrates a clearly inhibitory effect of ionic strength on sulfatase activity, even at relatively low NaCl concentrations. That is, while 50% inhibition occurred in the presence of approximately 200 mM NaCl, even 100 mM NaCl was slightly inhibitory to 2-O sulfatase activity. This is a rather sharp activity transition for both the Δ 4,5 glycuronidase and other recombinantly expressed F. heparinum GAG degrading enzymes. The correlation between activity and the ionic buffer composition is reasonable, given the anionic character of the saccharide substrates conferred by both the presence of sulfates and the uronic acid carboxylates within each disaccharide unit. For the 2-O sulfatase in particular, charge interactions between basic side chains and the sulfate oxygen anion may be involved in substrate orientation.

The results described herein suggest that the 2-O sulfatase activity is upstream from the hydrolysis of the unsaturated uronic acid by the Δ 4,5 glycuronidase. This scenario would also make the 2-O sulfatase a so-called "early" enzyme in the HSGAG degradation pathway that occurs in vivo. The substrate-product correlation between the 2-O sulfatase and the Δ 4,5 glycuronidase has been demonstrated with the two experiments summarized in FIGS. 7 and 8. FIG. 8 in particular demonstrates how these two enzymes (along with the heparinases) can be used in tandem as analytical tools for HSGAG compositional analyses. The results have demonstrated the utility of the sulfatase as a tool for probing HSGAG composition, especially when the enzyme is used in tandem with the Δ 4,5 glycuronidase.

The present invention provides for the use of 2-O sulfatase as an enzymatic tool due to its substrate specificity and specific activity. As described herein, it was found that the activity of the cloned enzyme is not compromised by its recombinant expression in E. coli. The "native 2-O sulfatase specific activity" is the measure of enzymatic activity of the native 2-O sulfatase obtained from cell lysates of F. heparinum also described in the Examples below. Therefore, based on the disclosure provided herein, those of ordinary skill in the art will be able to identify other 2-O sulfatases having altered enzymatic activity with respect to the native 2-O sulfatase such as functional variants.

The term "specific activity" as used herein refers to the enzymatic activity of a preparation of 2-O sulfatase. In general, it is preferred that the substantially pure and/or isolated 2-O sulfatase preparations of the invention have a specific activity of at least about 7 nanomoles of substrate (DiS) hydrolyzed per minute per microgram of enzyme. It also generally more preferred that the substantially pure and/or isolated 2-O sulfatase preparations of the invention have a specific activity of at least about 40 nanomoles of substrate (DiS) hydrolyzed per minute per microgram of enzyme. As provided herein, the recombinant 2-O sulfatase purified by (nickel chromatography with the histidine tag) was found to have an about six-fold higher specific activity than native 2-O sulfatase. The recombinant 2-O sulfatase without the histidine tag was found to have an about ten-fold higher specific activity than the native 2-O sulfatase. Therefore, in one aspect of the invention preparations of 2-O sulfatase with about a 5-, 6-, 7-, 8-, 9-, 10-, 11-, 12-, 13-, 14-, 15-, 20-, 25-, and 30-fold specific activity are provided.

The invention, therefore, provides for the degradation of glycosaminoglycans using the 2-O sulfatase described herein. The 2-O sulfatase of the invention may be used to specifically degrade an HSGAG by contacting the HSGAG substrate with the 2-O sulfatase of the invention. The invention is useful in a variety of in vitro, in vivo and ex vivo methods in which it is useful to degrade HSGAGs.

As used herein the terms "HSGAG" and "glycosaminoglycan" and "GAG" are used interchangeably to refer to a family of molecules having heparin-like/heparan sulfate-like structures and properties. These molecules include but are not limited to low molecular weight heparin (LMWH), heparin, biotechnologically prepared heparin, chemically modified heparin, synthetic heparin, and heparan sulfate. The term "biotechnological heparin" encompasses heparin that is prepared from natural sources of polysaccharides which have been chemically modified and is described for example in Razi et al., Bioche. J. Jul. 15, 1995;309 (Pt 2): 465-72. Chemically modified heparin is described in Yates et al., Carbohydrate Res (1996) November 20;294:15-27, and is known to those of skill in the art. Synthetic heparin is well known to those of skill in the art and is described in Petitou, M. et al., Bioorg Med Chem Lett. (1999) April 19;9(8):1161-6.

Analysis of a sample of glycosaminoglycans is also possible with 2-O sulfatase alone or in conjunction with other enzymes. Other HSGAG degrading enzymes include but are not limited to heparinase-I, heparinase-II, heparinase-III, Δ 4, 5 glycuronidase, other sulfatases, modified versions of the enzymes, variants and functionally active fragments thereof. In particular, 2-O sulfatase can be used subsequent to or concomitantly with a heparinase to degrade a glycosaminoglycan. In addition 2-O sulfatase may be used prior to and also concomitantly with Δ 4, 5 glycuronidase.

The methods that may be used to test the specific activity of 2-O sulfatase of the present invention are known in the art, e.g., those described in the Examples. These methods may also be used to assess the function of variants and functionally active fragments of 2-O sulfatase. The $k_{cat}$ value may be determined using any enzymatic activity assay to assess the activity of a 2-O sulfatase enzyme. Several such assays are well-known in the art. For instance, an assay for measuring $k_{cat}$ is described in Ernst, S. E., Venkataraman, G., Winkler, S., Godavarti, R., Langer, R., Cooney, C. and Sasisekharan. R. (1996) Biochem. J. 315, 589-597. Therefore, based on the disclosure provided herein, those of ordinary skill in the art will be able to identify other 2-O sulfatase molecules having enzymatic activity that is similar to or altered in comparison with the native 2-O sulfatase molecule such as 2-O sulfatase functional variants.

Due to the activity of 2-O sulfatase on glycosaminoglycans, the product profile produced by a 2-O sulfatase may be determined by any method known in the art for examining the type or quantity of degradation products produced by 2-O sulfatase alone or in combination with other enzymes. One of skill in the art will also recognize that the 2-O sulfatase may also be used to assess the purity of glycosaminoglycans in a sample. One preferred method for determining the type and quantity of product is described in Rhomberg, A. J. et al., *PNAS*, v. 95, p. 4176-4181, (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase to degrade HSGAGs to produce HSGAG oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative. Detailed methods for sequencing polysaccharides and other polymers are disclosed in co-pending U.S. patent applications Ser. Nos. 09/557,997 and 09/558,137, both filed on Apr. 24, 2000 and having common inventorship. The entire contents of both applications are hereby incorporated by reference.

Briefly, the method is performed by enzymatic digestion, followed by mass spectrometry and capillary electrophoresis. The enzymatic assays can be performed in a variety of manners, as long as the assays are performed identically on the HSGAG, so that the results may be compared. In the example described in the Rhomberg reference, enzymatic reactions are performed by adding 1 mL of enzyme solution to 5 mL of substrate solution. The digestion is then carried out at room temperature (22° C.), and the reaction is stopped at various time points by removing 0.5 mL of the reaction mixture and adding it to 4.5 mL of a MALDI matrix solution, such as caffeic acid (approximately 12 mg/mL) and 70% acetonitrile/water. The reaction mixture is then subjected to MALDI mass spectrometry. The MALDI surface is prepared by the method of Xiang and Beavis (Xiang and Beavis (1994) *Rapid. Commun. Mass. Spectrom.* 8, 199-204). A two-fold lower access of basic peptide $(Arg/Gly)_{15}$ is premixed with matrix before being added to the oligosaccharide solution. A 1 mL aliquot of sample/matrix mixture containing 1-3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra may be calibrated externally by using the signals for proteinated $(Arg/Gly)_{15}$ and its complex with the oligosaccharide.

Capillary electrophoresis may then be performed on a Hewlett-Packard$^3$D CE unit by using uncoated fused silica capillaries (internal diameter 75 micrometers, outer diameter 363 micrometers, $1_{det}$ 72.1 cm, and $1_{tot}$ 85 cm). Analytes are monitored by using UV detection at 230 nm and an extended light path cell (Hewlett-Packard). The electrolyte is a solution of 10 mL dextran sulfate and 50 millimolar Tris/phosphoric acid (pH2.5). Dextran sulfate is used to suppress nonspecific interactions of the heparin oligosaccharides with a silica wall. Separations are carried out at 30 kV with the anode at the detector side (reversed polarity). A mixture of a 1/5-naphtalenedisulfonic acid and 2-naphtalenesulfonic acid (10 micromolar each) is used as an internal standard.

Other methods for assessing the product profile may also be utilized. For instance, other methods include methods which rely on parameters such as viscosity (Jandik, K. A., Gu, K. and Linhardt, R. J., (1994), *Glycobiology*, 4:284-296) or total UV absorbance (Ernst, S. et al., (1996), *Biochem. J.*, 315:589-597) or mass spectrometry or capillary electrophoresis alone.

The 2-O sulfatase molecules of the invention are also useful as tools for sequencing HSGAGs. Detailed methods for sequencing polysaccharides and other polymers are disclosed in co-pending U.S. patent applications Ser. Nos. 09/557,997 and 09/558,137, both filed on Apr. 24, 2000 and having common inventorship. These methods utilize tools such as heparinases in the sequencing process. The 2-O sulfatase of the invention is useful as such a tool.

2-O sulfatase as well as the combinations of 2-O sulfatase with other enzymes can, therefore, be used in any method of analyzing HSGAGs. In addition, these enzymes as described can be used to determine the presence of a particular glycosaminoglycan in a sample or the composition of a glycosaminoglycans in a sample. A "sample", as used herein, refers to any sample that may contain a GAG.

One of ordinary skill in the art, in light of the present disclosure, is enabled to produce substantially pure preparations of HSGAG and/or GAG fragment compositions utilizing the 2-O sulfatase molecules alone or in conjunction with other enzymes. The GAG fragment preparations are prepared from HSGAG sources. A "HSGAG source" as used herein refers to heparin-like/heparan sulfate-like glycosaminoglycan composition which can be manipulated to produce GAG fragments using standard technology, including enzymatic degradation etc. As described above, HSGAGs include but are not limited to isolated heparin, chemically modified heparin, biotechnology prepared heparin, synthetic heparin, heparan sulfate, and LMWH. Thus HSGAGs can be isolated from natural sources, prepared by direct synthesis, mutagenesis, etc.

The 2-O sulfatase is, in some embodiments, immobilized on a support. The 2-O sulfatase may be immobilized to any type of support but if the support is to be used in vivo or ex vivo it is desired that the support is sterile and biocompatible. A biocompatible support is one which would not cause an immune or other type of damaging reaction when used in a subject. The 2-O sulfatase may be immobilized by any method known in the art. Many methods are known for immobilizing proteins to supports. A "solid support",as used herein refers to any solid material to which a polypeptide can be immobilized.

Solid supports, for example, include but are not limited to membranes, e.g., natural and modified celluloses such as nitrocellulose or nylon, Sepharose, Agarose, glass, polystyrene, polypropylene, polyethylene, dextran, amylases, polyacrylamides, polyvinylidene difluoride, other agaroses, and magnetite, including magnetic beads. The carrier can be totally insoluble or partially soluble and may have any possible structural configuration. Thus, the support may be spherical, as in a bead, or cylindrical, as in the inside surface of a test tube or microplate well, or the external surface of a rod. Alternatively, the surface may be flat such as a sheet, test strip, bottom surface of a microplate well, etc.

The 2-O sulfatase of the invention may also be used to remove active GAGs from a GAG containing fluid. A GAG containing fluid is contacted with the 2-O sulfatase of the invention to degrade the GAG. The method is particularly useful for the ex vivo removal of GAGs from blood. In one embodiment of the invention the 2-O sulfatase is immobilized on a solid support as is conventional in the art. The solid support containing the immobilized 2-O sulfatase may be used in extracorporeal medical devices (e.g. hemodialyzer, pump-oxygenator) for systemic heparinization to prevent the blood in the device from clotting. The support membrane containing immobilized 2-O sulfatase is positioned at the end of the device to neutralize the GAG before the blood is returned to the body.

2-O sulfatase and the resulting GAG fragments also have many therapeutic utilities. A "therapeutic GAG fragment" as used herein refers to a molecule or molecules which are degraded GAGs or pieces or fragments thereof that have been degraded through the use of the 2-O sulfatase possibly along with other GAG—degrading enzymes, (e.g. native and/or modified heparinases). Such compounds may be generated using 2-O sulfatase to produce therapeutic fragments or they may be synthesized de novo. Putative GAG fragments can be tested for therapeutic activity using any of the assays described herein or known in the art. Thus the therapeutic GAG fragment may be a synthetic GAG fragment generated based on the sequence of the GAG fragment identified when the tumor is contacted with 2-O sulfatase, or having minor variations which do not interfere with the activity of the compound. Alternatively the therapeutic GAG fragment may be an isolated GAG fragment produced when the tumor is contacted with 2-O sulfatase.

The 2-O sulfatase and/or GAG fragments can be used for the treatment of any type of condition in which GAG fragment therapy has been identified as a useful therapy, such as preventing coagulation, inhibiting angiogenesis, preventing neovascularization, inhibiting proliferation, regulating apoptosis, etc. The methods of the invention also enable one of skill in the art to prepare or identify an appropriate composition of GAG fragments, depending on the subject and the disorder being treated. These compositions of GAG fragments may be used alone or in combination with the 2-O sulfatase and/or other enzymes. Likewise 2-O sulfatase and/or other enzymes may also be used to produce GAG fragments in vivo.

The invention is useful for treating and/or preventing any disease/condition in a subject whereby glycosaminoglycans have been found to be important in the development and/or progress of the disease. The terms "treat" and "treating" as used herein refers to reversing or blocking the progression of the disease in the subject. Treating a disease also includes exacting a desired improvement in the disease or symptoms of the disease. For example to treat a subject with tumor cell proliferation refers to inhibiting completely or partially the proliferation or metastasis of a cancer or tumor cell, as well as inhibiting or preventing any increase in the proliferation or metastasis of a cancer or tumor cell.

A "subject having a disease" is a subject that can be diagnosed as having the disease, e.g., a person having cancer is identified by the presence of cancerous cells. A "subject at risk of having a disease" as used herein is a subject who has a high probability of developing the disease. These subjects include, for instance, subjects having a genetic abnormality, the presence of which has been demonstrated to have a correlative relation to a higher likelihood of developing the disease. For diseases brought about by exposure to disease causing agents, subjects at risk are those who are exposed to the disease causing agents such as tobacco, asbestos, chemical toxins, viruses, parasites, etc. A subject at risk also includes those who have previously been treated for the disease and have the possibility of having a recurrence of the disease. When a subject at risk of developing a disease is treated with a 2-O sulfatase, a cocktail of 2-O sulfatase along with other GAG—degrading enzymes (e.g. heparinase and Δ4, 5 glycuronidase) or degradation products thereof the subject is able to prevent the occurrence of the disease or reduce the possibility of developing the disease.

The compositions of the invention, therefore, can be used for the treatment of any type of condition in which GAG fragment therapy has been identified as a useful therapy. Thus, the invention is useful in a variety of in vitro, in vivo and ex vivo methods in which therapies are useful. For instance, GAG fragments can also be useful for treating or preventing cancer, atherosclerosis, neurodegenerative disease (e.g. Alzheimer's), microbial infection, psoriasis, etc. GAG fragments can also be useful in tissue repair. The GAG fragment compositions may also be used in in vitro assays, such as a quality control sample.

Each of these disorders mentioned herein is well-known in the art and is described, for instance, in *Harrison's Principles of Internal Medicine* (McGraw Hill, Inc., New York), which is incorporated by reference.

In one embodiment the preparations of the invention are used for inhibiting angiogenesis. An effective amount for inhibiting angiogenesis of the GAG fragment preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of GAG fragment preparation which is sufficient to diminish the number of blood vessels growing into a tumor. This amount can be assessed in an animal model of tumors and angiogenesis, many of which are known in the art.

Thus, the 2-O sulfatase molecules are useful for treating or preventing disorders associated with coagulation. A "disease associated with coagulation" as used herein refers to a condition characterized by an interruption in the blood supply to a tissue due to a blockage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

A "disease associated with coagulation" as used herein also is intended to encompass atherosclerosis. Atherosclerosis is a disease of the arteries whereby blood flow can be reduced due to the development of atheromatous plaques along the interior walls of the arteries. These plaques begin by the initial deposition of cholesterol crystals which grow larger with time. In addition to the cholesterol deposition, plaques also grow due to the proliferation of the surrounding cells. In time, the artery may become completely occluded due to this plaque growth.

The 2-O sulfatase or the GAG fragments generated therewith may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol;* v. 25 (7 supp), p. 18S-22S (1995); Holmes, et al, *J Am Coll Cardiol;* v.25 (7 suppl), p. 10S-17S (1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428-435 (1988) and its modified form described by Bennett, W. F. et al., 1991, *J. Biol. Chem.* 266(8):5191-5201, the entire contents of which are hereby incorporated by reference.

The compositions as described herein can also be used to prevent or treat "neurodegenerative disease" is defined herein as a disease in which progressive loss of neurons occurs either in the peripheral nervous system or in the central nervous system. Examples of neurodegenerative disorders include familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS dementia, age related dementia, age associated memory impairment, amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, bovine spongiform encephalopathy and kuru), and those caused by excess cystatin C accumulation (hereditary cystatin C angiopathy), traumatic brain injury (e.g., surgery-related brain injury), cerebral edema, peripheral nerve damage, spinal cord injury, Wernicke-Korsakoff's related dementia (alcohol induced dementia), and presenile dementia. The foregoing examples are not meant to, be comprehensive but serve merely as an illustration of the term "neurodegenerative disease".

The invention also provides treatment or prevention of a neurodegenerative disease by the administration of the 2-O sulfatase and/or GAG fragment compositions described herein possibly in conjunction with other therapeutic agents for the particular condition being treated. The administration the other therapeutics may be performed concomitantly, sequentially or at different time points.

For example, when treating Alzheimer's Disease, the therapeutic agents which can be combined with the compositions of the invention include, but are not limited to, estrogen, vitamin E (alpha-tocopherol), Tacrine (tetrahydroacridinamine), selegiline (deprenyl), and Aracept (donepezil). One of ordinary skill in the art will be familiar with additional therapeutic agents useful for the treatment of neurodegenerative diseases.

Critically, HSGAGs (along with collagen) are key components of the cell surface-extracellular matrix (ECM) interface. While collagen-like proteins provide the necessary extracellular scaffold for cells to attach and form tissues, the complex polysaccharides fill the space created by the scaffold and act as a molecular sponge by specifically binding and regulating the biological activities of numerous signaling molecules like growth factors, cytokines etc. Therefore, the compositions provided herein can also be used in methods of repairing tissues.

In addition, as it had been found that viruses and parasites utilize glycosaminoglycans such as heparan sulfate as receptors to infect target cells (Liu, J., and Thorp, S. C. (2002) *Med Res Rev* 22(1), 1-25), the compositions of the invention may also be used to treat or prevent microbial infections. The compositions of the invention can also be administered in combination with other antiviral agents or antiparasitic agents.

Antiviral agents are compounds which prevent infection of cells by viruses or replication of the virus within the cell. There are several stages within the process of viral infection which can be blocked or inhibited by antiviral agents. These stages include, attachment of the virus to the host cell (immunoglobulin or binding peptides), uncoating of the virus (e.g., amantadine), synthesis or translation of viral mRNA (e.g., interferon), replication of viral RNA or DNA (e.g., nucleoside analogues), maturation of new virus proteins (e.g., protease inhibitors), and budding and release of the virus.

Examples of antiviral agents known in the art are nucleotide analogues which include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

It has also been recently been recognized that cells synthesize distinct HSGAG sequences and decorate themselves with these sequences, using the extraordinary information content present in the sequences to bind specifically to many signaling molecules and thereby regulate various biological processes. The processes include apoptosis (Ishikawa, Y., and Kitamura, M. (1999) *Kidney Int* 56(3), 954-63, Kapila, Y. L., Wang, S., Dazin, P., Tafolla, E., and Mass, M. J. (2002) *J Biol Chem* 277(10), 8482-91). Regulation of apoptosis with the compositions of the invention can prove important to a variety of diseases whereby an increase or decrease in cell death is warranted. Apoptosis is known to play a role in- numerous physiologic and pathological events such as embryogenesis and metamorphosis, hormone-dependent involution in the adult, cell death in tumors, atrophy of some organs and tissues, etc.

As the compositions of the invention are useful for the same purposes as heparinases and the degradation products of heparinases (HSGAG fragments), they are also useful for treating and preventing cancer cell proliferation and metastasis. Thus, according to another aspect of the invention, there is provided methods for treating subjects having or at risk of having cancer. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

The invention also encompasses screening assays for identifying therapeutic GAG fragments for the treatment of a tumor and for preventing metastasis. The assays are accomplished by treating a tumor or isolated tumor cells with 2-O sulfatase and/or other native or modified heparinases and isolating the resultant GAG fragments. Surprisingly, these GAG fragments have therapeutic activity in the prevention of tumor cell proliferation and metastasis. Thus the invention encompasses individualized therapies, in which a tumor or portion of a tumor is isolated from a subject and used to prepare the therapeutic GAG fragments. These therapeutic fragments can be re-administered to the subject to protect the subject from further tumor cell proliferation or metastasis or from the initiation of metastasis if the tumor is not yet metastatic. Alternatively the fragments can be used in a different subject having the same type or tumor or a different type of tumor.

The invasion and metastasis of cancer is a complex process which involves changes in cell adhesion properties which allow a transformed cell to invade and migrate through the extracellular matrix (ECM) and acquire anchorage-independent growth properties (Liotta, L. A., et al., Cell 64:327-336, 1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the 2-O sulfatase compositions or degradation products thereof can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer, 1992, 52:378-383. Matrigel is a reconstituted basement membrane containing type IV collagen, laminin, heparan sulfate proteoglycans such as perlecan, which bind to and localize bFGF, vitronectin as well as transforming growth factor-β (TGF-β), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

Effective amounts of the 2-O sulfatase, functional variants thereof or therapeutic GAGs of the invention are administered to subjects in need of such treatment. Effective amounts are those amounts which will result in a desired improvement in the condition or symptoms of the condition, e.g., for cancer this is a reduction in cellular proliferation or metastasis, without causing other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise 2-O sulfatase, functional variants thereof or therapeutic GAG fragments together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the 2-O sulfatase of the present invention or other compositions, and with each other, in a manner such that there is no interaction which would substantially impair the desired pharmaceutical efficiency.

A variety of administration routes are available. The particular mode selected will depend, of course, upon the particular active agent selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. A preferred mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The compositions may conveniently be presented in unit dosage form and may be prepared by any of the methods well known in the art of pharmacy. All methods include the step of bringing the active 2-O sulfatase into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The compositions may be stored lyophilized.

Other delivery systems can include time-release, delayed release or sustained release delivery systems. Such systems can avoid repeated administrations of the heparinases of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

A subject is any human or non-human vertebrate, e.g., dog, cat, horse, cow, pig.

When administered to a patient undergoing cancer treatment, the 2-O sulfatase or therapeutic GAG compounds may be administered in cocktails containing other anti-cancer agents. The compounds may also be administered in cocktails containing agents that treat the side-effects of radiation therapy, such as anti-emetics, radiation protectants, etc.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-nl; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The 2-O sulfatase or therapeutic GAG compounds may also be linked to a targeting molecule. A targeting molecule is any molecule or compound which is specific for a particular cell or tissue and which can be used to direct the 2-O sulfatase or therapeutic GAG to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

Tumor-antigens include Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

The present invention is further illustrated by the following Examples, which in no way should be construed as further limiting. The entire contents of all of the references (includ-

EXAMPLES

Materials And Methods

Reagents—Heparin and chondroitin disaccaharides were purchased from Calbiochem (La Jolla, Calif.). Unfractionated heparin was obtained from Celsus Laboratories (Cincinatti, Ohio). The unsaturated heparin tetrasaccharide $\Delta U_{2S}H_{NS,6S}I_{2S}H_{NS,6S}$ (T1) and decasaccharide $\Delta U_{2S}H_{NS,6S}I_{2S}H_{NS,6S}I_{2S}H_{NS,6S}IH_{NAc,6S}GH_{NS,3S,6S}$ (AT-10) were generated by a partial heparinase digestion and purified as described (Toida, T., Hileman, R. E., Smith, A. E., Vlahova, P. I., and Linhardt, R. J. (1996) *J Biol Chem* 271(50), 32040-7). Materials for λZAP II genomic library construction, screening and phagemid excision including bacteriophage host strain XL1Blue MRF and the helper-resistant strain SOLR were obtained from Stratagene (La Jolla, Calif.) and used according to the Manufacturer's instructions. Restriction endonucleases and molecular cloning and PCR enzymes were purchased from New England Biolabs (Beverly, Mass.). DNA oligonucleotide primers were synthesized by Invitrogen/Life Technologies custom primer service (Carlisbad, Calif.). TOP10 chemically competent cells for PCR cloning and subcloning were also obtained from Invitrogen. [$^{32}$P] dCTP radionuclides were purchased from NEN (Boston, Mass.). Additional molecular cloning reagents were obtained from the manufacturers listed. Modified trypsin (sequencing grade) was purchased from Roche Molecular Biochemicals (Indianapolis, Ind.). Texas Red hydrazine was purchased from Molecular Probes (Eugene, Oreg.). All other reagents were from Sigma-Aldrich (St. Louis, Mo.) unless otherwise noted.

Purification of the Flavobacterium heparinum 2-O sulfatase and subsequent proteolysis—The 2-O sulfatase was purified from 20 liter fermentation cultures. Briefly, the large-scale cultures were grown at 25° C. for 48 hours. Cell lysates were obtained by a repeated passage of a resuspended cell pellet through an Aminco French-pressure cell. The homogenate was clarified by centrifugation (37000×g). The 2-O sulfatase was purified from this cell-free supernatant by employing five chromatographic steps carried out in the following sequence: cation-exchange (CM-Sepaharose CL-6B)→hydroxyapatite (Bio-Gel HTP)→gel filtration (Sephadex G-50)→taurine-Sepharose CL-4B→blue-Sepharose CL-6B. 2-O sulfatase activity was measured at each chromatography step as described (McLean, M. W., Bruce, J. S., Long, W. F., and Williamson, F. B. (1984) *Eur J Biochem* 145(3), 607-15). Fractions from 6 initial CM-sepharose chromatography were also assayed for heparinase, chondroitinase (AC and B) and Δ 4,5 glycuronidase activities as well as any co-eluting 6-O or N sulfatase activities. The highly purified 2-O sulfatase pool from the final blue-Sepharose chromatography step was free from any contaminating glycosaminoglycan degrading activity.

Generation of 2-O sulfatase peptides and protein sequencing—In preparation for proteolysis, the purified flavobacterial sulfatase was first desalted by reverse phase chromatography (RP-HPLC) on a 150 mm×4.6 mm C4 column (Phenomenex, Torrance, Calif.). Protein was eluted by applying a linear gradient from 0-80% acetonitrile in 0.1% TFA. During this elution, both a major and minor protein peak was detected by UV absorbance at 210 nm and 277 nm (FIG. 1 Panel (A)). The two separate fractions were lyophilized to dryness and resuspended in 50 µL of denaturation buffer (8M Urea, 0.4 M ammonium bicarbonate, pH 7.5). Both protein fractions were digested with modified trypsin for approximately 18 hours at 37° C. Trypsin was added at a 1:40 ratio (w/w) relative to each sulfatase fraction. Prior to proteolysis, cysteines were first subjected to reductive carboxymethylation by the addition of 5 mM dithiothreitol for 1 hour at 50° C., followed by the addition of 20 mM iodoacetic acid for 30 minutes (room temperature). The alkylation reaction was quenched by the addition of 50 µL denaturation buffer. The resulting peptides were resolved by RP-HPLC on a 250 mm×2 mm C4 column using a linear gradient of 2-80% acetonitrile in 0.1% trifluoracetic acid carried out over a 120 minute timecourse. Select peptides corresponding to chromatography peaks 2, 3, 4, 5, and 8 (FIG. 1 Panel (B)) were sequenced using an on-line Model 120 phenylthiohydantoin-derivative analyzer (Biopolymers Laboratory, Massachusetts Institute of Technology).

Molecular cloning of the flavobacterial 2-O sulfatase—The 2-O sulfatase was cloned from a λZAP II flavobacterial genomic library constructed and screened essentially as described for the Δ 4,5 glycuronidase (Myette, J. R., Shriver, Z., Kiziltepe, T., McLean, M. W., Venkataraman, G., and Sasisekharan, R. (2002) *Biochemistry* 41(23), 7424-7434). A 600 base pair DNA plaque hybridization probe was generated by PCR using degenerate primers 5' ATHGAYATHATHC-CNACNATH 3' (forward, SEQ ID NO: 8) and 5' DATNG-TYTCATTNCCRTGYTG 3' (reverse, SEQ ID NO: 9). PCR was carried out for 35 cycles using a 52° C. annealing temperature and 2 minute extensions at 72° C. The specificity of this probe was established by DNA sequence analysis, which indicated a direct correspondence of its translated sequence to peak 1 tryptic peptides. Based on this information, the non-degenerate primers 5' CATACACGTATGGGCGATTAT 3' (forward, SEQ ID NO: 10) and 5' GATGTGGGGATGAT-GTCGAT 3' (reverse, SEQ ID NO: 11) were subsequently used in place of the original degenerate primers. PCR amplified DNA probe was gel purified and subsequently $^{32}$P radio-labeled using the Prime-it II random priming kit (Stratagene). Plaques were lifted on to nylon membranes (Nytran Super-charge, Schleicher and Schuell, Keene, N.H.) and DNA was crosslinked to each filter by UV-irradiation. Plaque hybridizations were completed overnight at 42° C. according to standard methods and solutions (*Current Protocols in Molecular Biology* (1987) (Ausubel, F. M., Brent, R., Kingston, R. E., Moore, D. D., Seidman, J. G., Smith, J. A., and Struhl, K., Ed.) 1-3 vols., John Wiley and Sons, New York). Positive clones were visualized by phosphor imaging (Molecular Dynamics, Piscataway, N.J.) and/or $^{32}$P autoradiography. Clones were further purified by secondary and tertiary screens and the recombinant phage was excised as a double-stranded phagemid (pBluescript) as described by the manufacturer (Stratagene). Recombinants were confirmed by DNA sequencing using both T7 and T3 primers. Insert size was determined by restriction mapping of pBluescript inserts using Not 1, Xba 1, and Xho 1.

The full-length sulfatase gene (phagemid clone S4A) was subcloned into the T7-based expression plasmid pET28a in three steps. In the first PCR step, Nde 1 and Xho 1 restriction sites were introduced at the 5' and 3' termini of the 2-O sulfatase coding sequence by using primers 5' TGTTCTA-GACATATGAAGATGTACAAATCGAAAGG 3' (SEQ ID NO: 12) and 5' GTCTCGAGGAT CCTTATTTTTTTAATG-CATAAAACGAATCC 3' (SEQ ID NO: 13), respectively. At the same time, the Nde 1 restriction site already present within the sulfatase gene starting at position 1049 (FIG. 2)

was abolished by silent mutagenesis (CATATG→CATCTG) using the mutagenic primers 5' GATATTATCCCCAC-CATCTGTGGCTTTGCCGGAA 3' (SEQ ID NO: 14) and 5' TTCCGGCAAAGCCACAGA TGGTGGGGATAATATC 3' (SEQ ID NO: 15), with the A to C transversion noted in bold. In the second step, the final PCR product was gel purified and ligated into the TOPO/TA PCR cloning vector pCR 2.1 (Invitrogen) following the addition of 3' dA overhangs with 0.5 units of Taq polymerase and 300 μM dATP (10 minutes, 72° C.). Ligated DNA was transformed into One-shot TOP10 chemically competent cells. Positive clones were identified by blue/white colony selection and confirmed by PCR colony screening. In the third step, the 1.5 kb sulfatase gene was excised from pCR 2.1 TOPO and pasted into pET28a (Novagen, Madison, Wis.) as an Nde 1-Xho 1 cassette. Final expression clones were confirmed by plasmid DNA sequencing.

A 2-O sulfatase amino terminal truncation lacking the first 24 amino acids (2-O $\Delta N^{1-24}$) was PCR cloned as above except the forward primer 5' TCTAGACATATGCAAACCT-CAAAA GTAGCAGCT 3' (SEQ ID NO: 16) was used in place of original outside 5' primer listed. In this DNA construct, the 2-O sulfatase-specific sequence begins with Q25 (FIG. 2) and reads MQTSKVAASRPN (SEQ ID NO: 17).

Recombinant Expression and protein purification of a 6× histidine-tagged 2-O sulfatase (and 2-O $\Delta N^{1-24}$)—Both the full-length enzyme and the truncated enzyme (2-O $\Delta N^{1-24}$) were recombinantly expressed in the E. coli strain BL21 (DE3) (Novagen) initially as $NH_2$-terminal 6× histidine fusion proteins to facilitate purification. The protocol for their expression and subsequent one-step purification by nickel chelation chromatography was as previously described for the Δ 4,5 glycuronidase (Myette, J. R., Shriver, Z., Kiziltepe, T., McLean, M. W., Venkataraman, G., and Sasisekharan, R. (2002) *Biochemistry* 41(23), 7424-7434). Greater than 90% of the enzyme was eluted from a 5 ml column in a single 12.5 ml fraction following the addition of high imidazole elution buffer (50 mM Tris-HCL, pH 7.9, 0.5 M NaCl, and 250 mM imidazole). The enzyme was immediately diluted with 2 volumes of cold enzyme dilution buffer (50 mM Tris, pH 7.5, 100 mM NaCl). Cleavage of the 6X histidine tag by thrombin was achieved by the step-wise addition of 10 units of biotinylated thrombin (total 50 units) to 30 mL of diluted enzyme over the course of several hours while gently mixing by inversion at 4° C. Substantial precipitation of the sulfatase routinely occurred during the cleavage reaction. Thrombin was recovered by the addition of streptavidin agarose using the thrombin cleavage capture kit (Novagen). Capture was carried out a 4° C. for 2 hours with gentle mixing. Bound thrombin was collected by centrifugation for 5 minutes at 500×g. Supernatant containing soluble 2-O sulfatase was then dialyzed at 4° C. against 12 liters of enzyme dilution buffer using 20.4 mm diameter Spectra/Por dialysis tubing (Spectrum Laboratories, Rancho Dominguez, Calif.) with a 10,000 MWCO. Following dialysis, the purified sulfatase was concentrated using a Centriplus YM10 ultrafiltration device (Millipore, Watertown, Mass.). The enzyme was stable for at least two weeks at 4° C. Long-term storage was carried out at −85° C. in the presence of 10% glycerol without any subsequent loss of activity due to freezing and thawing.

Protein concentrations were determined by the Bio-Rad protein assay and confirmed by UV spectroscopy using a theoretical molar extinction coefficient ($\epsilon 280$) of 77,380 $M^{-1}$ for 2-O $\Delta N^{1-24}$ with the histidine tag removed. Protein purity was assessed by silver-staining of SDS-polyacrylamide gels.

Computational methods—Sulfatase multiple sequence alignments were made from select BLASTP database sequences (with scores exceeding 100 bits and less than 6% gaps) using the CLUSTALW program (version 1.81) preset to an open gap penalty of 10.0, a gap extension penalty of 0.20, and both hydrophilic and residue-specific gap penalties turned on. Signal sequence predictions were made by SignalP V1.1 using the von Heijne computational method (Nielsen, H., Engelbrecht, J., Brunak, S., and von Heijne, G. (1997) *Protein Eng* 10(1), 1-6).

Molecular mass determinations by MALDI-MS—The molecular weight of the 2-O sulfatase $NH_2$ truncated enzyme (2-O $\Delta N^{1-24}$) was determined by matrix-assisted laser desorption ionization mass spectrometry (MALDI-MS) essentially as described (Rhomberg, A. J., Ernst, S., Sasisekharan, R., and Biemann, K. (1998) *Proc Natl Acad Sci USA* 95(8), 4176-81). The $NH_2$-terminal histidine tag of the recombinant protein was cleaved by thrombin prior to mass analysis. 1 μL of a 2-O sulfatase solution (diluted in water to 0.5 mg/mL) was added to 1 μl of a saturated sinapinic acid matrix solution previously deposited onto the plate. The observed mass of the recombinant enzyme was corrected according to an external calibration using mass standards.

2-O sulatase assay and determination of biochemical reaction conditions—2-O sulfatase activity was measured using the unsaturated heparin trisulfated disaccharide $\Delta U_{2S}H_{NS,6S}$ or the disulfated disaccharide $\Delta U_{2S}H_{NS}$ as well as the disulfated disaccharide $\Delta UH_{NS,6S}$ lacking a sulfate at the 2-OH position. Standard reactions included 50 mM imidazole, pH 6.5, 50 mM NaCl, 500 μM disaccharide, and 25 nM of enzyme (2-O $\Delta N^{1-24}$) in a 20 μL reaction volume. The reaction was carried out for 30 seconds at 30° C. Prior to its addition, the enzyme was serially diluted to 250 nM in ice cold 1× imidazole buffer. The assay was initiated by the addition of 2 μL of this 10× enzyme stock to 18 μL of reaction mixture. The enzyme was inactivated by heating at 95° C. 11 for five minutes in pre-heated 0.5 mL eppendorf tubes. Desulfation at the 2-OH position of the disaccharide was measured by capillary electrophoresis. Resolution of substrate and product were achieved under standard conditions described for HSGAG compositional analyses (Rhomberg, A. J., Ernst, S., Sasisekharan, R., and Biemann, K. (1998) *Proc Natl Acad Sci USA* 95(8), 4176-81). Activity was generally measured as moles of desulfated product formed and was calculated from the measured area of the product peak based on molar conversion factors empirically determined from standard curves. For the detection of mono- and di-sulfated disaccharide products, total electrophoresis time was 20 minutes. Each unsaturated disaccharide peak was detected by UV absorption at 232 nm.

For pilot experiments measuring the relative effect of ionic strength on 2-O sulfatase activity, the NaCl concentration was varied from 0.05 to 1 M in 50 mM MES buffer (pH 6.5) that included 500 μM of the disulfated disaccharide $\Delta U_{2S}H_{NS,6S}$ and 50 nM enzyme. The effect of pH on sulfatase activity was assessed as a function of catalytic efficiency by measuring kinetic parameters in the following two overlapping pH buffer systems ranging from 5.0 to 8.0: 50 mM MES at pH 5.0, 5.5, 6.5, and 7.0; 50 mM MOPS at pH 6.5, 7.0, 7.5 and 8.0. Assays included 25 nM enzyme, 50 mM NaCl and varying concentrations of the disulfated disaccharide substrate $\Delta U_{2S}H_{NS}$. $K_m$ and $k_{cat}$ values were extrapolated from $V_o$ vs. [S] curves fit to the Michaelis-Menten equation by a non-linear least squares regression and the relative $k_{cat}/K_m$ ratios plotted as a function of buffer pH. Based on this profile, relative enzyme activity was also measured in four different buffers (MES, imidazole, ADA, and sodium phosphate) each present as a 50 mM concentration at pH 6.5. Relative activities were measured at a single saturating substrate concentration (4 mM) using $\Delta U_{2S}H_{NS}$.

Tandem use of 2-O sulfatase and Δ 4,5 glycuronidase in HSGAG compositional analyses—200 μg of heparin was first digested with all three heparinases in an overnight digestion in glycuronidase reaction buffer which included 50 mM PIPES, pH 6.5, 50 mM NaCl and a 100 μL reaction volume. The heparinase digestion mix was split into 4×20 μL reactions which were individually treated as follows: Tube 1, no addition (heparinase only control); Tube 2, 5 μg of Δ 4,5 glycuronidase, 30° C. 1 hour; Tube 3, 5 μg 2-O sulfatase (2-O $\Delta N^{1-24}$) 37° C., 1 hour; Tube 4, 2-O sulfatase and Δ 4,5 glycuronidase added simultaneously, 30° C., 1 hour. Δ 4,5 glycuronidase activity was ascertained by a disappearance of unsaturated disaccharide peaks due to the loss of UV absorption at 232 nm.

The substrate-product relationship between the two enzymes was examined by directly measuring Δ 4,5 glycuronidase activity either before or following the addition of recombinant 2-O sulfatase. Reactions were carried out at 30° C. and included 50 mM MES, pH 6.5, 100 mM NaCl, and 2 mM $\Delta U_{2S}H_{NS}$ in a 100 μL reaction volume. In these experiments, 250 nM Δ 4,5 glycuronidase and 25 nM 2-O $\Delta N^{1-24}$ were sequentially added as follows: Δ 4,5 alone, Δ 4,5 followed by 2-O sulfatase, or 2-O sulfatase followed by Δ 4,5. In each case, the first enzyme was added to the reaction in a 2 minute preincubation step. Δ 4,5 glycuronidase activity was measured immediately following the addition of the second enzyme by determining the rate of substrate disappearance as monitored by the loss of UV absorption at 232 nm (Myette, J. R., Shriver, Z., Kiziltepe, T., McLean, M. W., Venkataraman, G., and Sasisekharan, R. (2002) *Biochemistry* 41(23), 7424-7434). Δ 4,5 activity for the corresponding 2-O desulfated disaccharide AUHNS was also measured under identical conditions.

Homology modeling of 2-O sulfatase—The crystal structure of human arylsulfatase A, human arylsulfatase B, and the *P. aeruginosa* arylsulfatase (von Bulow, R., Schmidt, B., Dierks, T., von Figura, K., and Uson, I. (2001) *J Mol Biol* 305(2), 269-77) were used to obtain a structural model for the 2-O sulfatase enzyme. A multiple sequence alignment was performed using CLUSTALW algorithm (Higgins, D. G., Thompson, J. D., and Gibson, T. J. (1996) *Methods Enzymol* 266, 383-402) on the 2-O sulfatase and the sulfatase sequences whose crystal structures have been solved (human arylsulfatase A, B and *P. aeruginosa* arylsulfatase) (FIGS. 9 and 16). Based on this multiple sequence alignment, three model structures of 2-O sulfatase were obtained corresponding to its alignment with the other three sulfatases. The models were constructed using the Homology module of Insight II molecular simulations package (Accelrys, San Diego, Calif.). The side chain of the critical Cys 82 which is shown to undergo posttranslational modification in the active enzyme was replaced by the geminal diol [$C_\beta(OH)_2$]. The potentials for the model structures were assigned using the AMBER force field (Homans, S. W. (1990) *Biochemistry* 29(39), 9110-8). The deletions in the modeled structure were closed using 200 steps of steepest descent minimization without including charges by keeping most of the structure rigid and allowing the regions close to the deletion move freely. The final refined structure was subjected to 400 steps of steepest descent minimization without including charges and 400 steps of conjugate gradient minimization including charges.

Molecular docking of disaccharide substrates into the active site of the modeled 2-O sulfatase—Heparin derived disaccharides with a ΔU at the non-reducing end were modeled as follows. The coordinates of the trisulfated ΔU containing disaccharide ($\Delta U_{2S}H_{NS,6S}$) were obtained from the co-crystal structure of a heparinase derived hexasaccharide with fibroblast growth factor 2 (PDB id: 1BFC). This trisulfated disaccharide structure was used as a reference to generate the structural models for other disaccharides including $\Delta U_{2S}H_{NS}$, $\Delta U_{2S}H_{NAc}$ and $\Delta U_{2S}H_{NAc,6S}$. The coordinates of trisulfated disaccharides ($I_{2S}H_{NS,6S}$) containing iduronic acids in the $^1C_4$ and $^2S_0$ conformations were also obtained from 1BFC (PDB id: 1BFC). Similarly chondroitin sulfate derived disaccharides $\Delta U_{2S}Gal_{NAc,4S}$ and $\Delta U_{2S}Gal_{NAc,6S}$ were modeled using a reference structure of a chondroitin-4 sulfate disaccharide $\Delta UGal_{NAc,4S}$ whose coordinates were obtained from its co-crystal structure with the chondroitinase B enzyme (PDB id: 1DBO). The potentials for these disaccharides were assigned using the AMBER force field modified to include carbohydrates (Homans, S. W. (1990) *Biochemistry* 29(39), 9110-8) with sulfate and sulfamate groups (Huige, C. J. M., Altona, C. (1995) *J. Comput. Chem.* 16, 56-79).

The orientation of the cleavable sulfate group relative to Oγ1 of the geminal diol in the active site of human arylsulfatase A and the bacterial arylsulfatase was identical as observed in their respective crystal structures. This orientation was such that one of the faces of the tetrahedral formed by the 3 oxygen atoms of $SO_3^-$ was oriented towards Oγ1 facilitating the nucleophilic attack of the sulfur atom and the transfer of the $SO_3^-$ group to Oγ1 (Waldow, A., Schmidt, B., Dierks, T., von Bulow, R., and von Figura, K. (1999) *J Biol Chem* 274(18), 12284-8). This highly specific orientation of the sulfate group helped in positioning the disaccharide substrates relative to the active site of the 2-O sulfatase. After fixing the orientation of the 2-O sulfate group, the glycosidic torsion angles and exocyclic torsion angles were adjusted manually to remove unfavorable steric contacts with the amino acids in the active site. The enzyme substrate complexes were minimized using 200 steps of steepest descent followed by 400 steps of Newton-Raphson minimization including charges. Most of the enzyme was kept rigid and only the loop regions constituting the active site were allowed to move freely. To model the disaccharide structure, a forcing constant of 7000 kcal/mole was applied to the ring torsion angles during the energy minimization calculations while simultaneously fixing the ring conformation of the individual monosaccharide units. The manual positioning of the substrates was done using the Viewer module, building of the disaccharide structures from the reference structures was done using the Builder module and the energy minimization was done using the Discover module of Insight II.

Heparin compositional analyses by capillary electrophoresis and MALDI-MS—Approximately 10 μg of the AT-10 oligosaccharide were incubated with 100 picomoles of 2-O $\Delta N^{1-24}$ in a 40 μL reaction volume at 30° C. 15 μL aliquots were removed at 4 hours and 17 hours and heat inactivated at 95° C. The oligosaccharide reaction products (along with 15 μL of a minus sulfatase control) were subjected to an exhaustive heparinase I and III digestion prior to CE-based compositional analysis. Desulfation of the decasaccharide was assayed in parallel by MALDI-MS using established methods (Rhomberg, A. J., Ernst, S., Sasisekharan, R., and Biemann, K. (1998) *Proc Natl Acad Sci USA* 95(8), 4176-81.).

Substrate specificity and kinetics experiments using different disaccharide substrates—For substrate specificity experiments, the following heparin disaccharide substrates were used: $\Delta U_{2S}H_{NAc}$, $\Delta U_{2S}H_{NAc,6S}$, $\Delta U_{2S}H_{NS}$, and $\Delta U_{2S}H_{NS,6S}$. In addition, the chondroitin disaccharides $\Delta U_{2S}Gal_{NAc,4S}$ and $\Delta U_{2S}Gal_{NAc,6S}$ were also studied. Disaccharide concentrations for each respective substrate were varied from 0.1 mM to 4 mM. Initial rates ($V_o$) were extrapolated from linear activities representing <20% substrate turnover and fit to pseudo first-order kinetics. Standard reactions included 50 mM imidazole, pH 6.5, 50 mM NaCl, 500 μM disaccharide, and 25 nM of enzyme (2-O $\Delta N^{1-24}$) in a 20 μL reaction volume. The reaction was carried out for 30 seconds at 30° C. Prior to its addition, the enzyme was serially diluted to 250 nM in ice cold 1× imidazole buffer. The assay was initiated by the addition of 2 μL of this 10× enzyme stock to 18 μL of reaction mixture. Sulfatase activity was inactivated for five minutes at 95° C. in pre-heated 0.5 mL eppendorf tubes. Desulfation at the 2-OH position of the disaccharide was measured by capillary electrophoresis. Resolution of substrate and product were achieved under standard conditions described for HSGAG compositional analyses (Venkataraman, G., Shriver, Z., Raman, R., and Sasisekharan, R. (1999) *Science* 286(5439), 537-42). Activity was measured as moles of desulfated product formed and was calculated from the measured area of the product peak based on molar conversion factors empirically determined from standard curves. For the detection of mono- and di-sulfated disaccharide products, total electrophoresis time was 25 minutes. Each unsaturated disaccharide peak was detected by UV absorption at 232 nm. All the substrate saturation kinetics were measured under Michaelis-Menten conditions.

2-O sulfatase active site labeling and peptide mapping—Approximately 500 μg of 6× histidine-tagged 2-O $\Delta N^{1-24}$ (wild-type enzyme and C82A site-directed mutant) were lyophilized by Speed-Vac centrifugation and vigorously resuspended in 90 μL denaturation buffer containing 6M guanidinium hydrochloride, 0.1 M Tris-HCL, pH 7.5. Active site aldehydes were fluorescently labeled by adding 25 μL of Texas Red hydrazine made up as a 10 mM stock in dimethyl formamide (DMF). Labeling was carried out for three hours at room temperature with gentle mixing on a rotating platform. The hydrazone linkage was stabilized by the addition of 10 μL of a fresh 5M sodium cyanoborohydride stock made up in 1N NaOH. Reduction was carried out for 1 hour at room temperature. Unreacted fluorophore was removed by repeated acetone precipitation (added 5:1 v:v). Acetone was prechilled at −20° C. Samples were chilled at −85° C. for 20 minutes prior to spinning in a microfuge for 10 minutes, maximum speed, at 4° C. Pellets were briefly dried by Speed-Vac centrifugation.

The labeled sulfatase (and unlabeled control) were proteolyzed with sequence grade-modified trypsin for 20 hours at 37° C. in digestion buffer that contained 0.1 M Tris-HCL, pH 8.5, 1 mM EDTA, 1 mM DTT and 10% acetonitrile (v/v) in a 30 μL reaction volume. Trypsin was first reconstituted as a 2.5 mg/mL stock in 1% acetic acid and added at a 1:5 ratio (w/w) relative to the target protein. Following trypsin digestion, peptide cysteines were reduced by the addition of 50 mM DTT (50° C. under argon, 1 hour). Reduced cysteines were subsequently alkylated for 30 minutes at 37° C. (in the dark) by the addition of 150 mM iodoacetamide, added from a 2M stock made up in 0.1M Tris-HCL, pH 8.5. This reduction-alkylation cycle was repeated one more time.

Molecular masses of select peptides were determined by MALDI-MS as described (Myette, J. R., Shriver, Z., Liu, J., Venkataraman, G., Rosenberg, R., and Sasisekharan, R. (2002) *Biochem Biophys Res Commun* 290(4), 1206-13) using 1 μL of α-cyano-4-hydroxycinnamic acid (CHCA) in 50% acetonitrile, 0.3% TFA as a matrix.

Site-directed mutagenesis of the C82A active site mutant—The site-directed mutant C82A was cloned by recombinant PCR using outside primers 5' TCT AGA CAT ATG CAA ACC TCA AAA GTA GCA GCT 3' (forward, SEQ ID NO: 18) and (5' GT CTC GAG GAT CCT TAT TTT TTT AAT GCA TAA AAC GAA TCC 3' (reverse, SEQ ID NO: 19) in addition to the following mutagenic primer pair: 5' C CAG CCG CTC GCT ACA CCT TCA CG 3' (forward, SEQ ID NO: 20) and 5' CG TGA AGG TGT AGC GAG CGG CTG G 3' (reverse, SEQ ID NO: 21). The engineered codon change for each DNA strand is underlined. Subcloning into pET28a, recombinant expression in the *E. coli* strain BL21 (DE3), and subsequent purification by nickel chelation chromatography using the N-terminal 6× histidine purification tag are as described above for 2-O $\Delta N^{1-24}$.

Circular dichroism—Recombinantly expressed 2-O sulfatase and the inactive C82A mutant were concentrated and buffer-exchanged into 50 mM sodium phosphate, pH 7.0, using a Centricon 10 ultrafiltration device (Millipore). CD spectra were collected on an Aviv 62DS spectropolarimeter equipped with a thermostatic temperature control and interfaced to an IBM microcomputer. Measurements were performed in a quartz cell with a 1 mm path length. Spectra were recorded at 25° C. in an average of 5 scans between 205 and 270 nm with a 1.0 nm bandwidth and a scan rate of 12 nm/min. CD band intensities are expressed as molar ellipticities, $\theta M$, in degrees·cm²·dmol⁻¹.

Results

Molecular cloning and recombinant expression of the *F. heparinum* 2-O sulfatase—As a first step towards the cloning the 2-O sulfatase gene, we purified the enzyme directly from the native bacterium followed by a partial determination of its amino acid sequence. After a five-step chromatographic fractionation of flavobacterial lysates, we achieved a greater than 3000-fold purification of sulfatase activity. Further fractionation of this activity by reverse phase HPLC chromatography yielded two separate polypeptides (FIG. 1, Panel (A)). Both proteins were subjected to a limit trypsin digestion and the resultant peptides likewise purified by reverse phase HPLC (FIG. 1, Panel (B)). From select peak 1 peptide sequences, degenerate primers were synthesized. We initially screened primer pairs corresponding exclusively to peak 1 protein sequence (Table 1), given the fact that this sulfatase fraction represented the major protein species present in the final purification step. PCR amplification of genomic DNA using degenerate primers corresponding to peptide peaks 3 and 5 yielded a discrete 600 bp DNA product. Sequence analysis of this amplified DNA indicated a translated amino acid sequence to which three of the isolated peak 1 peptides mapped. We used this DNA, therefore, as a hybridization probe to screen a λZAP flavobacterial genomic library and isolate a full-length clone. Several positive clones were isolated; most of them contained an average insert size between 4-5 kb. One genomic clone of approximately 7 kb (clone S4A) was subjected to direct DNA sequencing. This clone contained at least one open reading frame (ORF) in particular that encodes a putative protein of 468 amino acids in length (464 amino acids from first methionine) and whose primary sequence includes all of the sulfatase peptides for which we had obtained sequence information (FIG. 2). Based on its amino acid composition, the encoded protein is quite basic (theoretical pI of 8.75), with 67 basic side chains comprising approximately 14% on a molar basis. The putative sulfatase also possesses 8 cysteines in addition to 46 aromatic amino acids.

TABLE 1

2-O-sulfatase peptides and corresponding degenerate primers

| Peak No. | Peptide Sequence | Degenerate Primers |
|---|---|---|
| 2 | YIVYDKGEIR (SEQ ID NO:22) | 5' TAYATHGTNTAYGAYAARGG 3' (SEQ ID NO:27)<br>5' NCCYTTRTCRTANACDATRTA 3' (SEQ ID NO:28) |
| 3 | TYPSVGWNESQWR (SEQ. ID. NO:23) | 5' CARCAYGGNTTYGARAGNAT 3' (SEQ ID NO:29)<br>5' DATNGTYTCATTNCCRTGYTG 3' (SEQ ID NO:30) |
| 4 | KMPHETGFTGNTPEKDGQWPDSVLMMGK (SEQ ID NO:24) | 5' TAYATHGTNTAYGAYAARGG 3' (SEQ ID NO:31)<br>5' NCGYTTRTANACDATRTA 3' (SEQ ID NO:32) |
| 5 | VAQHGFETIENTGMGDYTDAVTPSQCANFNK (SEQ ID NO:25) | 5' ATHGAYATHATHCCNACNAT 3' (SEQ ID NO:33)<br>5' DATNGTNGGDATDATRTCDAT 3' (SEQ ID NO:34) |
| 8 | TDDQLVCNGIDIIPTICGFAGIAK (SEQ ID NO:26) | 5' GAYATHATHCCNACNATHTGYTT 3' (SEQ ID NO:35)<br>5' AARCADATNGTNGGDATDATRTC 3' (SEQ ID NO:36) |

Figure 1B:
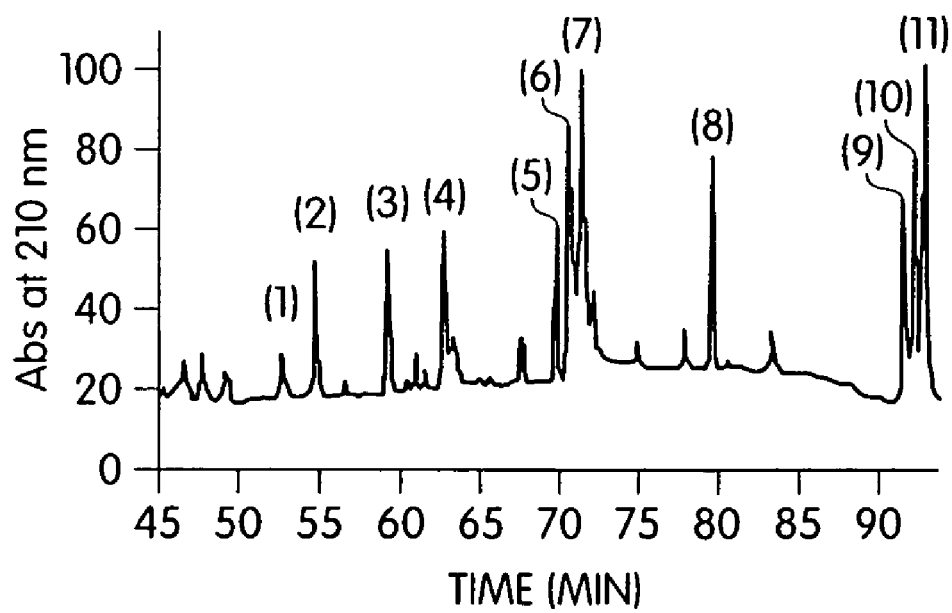

Select RP-HPLC purified tryptic peptides (see also FIG. 1, Panel (B)) were subjected to amino acid sequencing. Also shown are the corresponding degenerate primers.

Upon a closer examination of its primary sequence, we also identified a conserved sulfatase domain. This signature domain included the consensus sequence C/SX-PXRXXXXS/TG (SEQ ID NO: 6) presumably comprising (at least in part) the sulfatase active site and possessing the cysteine (denoted in bold) that is most likely modified as a formylglycine in vivo. The putative 2-O sulfatase that we cloned from F. heparinum exhibits substantial homology to many members of a highly conserved sulfatase family (FIG. 3) (Bond, C. S., Clements, P. R., Ashby, S. J., Collyer, C. A., Harrop, S. J., Hopwood, J. J., and Guss, J. M. (1997) Structure 5(2), 277-89, Parenti, G., Meroni, G., and Ballabio, A. (1997) Curr Opin Genet Dev 7(3), 386-91). A structurally-oriented description of this homology and its correlation to enzyme function is found below.

From this sequence information, we were confident that we had indeed cloned a sulfatase from the flavobacterial genome. To ultimately establish its functionality, we next set out to recombinantly express this protein in E. coli. The full-length gene (beginning at the first methionine noted in FIG. 2) was subcloned into the T7-based expression vector, pET28a for expression as an $NH_2$-terminal 6× histidine-tagged protein to facilitate purification. Induction with IPTG led to a limited soluble expression of a polypeptide whose apparent molecular weight roughly corresponded to the theoretical mass of the fusion protein (approximately 54 kDa). Using $Ni^{+2}$ chelation chromatography, we were able to partially purify this polypeptide from the bacterial lysate and unequivocally measure 2-O specific sulfatase activity using the trisulfated, unsaturated heparin disaccharide $\Delta U_{2S}H_{NS,6S}$ as a substrate.

Figure 4:
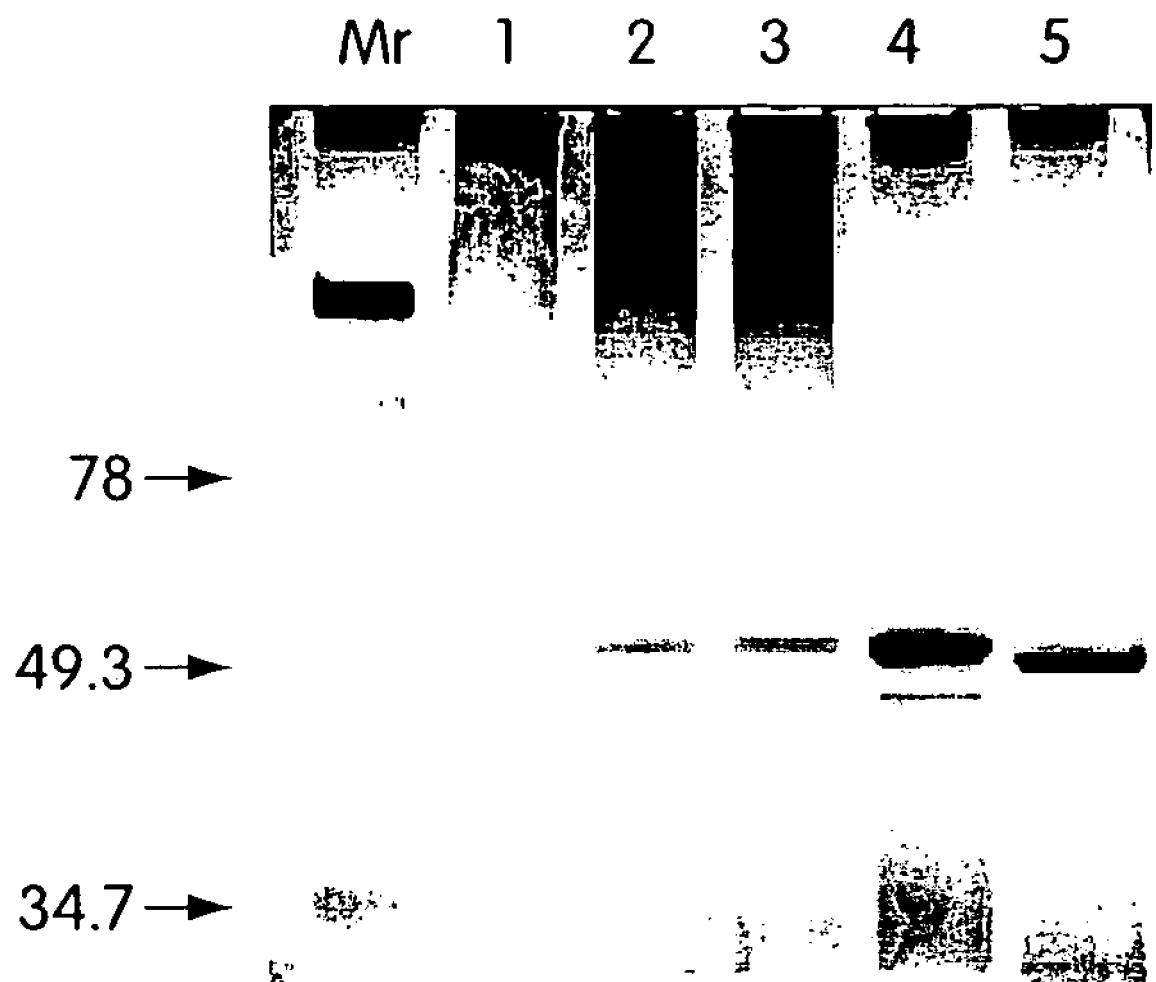
FIG. 4 provides the results from the purification of recombinant 2-O sulfatase from *E. coli* lysates by $Ni^{+2}$ chelation chromatography. Enzyme purity following each fractionation step was assessed by silver-staining of 12% SDS-polyacrylamide gels. Approximately 200 ng of total protein was loaded in each well. Lane 1, bacterial lysate from uninduced (minus IPTG) control; lane 2, whole cell lysate; lane 3, 20,000×g supernatant (column pre-load); lane 4, eluate from $Ni^{+2}$ chelation chromatography; lane 5, 2-O sulfatase following thrombin cleavage to remove $NH_2$ 6× histidine purification tag. Molecular weight markers ($M_r$) and their corresponding masses are also shown.

We identified a putative signal sequence for the flavobacterial 2-O sulfatase comprised of the first 24 amino acids (see FIG. 2). By engineering a 2-O sulfatase N-terminal truncation lacking this sequence (herein referred to as 2-O $\Delta N^{1-24}$), we achieved high expression levels of soluble, highly active enzyme. Protein yields exceeding 100 mg of relatively pure sulfatase per liter of induced bacterial cultures were routinely achieved using a single chromatographic step (FIG. 4). The specific activity of the recombinant sulfatase was considerably enhanced following the removal of the N-terminal 6×-histidine tag by thrombin cleavage. Removal of this purification tag resulted in a greater than 10-fold purification of sulfatase activity relative to the crude bacterial lysate (Table 2). For this reason, we used the cleaved protein in all subsequent experiments. The molecular weight of this recombinantly expressed sulfatase as determined by MALDI-MS is 50,120.8 Daltons. This empirical value closely agrees with its theoretical mass of 49,796 Daltons that is based entirely on its amino acid composition.

TABLE 2

Purification of recombinant 2-O-sulfatase

| Fraction | Total Protein (mg) | Specific Activity (nanomoles of DiS/min/μg protein) | Fold-purification |
|---|---|---|---|
| lysate | 322 | 4.14 | — |
| $Ni^{+2}$ (with His Tag) | 122 | 7.43 | 1.8 |
| His Tag removal | 15* | 42.3 | 10.2 |

200 ng of total protein from each purification step was assayed for 2-O-sulfatase activity as described in Materials and Methods using the unsaturated heparin disaccharide (DiS) $U_{2S}H_{NS}$ as a substrate.
Fold purification is relative to crude bacterial lysate.
*Soluble enzyme remaining after substantial loss due to protein precipitation.

To establish the recombinant enzyme's exclusivity for the uronic acid 2-O sulfate, we initially compared two related unsaturated heparin disachharides: $\Delta U_{2S}H_{NS,6S}$ versus $\Delta UH_{NS,6S}$. The recombinant sulfatase only hydrolyzed a single sulfate, namely, the one found at the 2-OH position (FIG. 5).

Biochemical conditions for optimal in vitro activity—Having successfully achieved the recombinant expression and purification of the flavobacterial sulfatase as a soluble enzyme as well as demonstration of its unequivocal specificity for the uronic acid 2-O sulfate, we next set out to define the reaction conditions required for optimal enzyme activity in vitro. These parameters included pH, temperature, ionic strength, and possible divalent metal ion dependency. In brief, the enzyme exhibited a pH activity range between 6.0 and 7.0, with optimum activity occurring at pH 6.5 (FIG. 6, Panel (A)). The enzyme was essentially inactive at the outlying pH values of 5.0 and 8.0. In terms of different buffer systems (all at pH 6.5), an imidazole-based buffer demonstrated the highest relative activity as compared with buffers containing 50 mM MES, ADA, or phosphate. As expected, phosphate buffer was clearly inhibitory (FIG. 6, Panel (A) inset).

We also examined 2-O sulfatase activity relative to ionic composition. The recombinant enzyme was optimally active at approximately 50 mM NaCl. Activity was sharply inhibited by [NaCl] exceeding 100 mM, with 50% inhibition occurring at less than 250 mM NaCl (FIG. 6, Panel (B)). Maximal enzyme activity was largely unaffected by the addition of EDTA up to a 1 mM concentration. Addition of exogenous $CaCl_2$, $MgCl_2$, or $MnCl_2$ (up to 10 mM) also had no substantive effect, indicating that these particular divalent metal ions are not required. A preincubation of the enzyme with 5 mM EDTA did result in an approximately 10% inhibition of activity using the trisulfated disaccharide as a substrate.

37° C. was the default temperature at which all of the preliminary biochemical experiments were conducted. We measured both relative enzyme activity and stability as a function of varying reaction temperature (FIG. 6, Paenl (C)). The 2-O sulfatase was active over a fairly broad temperature range (25° C. to 37° C.), with optimal activity occurring at 30° C. Enzyme activity was compromised at 42° C. Enzyme stability at this temperature was likewise affected as assessed in pre-incubation experiments conducted at varying temperatures (30° C.→42° C.) prior to measuring 2-O sulfatase activity at 30° C.

Figure 7:
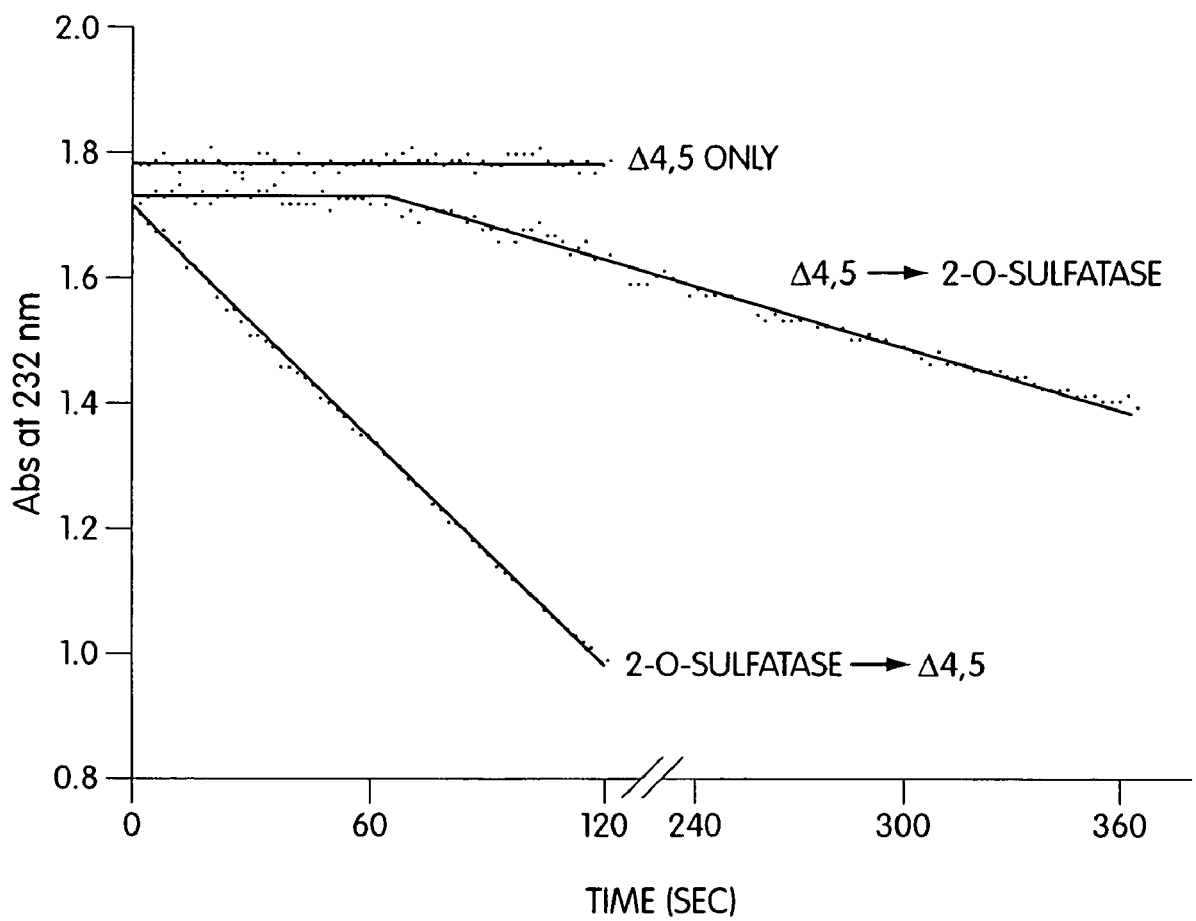
FIG. 7 illustrates the substrate-product relationship between the 2-O sulfatase and the $\Delta 4,5$ glycuronidase. 2 mM of the unsaturated, 2-O sulfated heparin disaccharide $\Delta U_{2S}H_{NS}$ was preincubated with either 250 nM $\Delta 4,5$ glycuronidase or 25 nM 2-O $\Delta N^{1-24}$ for two minutes at 30° C. in a 100 µL reaction. Following this preincubation, the reciprocal enzyme was added to the reaction for up to six extra minutes. $\Delta 4,5$ glycuronidase activity was measured in real time as the rate of substrate disappearance monitored by the loss of UV absorption at 232 nm. Zero time on the x-axis represents the time following the preincubation during, which the second enzyme was added.
Figure 8A:
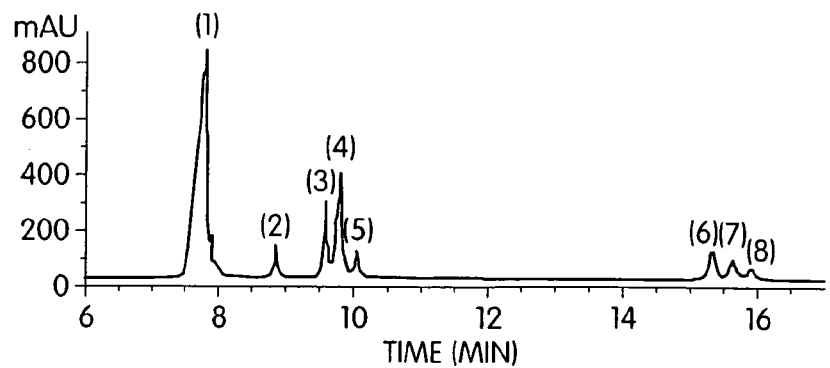
FIG. 8 illustrates the results of the tandem use of 2-O sulfatase and $\Delta 4,5$ glycuronidase in HSGAG compositional analyses. Panel (A) provides the results of exhaustively cleaving 200 µg heparin with heparinase I, II and III. These heparinase-generated saccharides were then subjected to hydrolysis by the $\Delta 4,5$ glycuronidase. Panel (B) provides the results of subsequent hydrolysis by 2-O sulfatase after the heparinase treatment. Panel (C) illustrates subsequent hydrolysis by 2-O sulfatase and by $\Delta 4,5$ glycuronidase added simultaneously. Panel (D) depicts the 7 disaccharide peaks (and one tetrasaccharide peak) resolved by capillary electrophoresis (each numbered separately). Their compositional assignments are as follows: $\Delta U_{2S}H_{NS,6S}$ (1); $\Delta UH_{NAc,6S}GH_{NS,3S,6S}$ tetrasaccharide (2); $\Delta U_{2S}H_{NS}$ (3); $\Delta UH_{NS,6S}$ (4); $\Delta U_{2S}H_{NAc,6S}$ (5); $\Delta UH_{NS}$ (6); $\Delta U_{2S}H_{NAc}$ (7); and $\Delta UH_{NAc,6S}$ (8).
Figure 8B:
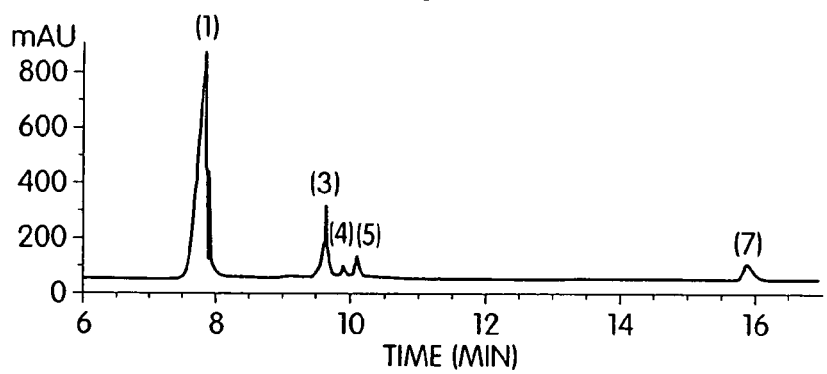
Figure 8C:
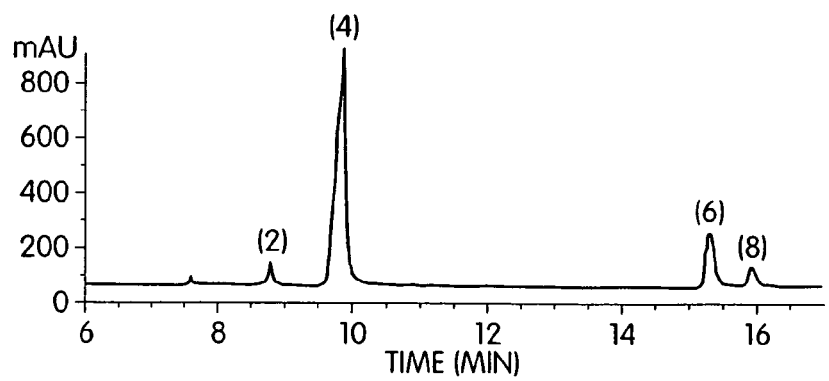
Figure 8D:
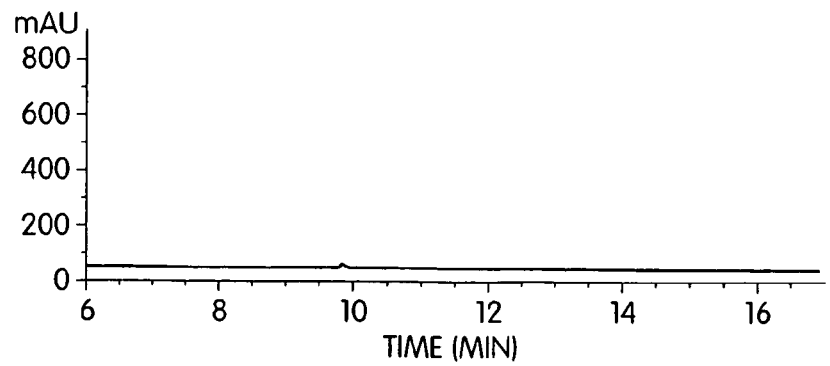

The substrate-product relationship between the 2-O sulfatase and Δ 4,5 glycuronidase—As we have already noted, the flavobacterial Δ 4,5 glycuronidase is unable to hydrolyze unsaturated saccharides possessing a uronic acid 2-O sulfate at the non-reducing end (Myette, J. R., Shriver, Z., Kiziltepe, T., McLean, M. W., Venkataraman, G., and Sasisekharan, R. (2002) *Biochemistry* 41(23), 7424-7434). We hypothesized that, an obligatory substrate-product relationship between the 2-O sulfatase and the Δ 4,5 glycuronidase may exist. We examined a possible kinetic relationship between these two enzymes by looking at their sequential action (FIG. 7). In this experiment, Δ 4,5 glycuronidase activity was measured directly either during or following the addition of the recombinant 2-O sulfatase using the disaccharide substrate $\Delta U_{2S}H_{NS}$. When this disaccharide was incubated with the Δ 4,5 enzyme alone, it was completely refractory to glycuronidase-mediated hydrolysis as measured by a loss of absorbance at 232 rn. A 2 minute preincubation of the substrate with the 2-O sulfatase, however resulted in robust linear glycuronidase activity. This rate was comparable to the rate of hydrolysis measured for the control substrate $\Delta UH_{NS}$ using the Δ 4,5 enzyme alone. In the reciprocal experiment (i.e., whereby the 2-O sulfatase was added second), we observed an initial lag in Δ 4,5 activity. This lag was followed by a linear Δ 4,5 activity, albeit at a slower rate than in the case where the 2-O sulfatase was added first. The observed delay in activity was presumably due to the prerequisite 2-O desulfation of the substrate which must occur prior to being acted on by the glycuronidase. This experiment clearly demonstrates at least a functional linkage between these two HSGAG degrading enzymes.

With the results just described, we considered the parallel use of these two enzymes (along with the heparinases) as complementary tools for HSGAG compositional analyses. The utility of this combinatorial approach is shown in FIG. 8. 200 μg of heparin were first subjected to an exhaustive heparinase treatment. Subsequent treatment of the cleavage products with the Δ 4,5 glycuronidase resulted in the disappearance of select saccharide peaks, namely those that did not possess a 2-O sulfated uronic acid at the non-reducing end (FIG. 8, Panel (B)). Conversely, subsequent treatment of the heparinase-derived saccharides with the 2-O sulfatase results in both the disappearance of 2-O sulfated disaccharides as well as a concomitant appearance of their desulfated products (FIG. 8, Panel (C)). When both the Δ 4,5 glycuronidase and the 2-O sulfatase were added simultaneously to the heparinase cleavage products, essentially all of the saccharides were hydrolyzed by the Δ 4,5 glycuronidase as evident by a lack of any UV absorbable electrophoresis products (FIG. 8 Panel (D)).

Figure 10A:
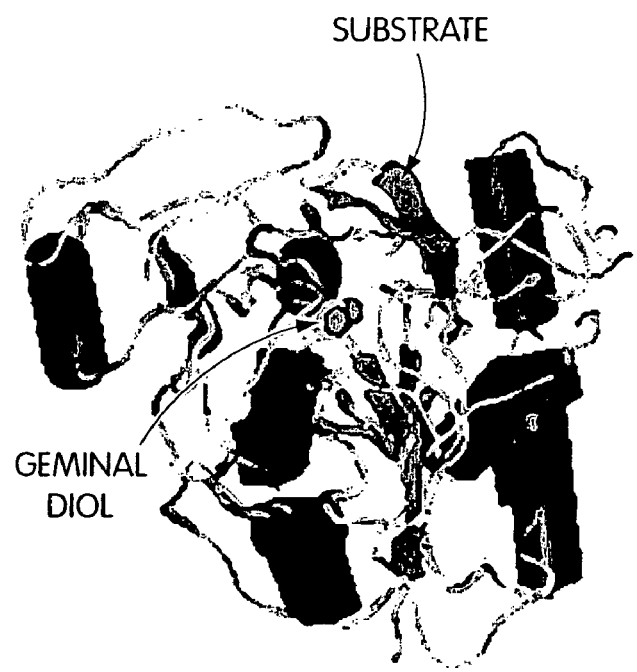
FIG. 10 provides the structural model of 2-O sulfatase and topology of the active site. Panel (A) is the ribbon diagram of the proposed 2-O sulfatase structure constructed using homology modeling of the crystal structure of human arylsulfatase B. The β strands are shown as thicker areas of the ribbon diagram, and the α helices are shown as cylindrically shaped areas. The geminal diol form of the modified cysteine is also depicted (rendered as CPK; carbon and oxygen molecules are shown). The direction of substrate diffusing into the active site is indicated by an arrow. Panel (B) provides the CPK rendering of the top view of the structure shown in Panel (A). The modified cysteine, the surrounding basic amino acids (Arg, His and Lys), acidic amino acids (Asp, Glu), and Gln and Asn are all shown. Note that the active site geminal diol is located in the bottom of a deep cleft.
Figure 10B:
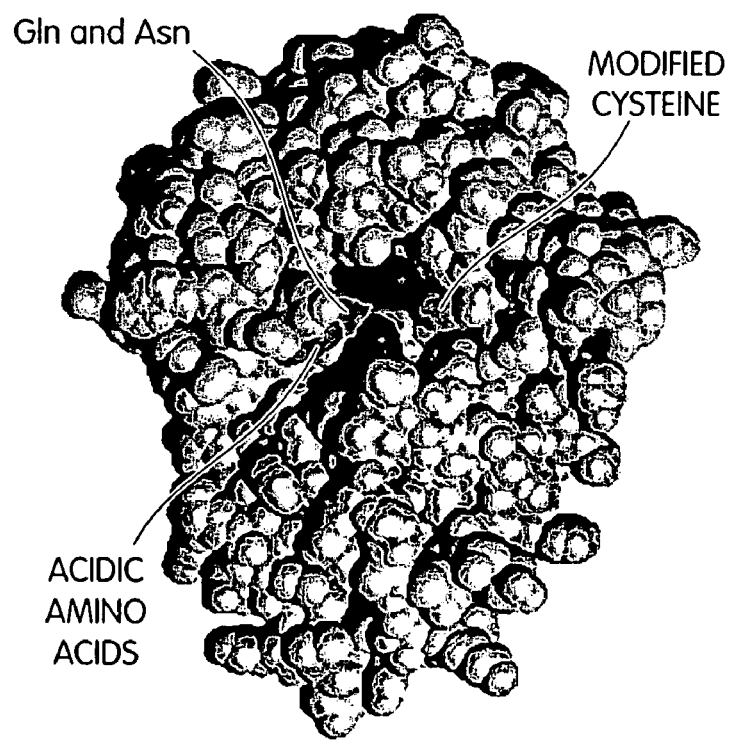

Structure-based homology modeling of the 2-O sulfatase active site—The crystal structures of three sulfatases have been solved. These sulfatases are human arylsulfatase A (Lukatela, G., Krauss, N., Theis, K., Selmer, T., Gieselmann, V., von Figura, K., and Saenger, W. (1998) *Biochemistry* 37(11), 3654-64, von Bulow, R., Schmidt, B., Dierks, T., von Figura, K., and Uson, I. (2001) *J Mol Biol* 305(2), 269-77), arylsulfatase B (N-acetylgalactosamine-4-sulfatase) (Bond, C. S., Clements, P. R., Ashby, S. J., Collyer, C. A., Harrop, S. J., Hopwood, J. J., and Guss, J. M. (1997) *Structure* 5(2), 277-89), and a bacterial arylsulfatase from *Pseudomonas aeruginosa* (Boltes, I., Czapinska, H., Kahnert, A., von Bulow, R., Dierks, T., Schmidt, B., von Figura, K., Kertesz, M. A., and Uson, I. (2001) *Structure* (Camb) 9(6), 483-91). In comparing their structures, we observed a structural homology between each of them, especially as it pertained to a conservation of critical active site residues and their spatial arrangement. By extension, most of these amino acids were likewise conserved in the flavobacterial 2-O sulfatase as evident by a direct alignment of their primary sequences (FIGS. 9 and 16). We used this close structural relationship to construct three homology-based models for the flavobacterial 2-O sulfatase, each one based on one of the three crystal structures examined. We ultimately chose as our representative 2-O sulfatase structure the homology model constructed using the N-acetylgalactosamine-4-sulfatase (arylsulfatase B) (FIG. 10). This decision was largely based on it also being a GAG desulfating enzyme. In this model, we replaced cysteine 82 with a formylglycine (FGly 82). We chose to represent FGly 82 in the hydrated state as a geminal diol [—$C_\beta$ $(OH)_2$], consistent with the proposed resting state (before catalysis) of the enzyme (Lukatela, G., Krauss, N., Theis, K., Selmer, T., Gieselmann, V., von Figura, K., and Saenger, W. (1998) *Biochemistry* 37(11), 3654-64, Waldow, A., Schmidt, B., Dierks, T., von Bulow, R., and von Figura, K. (1999) *J Biol Chem* 274(18), 12284-8).

Upon inspection of the 2-O sulfatase structure, several amino acids that potentially constitute the active site were identified (Table 3). There are several structurally conserved basic amino acids in the proximity of FGly 82 including Arg 86, Lys 134, His 136 and Lys 308. The topology of the active site as observed in our structural model indicated that the critical FGly 82 and the basic amino acid cluster are located at the bottom of a deep pocket (FIG. 10, Panel (B)). Such restrictive access to the active site would appear to impose a clear structural constraint on the substrate as it relates to the position of the 2-O sulfate group within the oligosaccharide chain (i.e., externally vs. internally positioned) upon which the enzyme acts. We predicted from this topology that a sulfate group present at the non-reducing end of the oligosaccharide will be favorably positioned for catalysis; the juxtaposition of an internal sulfate into the active site would require a substantial bending of the oligosaccharide chain. Such chain distortion would be sterically unfavorable. Based on these constraints, therefore, we predicted the sulfatase to hydrolyze 2-O sulfates in an exclusively exolytic fashion. This exclusivity for the non-reducing end does not necessarily preclude, however, the enzyme acting on longer chain oligosaccharides (i.e., those exceeding a disaccharide in length) provided that they in fact possess sulfates at the terminal 2-OH position. The model does suggest a likely kinetic preference for disaccharide substrates as they would most readily diffuse into and out of this narrow active site (see enzyme-substrate structural modeling below).

TABLE 3

Structure-based comparison of sulfatase active site residues

| 2-O sulfatase F. hepartaum | Arylsulfatase A Human | Arylsulfatase B Human | Arylsulfatase P. aeruglaosa |
|---|---|---|---|
| Cys-82 | Cys-69 | Cys-91 | Cys-51 |
| Arg-86 | Arg-73 | Arg-95 | Arg-55 |
| Lys-134 | Lys-123 | Lys-145 | Lys-113 |
| His-136 | His-125 | His-147 | His-115 |
| Lys-308 | Lys-302 | Lys-318 | Lys-375 |
| Gln-237 | His-229 | His-242 | His-211 |
| Asp-42 | Asp-29 | Asp-53 | Asp-13 |
| Gln-43 | Asp-30 | Asp-54 | Asp-14 |
| Asp-295 | Asp-281 | Asp-300 | Asp-317 |
| His-296 | Asn-282 | Asn-301 | Asn318 |
| Lys-238* | Tyr-230 | Glu-243 | Trp-212 |
| Lys-175* | Gln-153 | Arg-180 | Pro-161 |
| Asp-159* | His-151 | Ser-172 | Ala-139 |
| Thr-104* | Val-91 | Ile-113 | – |
| Glu-106 | Val-93 | Trp-115 | – |
| Lys-107* | Pro-94 | Pro-116 | – |
| Gln-309* | Gly-303 | Trp-319 | Ala-376 |

Highly conserved amino acids are listed in black. Non-conserved amino acids are listed in gray. Amino acids in the 2-O sulfatase that could be potentially involved in substrate binding are noted by an asterisk. Structural alignment of the modeled 2-O sulfatase structure with the other sulfatases was obtained based on superposition of their Cα traces using the combinatorial extension algorithm (McLean, M. W., Bruce, J. S., Long, W. F., and Williamson, F. B. (1984) Eur J Biochem 145(3), 607-15). Regions of deletion in the structural alignment are noted with a minus sign.

glutamines are commonly occurring amino acids in heparin binding sites that interact with the sulfate and carboxylate group. Unlike the amino acids proximal to the FGly 82, these residues are not conserved in the other sulfatases that we examined (Table 3, denoted in gray), suggesting a potentially unique role of these amino acids in dictating oligosaccharide substrate specificity. This disparity is particularly true when directly comparing the 2-O sulfatase and arylsulfatase A; many of the non-conserved amino acids in the 2-O sulfatase are charged while those in arylsulfatase A are predominantly hydrophobic. This observation is consistent with the structural distinction of their respective substrates, i.e., the highly sulfated HSGAG substrates of the 2-O sulfatase vs. the long hydrophobic alkyl chains of cerebroside-3-sulfate substrate of arylsulfatase A.

Enzyme-substrate structural complex. Interaction between 2-O sulfatase and disaccharides—Since the active site can readily accommodate disaccharide substrates, we modeled several unsaturated glycosaminoglycan disaccharides. Our choice of Δ 4,5 unsaturated substrates was logical for two reasons: 1) β-eliminative cleavage of a HS polysaccharide by the flavobacterial lyases that naturally occurs in vivo results in the formation of disaccharides and other small oligosaccharides all possessing a Δ4-5 unsaturated bond at the non-reducing end uronic acid and; 2) the obligatory substrate-product relationship between the 2-O sulfatase and the Δ 4,5 glycuronidase that exists both in vitro and in vivo. A representative structural complex involving the trisulfated disaccharide $\Delta U_{2S}H_{NS,6S}$ (FIG. 11) was used to describe the molecular interactions between the enzyme and the substrate. This choice was ultimately validated by the substrate kinetics. A description of these interactions and their proposed functional roles is shown in Table 4. The functional roles of the conserved active site amino acids (listed in bold) were proposed based on their interactions with the 2-O sulfate group and/or the geminal diol of the formylglycine at position 82. Identical roles have been proposed for the corresponding amino acids in the three known sulfatase crystal structures (Table 3).

TABLE 4

Functional assignment of 2-O-sulfatase active site amino acids

| Active site Amino acids | Proposed functional role |
|---|---|
| Cys-82 | Modified into hydrated form of the FGly —Oγ1 positioned for nucleophilic attack on sulfate group. |
| Arg-86, His-136 | Stabilizing the hydrated FGly by interaction with Oγ2. His-136 is also positioned favorably for abstraction of proton from Oγ2 after catalysis to eliminate the sulfate group and regenerate geminal diol. |
| Lys-134, Lys-308, Gln-237 | Coordinate with the oxygen atoms of 2-O sulfate group to enhance electron density withdrawal from sulfate group thereby increasing the electrophilicity of sulfur center. Lys308 is also positioned to protonate the oxygen atom on the leaving substrate. |
| Asp-295 | Enhances nucleophilicity of Oγ1 by proton donation. |
| Lys-238, Lys-175 | Interaction with planar carboxyl group of AU may be critical for substrate recognition and positioning the 2-O sulfate group. |
| Thr-104, Lys-107 | Interaction with 6-O sulfate on glucosamine may be critical for positioning of 2-O sulfate group. |
| Leu-390, Leu-391, Leu-392 | Better positioned to make favorable hydrophobic contacts with the N-acetyl group. |

The amino acids listed in the first column were identified by inspection of the structural model presented in FIG. 3. The critical active site Cys-82 is indicated in boldface.

The surface of the active site pocket is comprised of many amino acids that can potentially interact with a disaccharide substrate. These include Lys 107, Lys 175, Lys 238, Gln 237 and Gln 309, Thr 104, Glu 106 and Asp 159. Lysines and A closer inspection of the modeled enzyme-substrate complex revealed some interesting possibilities pertaining to the role of the non-conserved amino acids in substrate recognition and binding. The planar carboxylate group attached to the C5 atom of the Δ4-5 uronic acid is oriented in such a manner as to potentially interact with Lys 175, Lys 238. These amino acids could play an important role, therefore, in favorably orienting the 2-O sulfate within the active site. We were further interested in this arrangement given the additional constraint imposed upon the planar carboxyl group of the uronic acid by the presence of the C4-C5 double bond. This constraint may further influence substrate orientation within the active site. Given this possibility, we predicted a substrate discrimination exhibited by the 2-O sulfatase which is based on the presence of the Δ 4,5 double bond at the oligosaccharide non-reducing terminus. In the absence of this double bond, the favorable orientation of the 2-O sulfate and the C5 carboxylate afforded by charge interactions with Lys 178 and Lys 238, respectively, would not occur.

To better understand this likely structural constraint, we superimposed onto our trisulfated model substrate disaccharides containing a non-reducing end iduronic acid in either the $^1C_4$ or $^2S_0$ conformation. The superimposition was such that the S—O—C2-C1 atoms of all the uronic acids coincided, thereby fixing the orientation of the 2-O sulfate group. In this model, the carboxylate groups of the iduronic acid containing disaccharide substrates were, in fact, pointing away from the active site pocket and were not positioned to interact as favorably with the active site amino acids (i.e., Lys 175, Lys 238) as compared with the original disaccharide substrate possessing a planar C5 carboxylate.

Figure 11A:
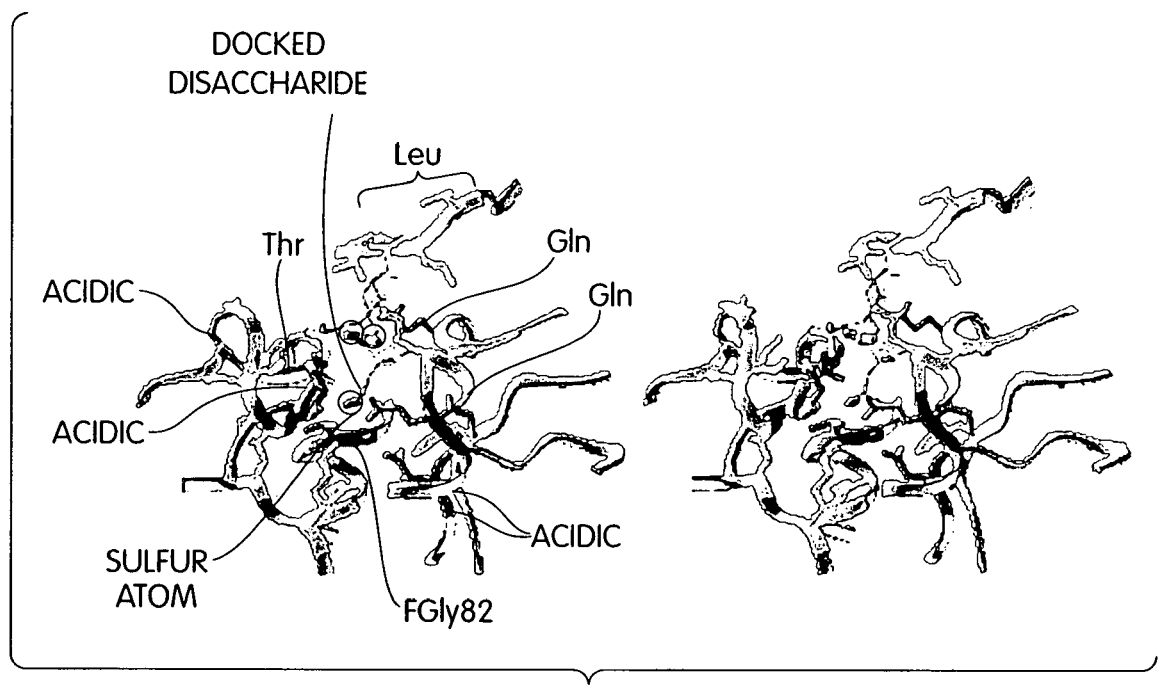
FIG. 11 depicts the active site amino acids and their interaction with $\Delta U_{2S}H_{NS,6S}$. Panel (A) is the stereo view of the 2-O sulfatase active site highlighting important amino acids (shown here by a stick representation). Acidic amino acids (Asp), Gln, Thr, Leu, and FGly 82 are depicted. The docked disaccharide is also shown using a stick representation. The sulfur atom of the 2-O sulfate group (next to the lowest positioned oxygen) and oxygen atoms (circled) of the 2-O sulfate group and the planar carboxyl group are also depicted. Panel (B) provides the schematic representation of the amino acids shown in Panel (A). Potential metal ion coordination is also shown with the divalent cation ($Mg^{2+}$) depicted as a gray circle.
Figure 11B:
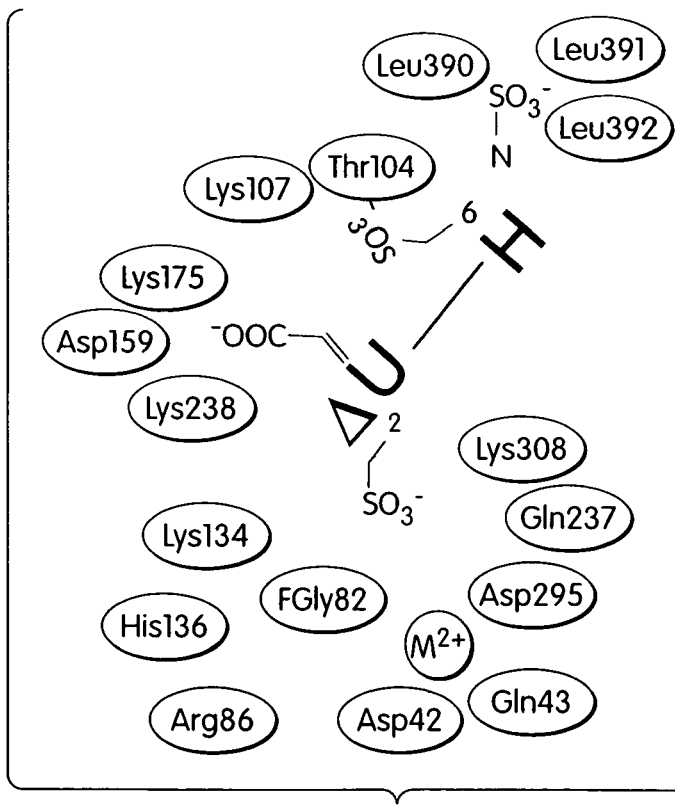

Our structural model of a sulfatase-trisulfated disaccharide complex also points out key interactions involving additional sulfates (other than the uronic acid 2-OH position) present on the adjoining glucosamine. In particular, the 6-O sulfate group interacts with the basic side chain of Lys 107 within the enzyme active site (FIG. 11). This putative charge interaction would likely play an important role in stabilizing the orientation of the substrate in the active site. In contrast, the N-sulfate group of the disaccharide glucosamine is proximal to a contiguous stretch of leucines (390-392). In such an arrangement, it is the methyl group of an N-acetylated glucosamine rather than a sulfate at this position which is more likely to make favorable hydrophobic contacts with these residues. This prediction was borne out in one of our models docking the $\Delta U_{2S}H_{NAc,6S}$ substrate in the active site.

We also modeled enzyme-substrate complexes containing two unsaturated chondroitin sulfate disaccharides ($\Delta U_{2S}Gal_{NAc,4S}$ and $\Delta U_{2S}Gal_{NAc,6S}$). In comparison to our original model using the heparin disaccharide substrate, we found interactions with the 2-O sulfate and carboxyl group of the ΔU monosaccharide that were identical to that of $\Delta U_{2S}H_{NS,6S}$. There were few interactions involving the 4-sulfate and 6-sulfate groups, however. This particular model, therefore, does not exclude the ability of the so-called "heparin/heparan sulfate" 2-O sulfatase to hydrolyze 2-O sulfated chondroitin disaccharides. Given a lack of additional favorable contacts between the enzyme and substrate (e.g., with either the 4-O or 6-O sulfates), we would anticipate a lower catalytic efficiency for the chondroitin disaccharides relative to the structurally corresponding heparin disaccharides.

In discussing this model, we must briefly consider the potential role of divalent metal ions. We decided not to include any such metal ions in our model of the 2-O sulfatase as we could find no divalent metal requirement for enzymatic activity. A divalent metal ion is present, however, in all three sulfatase crystal structures that we examined. In each case, the metal ion coordinates with the oxygen atoms of the sulfate group of the respective substrate. Additionally, a cluster of four highly conserved acidic amino acids has been observed to coordinate with this divalent metal ion. In the case of human arylsulfatase B, for example, the oxygen atoms of Asp 53, Asp 54, Asp 300 and Asn 301 are coordinated with a $Ca^{2+}$ ion. Three of the four corresponding amino acids in the flavobacterial sulfatase model that we have identified as potentially coordinating with a metal ion are Asp 42, Gln 43 and Asp 295 (Table 3). The fourth amino acid in the 2-O sulfatase corresponding spatially to Asn 301 of arylsulfatase B is His 296. The positive charge of this position, however, does not favor the proximal location of a divalent metal cation. It is perhaps this unfavorable charge interaction which interferes with proper metal ion coordination.

Enzyme-substrate model. Mechanism for catalysis—Nearly identical mechanisms for the hydrolysis of the sulfate ester bond involving the conserved active site amino acids have been proposed for human arylsulfatases A and B and the bacterial sulfatase from *Pseudomonas aeruginosa*. The resting state of the active sulfatase in each of the crystal structures is proposed to contain the geminal diol which is stabilized by interactions with basic residues. His 136 and Arg 86 of the flavobacterial enzyme are positioned appropriately in the active site to do so (FIG. 10, Patel (B)). A critical step in catalysis involves the correct positioning the 2-O sulfate group such that the sulfur atom is accessible to the Oγ1 of the geminal diol. We have already described how interactions of specific active site amino acids with the planar carboxyl group of the uronic acid (Lys 175, Lys 238), with the 6-O sulfate of the glucosamine (e.g., Lys 107 and possibly Thr 104) and with the 2-O sulfate itself (Lys 134, Lys 308) are likely to serve in this capacity (Table 4). At the same time, interaction of the 2-O sulfate group with charged amino acids would also enhance any electron density withdrawal from the oxygen atoms, thereby increasing the electrophilicity of the sulfur center. It has also been suggested that the nucleophilicity of the Oγ1 atom is enhanced by a possible proton donation to a neighboring aspartic acid residue. In our structural model of the 2-O sulfatase, this residue would correspond to Asp 295.

An $S_N2$ mechanism may follow the above steps and eventually lead to the cleavage of the sulfate ester bond. In this mechanism, the exocyclic oxygen atom on the leaving substrate may be protonated by water or potentially by neighboring amino acids. In the 2-O sulfatase active site model, Lys 308 is juxtaposed to protonate the leaving group (FIG. 11). The resulting sulfate group on the geminal diol is subsequently eliminated by abstraction of a proton from Oγ2 regenerating the formylglycine. His 136 is positioned to abstract this proton.

As we have already pointed out, our homology-based model of the 2-O sulfatase has several structure-function implications relating to substrate specificity. Many of these points are summarized in Table 4. When examined from the perspective of oligosaccharide structure, our model addresses the issue of substrate specificity principally as it relates to the following parameters: 1) the exolytic action of the enzyme; 2) the influence of oligosaccharide chain length; 3) the presumed requirement for an unsaturated double bond at the non-reducing end; 4) the number and position of additional sulfates present within the glucosamine adjoining the 2-O sulfated uronic acid and; 5) the nature of the glycosidic linkage position between these two monosaccharides. In the example which follows, each of these predictions is empirically examined through biochemical and kinetic studies defining substrate preference.

Figure 12A:
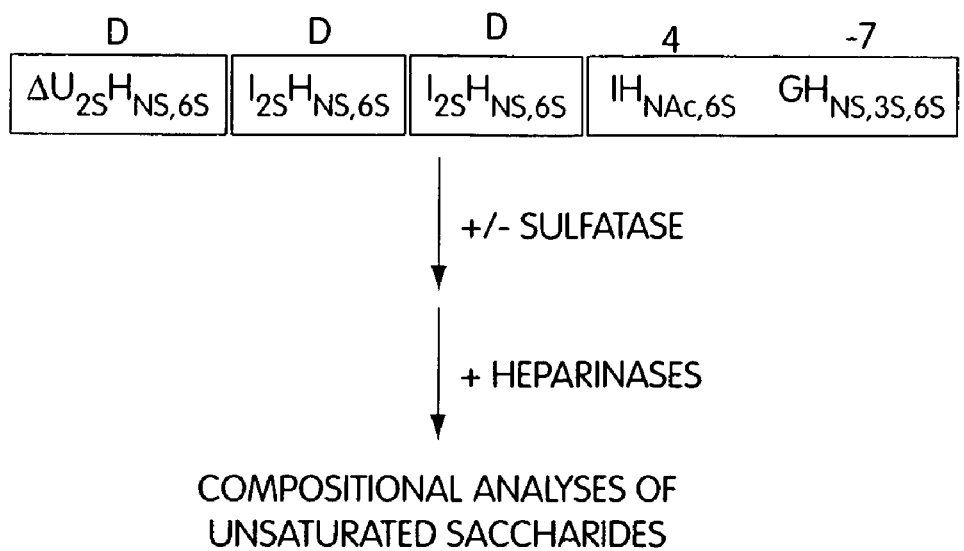
FIG. 12 illustrates the exolytic activity of the 2-O sulfatase by analyzing the ability of the sulfatase to hydrolyze internally positioned 2-O sulfates within the AT10 decasaccharide and subsequent compositional analyses of the heparinase-treated product. Panel (A) shows the AT-10 decasaccharide sequence with PEN-MALDI nomenclature and outline of experimental design. Panel (B) provides the capillary electrophoretogram for both the control and sulfatase pre-treated samples along with their saccharide compositional assignments. Heparinase cleavage products following sulfatase pretreatment are shown as a dashed line (with gray fill). Minus sulfatase control is shown as a white line (no fill). The pentasulfated tetrasaccharide (4, −7) is also noted. Disappearance of the trisulfated disaccharide (D) by one-third and the corresponding appearance of the 2-O desulfated product ($\Delta UH_{NS,6S}$) are depicted by vertical arrows. The minor tetrasaccharide contaminant is noted by an asterisk.
Figure 12B:
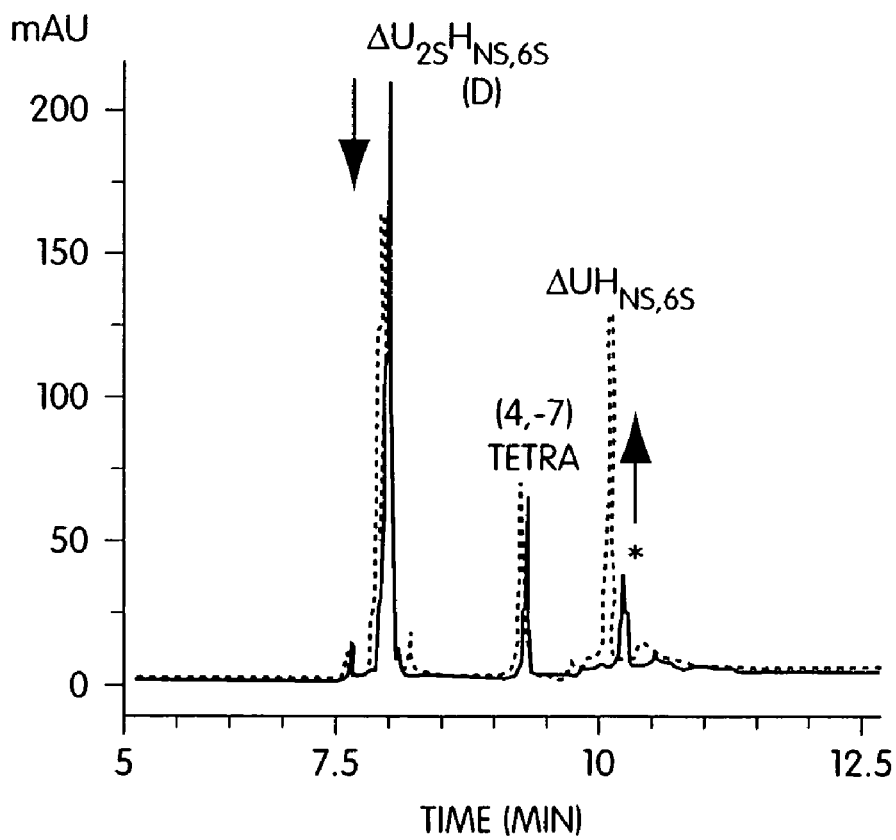

Exolytic Action of the 2-O sulfatase—We addressed this important question using as a substrate the purified heparin-derived AT-10 decasaccharide $\Delta U_{2S}H_{NS,6S}I_{2S}H_{NS,6S}I_{2S}H_{NS,6S}IH_{NAc,6S}GH_{NS,3S,6S}$. This oligosaccharide possesses a Δ 4,5 unsaturated uronic acid at the non-reducing end and both externally and internally positioned 2-O sulfates. The substrate was first exhaustively treated with the 2-O sulfatase. The 2-O desulfated decasaccharide was then subjected to an exhaustive heparinase treatment. CE-based compositional analyses indicated the disappearance of the disaccharide $\Delta U_{2S}H_{NS,6S}$ by only one-third; two-thirds of this trisulfated disaccharide remained after sequential treatment with the 2-O sulfatase and heparin lyases (FIG. 12). Loss of a single sulfate was independently determined by mass spectrometry. The loss of the single sulfate to the terminal 2-OH position is suggested given the fact that the internally positioned iduronic acid 2-O sulfates are structurally identical and should therefore possess the same potential for desulfation. Based on this assumption, the 2-O sulfatase would appear to act in an exolytic fashion. Our model clearly predicts a strong preference for sulfates positioned at the non-reducing end where these sulfates would not be constrained by the narrow topology of the enzyme active site.

The requirement for an unsaturated Δ 4,5 non-reducing terminus—In a related experiment, we assessed the ability of the 2-O sulfatase to hydrolyze size-fractionated hexasaccharides derived from the nitrous acid treatment of heparin. Unlike enzymatic cleavage, these chemically-derived heparin saccharides do not possess a Δ 4,5 unsaturated bond at their respective non-reducing ends. A majority of the resultant tetrasaccharides, however, do contain an $I_{2S}$ at this end. Using MALDI-MS, we were unable to detect any enzyme-dependent desulfation of treated hexasaccharides. This result strongly suggests a structural requirement for the Δ 4,5 bond. The rationale for this is described above in relation to our molecular modeling. In particular, the physical connection between this bond and the planar C5 carboxylate of the uronic acid carboxylate and how such a constraint permits critical enzyme-substrate interactions for the proper orientation of the 2-O sulfate within the enzyme active site was described.

Determination of disaccharide substrate kinetics and specificity—We were interested in ascertaining any kinetic discrimination the enzyme may possess for its disaccharide substrates based on the following structural considerations. 1) the number and position of sulfates on the adjoining hexosamine; 2) the glycosidic linkage position (i.e., β1→4 versus α1→3); and 3) glucosamine vs. galactosamine as the adjoining hexosamine. We examined substrate saturation kinetics measured under Michaelis-Menten conditions. For these experiments, several heparin disaccharide substrates were used, each with a uronic acid possessing a 2-O sulfate and a Δ 4,5 unsaturated bond at the non-reducing end, but differing in the degree of sulfation within the glucosamine. In addition the two unsaturated chondroitin disaccharides $\Delta U_{2S}Gal_{NAc,4S}$ and $\Delta U_{2S}Gal_{NAc,6S}$ were also examined as possible substrates. These latter two disaccharides differ from those derived from heparin/heparan sulfate in possessing a β1→3 glycosidic linkage and a galactosamine in place of a glucosamine. The results are summarized in FIG. 13 and Table 5. All of the heparin disaccharides examined were hydrolyzed at substantial rates that included $k_{cat}$ values which varied from approximately 600 to 1700 $sec^{-1}$. At the same time, the 2-O sulfatase did exhibit a substrate discrimination apparently based on the extent of sulfation and largely manifested as a $K_m$ effect. In particular, the presence of a 6-0 sulfate on the adjoining glucosamine conferred a significantly lower $K_m$ relative to its counterpart lacking such a sulfate ester. In terms of catalytic efficiency, the trisulfated disaccharide ($\Delta U_{2S}H_{NS,6S}$) was clearly the preferred substrate whereas the mono-sulfated disaccharide ($\Delta U_{2S}H_{NAc}$) was least preferred.

TABLE 5

2-O-sulfatase disaccharide substrate specificity

| Disaccharide | $k_{cat}$ (sec$^{-1}$) | $K_m$ (mM) | $k_{cat}/K_m$ |
|---|---|---|---|
| $\Delta U_{2S}H_{Nac,6S}$ | 1672 | 0.515 | 3247 |
| $\Delta U_{2S}H_{NS,6S}$ | 814 | 0.087 | 9356 |
| $\Delta U_{2S}H_{NS}$ | 911 | 1.06 | 859 |
| $\Delta U_{2S}H_{Nac}$ | 673 | 4.66 | 144 |
| $\Delta U_{2S}Gal_{Nac,6S}$* | <100 | >10 | N.D. |

Figure 13:
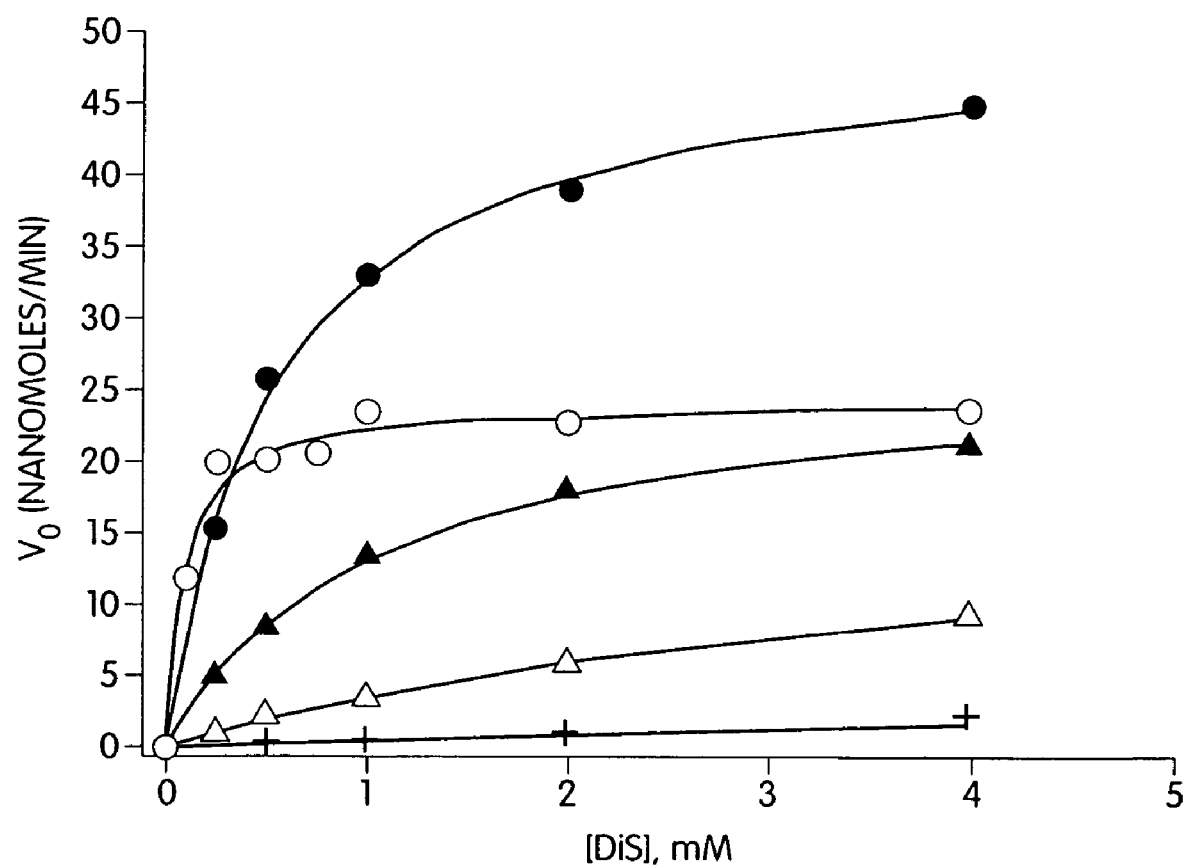
FIG. 13 illustrates the steady-state kinetics for various unsaturated disaccharide substrates. Panel (A) provides the initial rates determined using 25 nM enzyme under standard conditions. Substrate saturation data were fit to pseudo-first order Michaelis-Menten assumptions using a non-linear least squares analysis. $\Delta U_{2S}H_{Nac}$ (Δ); $\Delta U_{2S}H_{Nac,6S}$ (●); $\Delta U_{2S}H_{NS}$ (▲); $\Delta U_{2S}H_{NS,6S}$ (○); $\Delta U_{2S}Gal_{NAc,6S}$ (+).

Kinetic parameters were derived from a non-linear regressional analyses of substrate saturation data depicted in FIG. 13.
*Kinetic values for the unsaturated chondroitin disaccharide were approximated from double reciprocal plots.
N.D. not determined.

The 2-O sulfated chondroitin disaccharide $\Delta U_{2S}Gal_{NAc,6S}$ was only negligibly hydrolyzed under the same kinetic conditions. The enzyme did desulfate this disaccharide to an appreciable extent, however, under reaction conditions involving a 4× higher enzyme concentration and a longer incubation time. Under these conditions, approximately 40% of the substrate was desulfated over a 20 minute period. In contrast, less than 10% of chondroitin disaccharide $\Delta U_{2S}Gal_{NAc,4S}$ was hydrolyzed during the same time period. To determine whether either or both of these 2-O sulfated chondroitin disaccharides could be quantitatively desulfated under exhaustive conditions, we carried out an 18 hour incubation at 30° C. that included 5 mM of substrate and 5 µM enzyme. Under these conditions, both chondroitin disaccharides were greater than 95% desulfated at the 2-O position. This result indicates that while linkage position and/or hexosamine isomerization are discriminating kinetic factors, these physical parameters are not absolute determinants for 2-O sulfatase substrate recognition. It is interesting to consider this latter observation in the context of the lysosomal pathway for glycosaminoglycan degradation in mammals where one enzyme desulfates both chondroitin and HS oligosaccharides at this position.

The apparent kinetic discrimination described above points to an underlying structural determinant, namely a preference for glucosamine sulfated at the 6-OH and 2N positions. Our model does predict a favorable interaction with the 6-O sulfate in correct optimal orientation. At the same time, we would predict a bias in favor of acetylation of the N-position rather than sulfation due to potential hydrophobic interactions.

Figure 14:
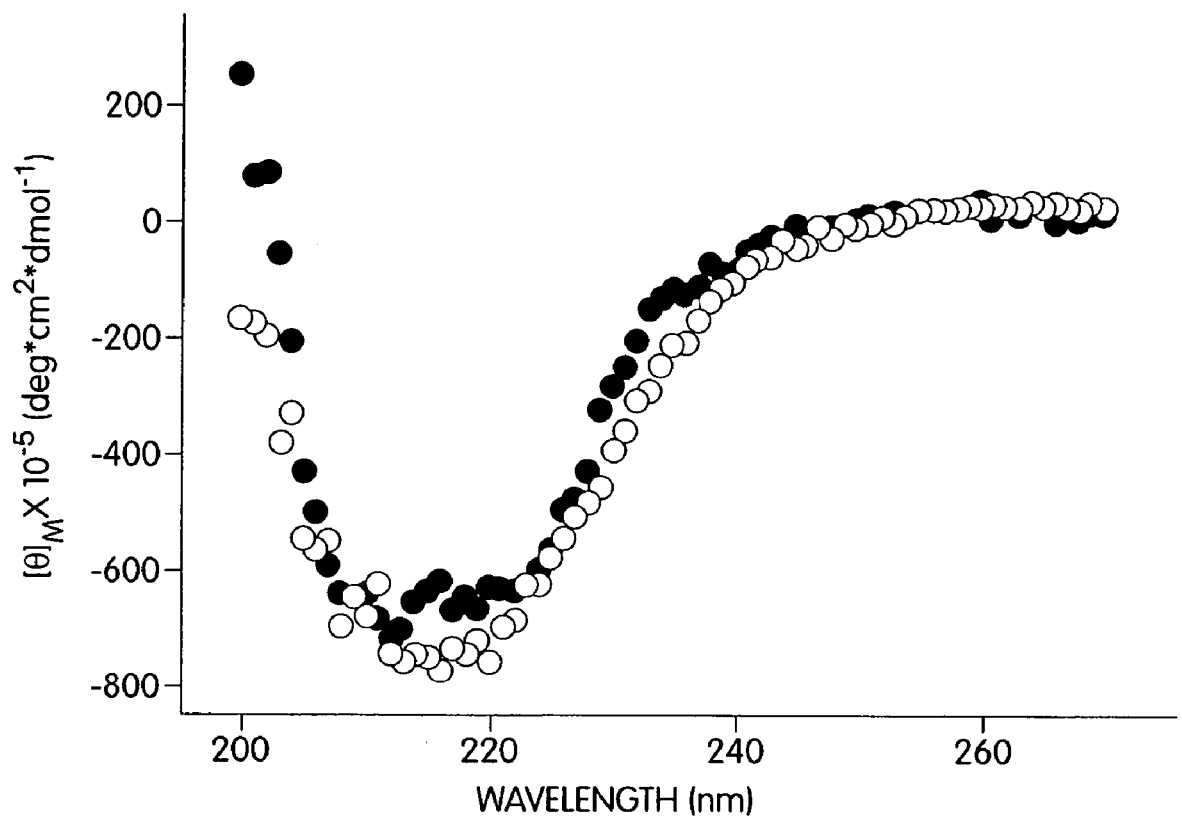
FIG. 14 provides the comparable CD spectroscopy of the wild-type 2-O $\Delta N^{1-24}$ sulfatase and C82A site-directed mutant—wild-type enzyme (●), C82A mutant (○). Band intensities are expressed as molar ellipticities with units indicated.

2-O sulfatase peptide mapping and chemical modification of active siteformylglycine—Finally, in describing the structure-function relationship of the 2-O sulfatase active site, we come to the central catalytic player itself—the formylglycine at position 82. The recombinant expression of catalytically active 2-O sulfatase in E. coli functionally argues for this covalent modification of the active site in vivo. We established the catalytic function of Cys 82 by site-directed mutagenesis. The mutant (C82A) was recombinantly expressed and purified as a histidine-tagged protein in the same manner employed for the wild-type enzyme. Comparable expression levels of soluble protein were achieved. The C82A mutant, however, was completely inactive. Both the wild-type and mutant possessed the same secondary structure as exhibited by their virtually superimposible CD spectra (FIG. 14), arguing against any adverse global conformational changes induced by the molecular replacement of the cysteine by alanine.

Figure 15A:
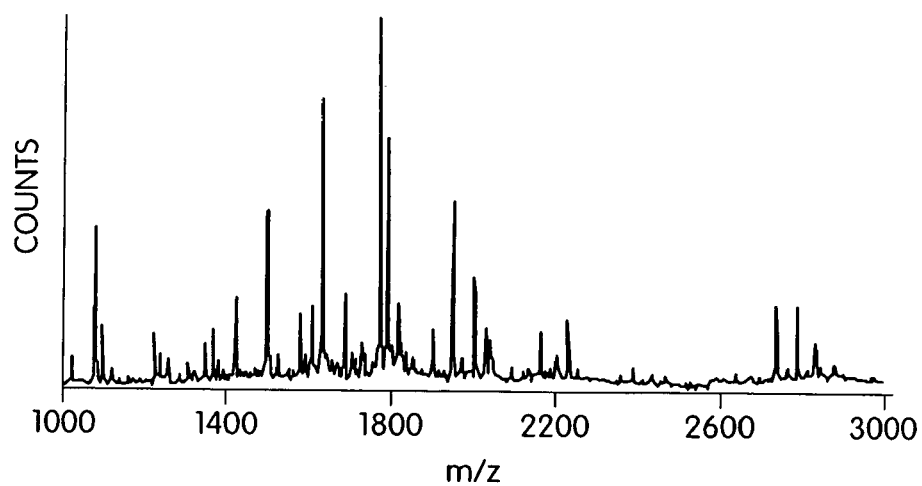
FIG. 15 illustrates the identification of 2-O sulfatase active site modification (FGly) by chemical labeling and mass spectrometry. Wild-type sulfatase (2-O $\Delta N^{1-24}$) and C82A mutant were reacted with Texas Red Hydrazide and subjected to trypsin proteolysis as described in Materials and Methods. The molecular masses of the resultant peptides were subsequently characterized by MALDI-MS. Panel (A) shows the unlabeled wild-type sulfatase control. Panel (B) shows the covalently labeled wild-type sulfatase. Panel (C) shows the C82A mutant refractory to chemical labeling. A unique molecular mass signature in Panel (B) is noted by an asterisk.
Figure 15B:
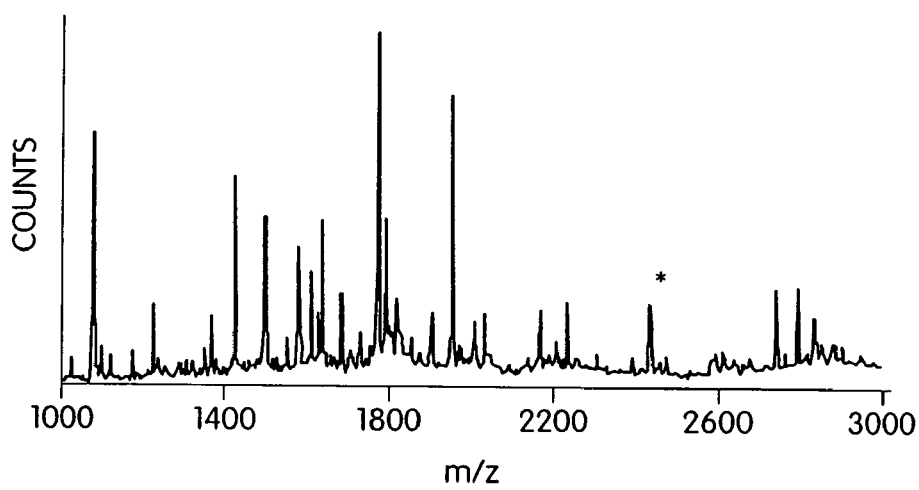
Figure 15C:
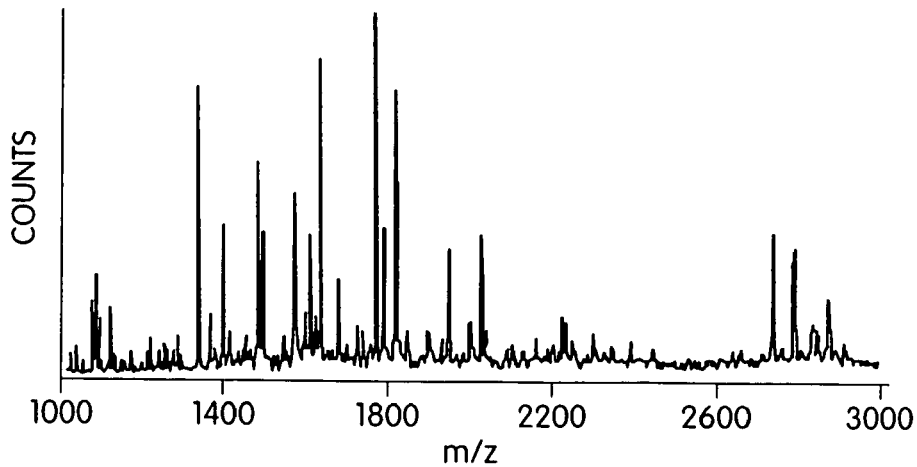

We also set out to demonstrate the physical presence of the FGly at position 82 by the tandem use of protein chemistry and mass spectrometry. 10 nanomoles of wild-type sulfatase (2-O ΔN$^{1-24}$) and the C82A mutant were reacted with Texas red hydrazide (620.74 Da) as described in Materials and Methods. The two sulfatase fractions were subsequently trypsinized under mildly denaturing conditions followed by reductive methylation of the unmodified cysteines. The molecular masses of the resultant peptides were determined by MALDI-MS (FIG. 15). In this experiment, we identified a single ionized species uniquely present in the labeled sulfatase experiment (FIG. 15, Panel (B)), but absent in the active site mutant (FIG. 15, Panel (C)) or in the unlabeled control (FIG. 15, Panel (A)). The empirical mass of this species corresponded most closely to the peptide sequence FTRAY-CAQPLCTPSR (SEQ ID NO: 37) resultant from a partial trypsin cleavage. This peptide contains the sulfatase consensus sequence CXPXR which includes the critical active site cysteine (denoted in bold) at position 82. The mass of this peptide is consistent with first the conversion of this cysteine to a formylglycine (FGly 82) followed by the covalent hydrazone linkage of the aldehyde-reactive fluorophore at this position. It also takes into account the carbamidomethylation of the second (unmodified) cysteine present in this peptide. These data, taken together with the loss of function observed for the C82A mutant, establish the important structure-function relationship for this active site modification.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method of degrading a glycosaminoglycan, comprising:
contacting a glycosaminoglycan with a recombinantly produced or isolated 2-O sulfatase that has the amino acid sequence set forth as SEQ ID NO: 2 or 4 in an effective amount to degrade the glycosaminoglycan.

2. The method of claim 1, wherein the 2-O sulfatase is recombinantly produced by expressing an isolated nucleic acid molecule selected from the group consisting of
(a) nucleic acid molecules which hybridize under stringent conditions to a nucleic acid molecule having a nucleotide sequence selected from the group consisting of nucleotide sequences set forth as SEQ ID NOs: 1 and 3,
(b) nucleic acid molecules that differ from the nucleic acid molecules of (a) in codon sequence due to degeneracy of the genetic code, and
(c) full complements of (a) or (b);
wherein the hybridization conditions are 1) hybridization at 65° C. in hybridization buffer that consists of 3.5 ×SSC, 0.02% Ficoll, 0.02% polyvinyl pyrrolidone, 0.02% Bovine Serum Albumin, 2.5mM NaH2PO4, pH 7, 0.5% sodium dodecyl sulphate (SDS), 2mM ethylenediaminetetracetic acid (EDTA), wherein SSC is 0.15M sodium chloride/0.015M sodium citrate, pH 7 and 2) washing in 2 ×SSC at room temperature and then in 0.1 ×SSC/0.1 ×SDS at 68° C.

3. The method of claim 1, further comprising;
contacting the glycosaminoglycan with at least one other glycosaminoglycan degrading enzyme.

4. The method of claim 3, wherein the at least one other glycosaminoglycan degrading enzyme is a heparinase or glycuronidase.

5. The method of claim 3, wherein the glycosaminoglycan is contacted with the at least one other glycosaminoglycan degrading enzyme concomitantly with the 2-O sulfatase.

6. The method of claim 5, wherein the at least one other glycosaminoglycan degrading enzyme is a glycuronidase.

7. The method of claim 4 or 6, wherein the glycuronidase is Δ4, 5 glycuronidase.

8. The method of claim 3, wherein the glycosaminoglycan is contacted with the at least one other glycosaminoglycan degrading enzyme prior to or subsequent to contacting the glycosaminoglycan with the 2-O sulfatase.

9. The method of claim 8, wherein the glycosaminoglycan is contacted with the at least one other glycosaminoglycan degrading enzyme prior to contacting the glycosaminoglycan with the 2-O sulfatase, and wherein the at least one other glycosaminoglycan degrading enzyme is a heparinase.

10. The method of claim 4 or 9, wherein the heparinase is heparinase I, heparinase II or heparinase III.

11. The method of claim 1, wherein the glycosaminoglycan contains a 2-O sulfated uronic acid at the non-reducing end.

12. The method of claim 1, wherein the glycosaminoglycan is a highly sulfated glycosaminoglycan.

13. The method of claim 12, wherein the highly sulfated glycosaminoglycan contains a 6-O sulfated glucosamine.

14. The method of claim 12, wherein the highly sulfated glycosaminoglycan contains a glucosamine sulfated at the N-position.

15. The method of claim 1, wherein the glycosaminoglycan contains a β1 →4 linkage.

16. The method of claim 1, wherein the glycosaminoglycan contains $\Delta U_{2S}H_{NS,6S}$.

17. The method of claim 1, wherein the glycosaminoglycan contains $I_{2S}H_{NS,6S}$.

18. The method of claim 1, wherein the glycosaminoglycan contains $\Delta U_{2S}H_{NS}$.

19. The method of claim 1, wherein the glycosaminoglycan contains $\Delta U_{2S}H_{NAc,6S}$.

20. The method of claim 1, wherein the glycosaminoglycan contains $\Delta U_{2S}H_{NAc}$.

21. The method of claim 1, wherein the glycosaminoglycan contains $\Delta U_{2S}H_{NS,6S}I_{2S}H_{NS,6S}$.

22. The method of claim 1, wherein the glycosaminoglycan contains $\Delta U_{2S}H_{NS,6S}I_{2S}H_{NS,6S}I_{2S}H_{NS,6S}IH_{NAc,6S}GH_{NS,3S,6S}$.

23. The method of claim 1, wherein the glycosaminoglycan is a tetrasaccharide.

24. The method of claim 1, wherein the glycosaminoglycan is a decasaccharide.

25. The method of claim 1, wherein the glycosaminoglycan is a heparin, low molecular weight heparin (LMWH) or heparan sulfate.

26. The method of claim 1, wherein the glycosaminoglycan is cleaved.

27. The method of claim 1, wherein the 2-O sulfatase is immobilized on a solid support.

28. The method of claim 3, wherein the at least one other glycosaminoglycan degrading enzyme is immobilized on a solid support.

29. A method of degrading a glycosaminoglycan, comprising:
  contacting a glycosaminoglycan with a recombinantly produced 2-O sulfatase in an effective amount to degrade the glycosaminoglycan, wherein the 2-O sulfatase is recombinantly produced by expressing an isolated nucleic acid molecule selected from the group consisting of:
  (a) nucleic acid molecules which hybridize under stringent conditions to a nucleic acid molecule having the nucleotide sequence selected from the group consisting of nucleotide sequences set forth as SEQ ID NOs: 1 and 3,
  (b) nucleic acid molecules that differ from the nucleic acid molecules of (a) in codon sequence due to degeneracy of the genetic code, and
  (c) fill complements of (a) or (b);
  wherein the hybridization conditions are 1) hybridization at 65° C. in hybridization buffer that consists of 3.5 ×SSC, 0.02% Ficoll, 0.02% polyvinyl pyrrolidone, 0.02% Bovine Serum Albumin, 2.5mM NaH2PO4, pH 7, 0.5% sodium dodecyl sulphate (SDS), 2mM ethylenediaminetetracetic acid (EDTA), wherein SSC is 0.15M sodium chloride/0.015M sodium citrate, pH 7 and 2) washing in 2 ×SSC at room temperature and then in 0.1 ×SSC/0.1 ×SDS at 68° C.

30. The method of claim 1, wherein degrading the glycosaminoglycan produces $\Delta UH_{NS,6S}$.

31. The method of claim 3, wherein the at least one other glycosaminoglycan degrading enzyme is heparinase I, II and III and Δ4, 5 glycuronidase, and wherein $\Delta U_{2S}H_{NS,6S}$; $\Delta UH_{NAc,6S}GH_{NS,3S,6S}$; $\Delta U_{2S}H_{NS}$, $\Delta UH_{NS,6S}$; $\Delta U_{2S}H_{NAc,6S}$; $\Delta UH_{NS}$; $\Delta U_{2S}H_{NAc}$ and $\Delta UH_{NAc,6S}$ is produced.

32. The method of claim 3, wherein the at least one other glycosaminoglycan degrading enzyme is heparinase I, II and III, and wherein $\Delta U_{2S}H_{NS,6S}$; $\Delta U_{2S}H_{NS}$; $\Delta UH_{NS,6S}$; $\Delta U_{2S}H_{NAc,6S}$ and $\Delta U_{2S}H_{NAc}$ is produced.

* * * * *

UNITED STATES PATENT AND TRADEMARK OFFICE
CERTIFICATE OF CORRECTION

PATENT NO. : 7,504,247 B2
APPLICATION NO. : 11/433340
DATED : March 17, 2009
INVENTOR(S) : Ram Sasisekharan et al.

It is certified that error appears in the above-identified patent and that said Letters Patent is hereby corrected as shown below:

At column 81, claim 2, line 65, delete "having a" and insert --having the--

At column 82, claim 3, line 65, delete "comprising;" and insert --comprising:--

At column 84, claim 29, line 28, delete "fill" and insert --full--

At column 84, claim 31, line 43, delete "$\Delta U_{2S}H_{NS}$," and insert --$\Delta U_{2S}H_{NS}$;--

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,504,247 B2
APPLICATION NO.  : 11/433340
DATED            : March 17, 2009
INVENTOR(S)      : Ram Sasisekharan et al.

It is certified that error appears in the above-identified patent and that said Letters Patent is hereby corrected as shown below:

At column 1, lines 18-21, please delete

"Aspects of the invention may have been made using funding from National Institutes of Health Grants GM 57073 and CA90940. Accordingly, the Government may have rights in the invention."

and insert

-- This invention was made with government support under Grant No. R01 GM57073, awarded by the National Institutes of Health. The government has certain rights in this invention. --

Signed and Sealed this
Third Day of May, 2011

David J. Kappos
*Director of the United States Patent and Trademark Office*

SEQUENCE LISTING

```
<160> NUMBER OF SEQ ID NOS: 39

<210> SEQ ID NO 1
<211> LENGTH: 1395
<212> TYPE: DNA
<213> ORGANISM: Flavobacterium heparinum

<400> SEQUENCE: 1
atgaagatgt acaaatcgaa aggctggttg atagccatgc ttatacttgc aggttttgga      60
gatgcagggg cgcaaacctc aaaagtagca gcttccaggc ctaacatcat tatcatcatg     120
acagatcagc aaacagctga tgccatgagc aatgctggta ataaggacct gcatacacct     180
gcaatggatg ttttggctgc aaacggtacc cgttttacac gtgcctattg tgcccagccg     240
ctctgtacac cttcacgctc cgcgatattt agcggaaaaa tgccacatga aaccggcttt     300
acggggaata caccggaaaa ggacggacag tggcccgatt ctgtgctgat gatgggcaaa     360
atatttaagg caggaggcta taaaaccggc tacgtcggaa aatggcacct gcctgttcct     420
gttactaaag tagcacaaca tggatttgag actattgaga atacaggtat gggcgattat     480
accgatgcag ttaccccatc gcaatgcgcc aacttcaata aaaagaataa agacaaccca     540
tttttactgg tagcatcctt tttgaaccca cacgatattt gtgaatgggc aagggtgat       600 aatttgaaaa tggatgttct ggatgcagcg ccggatacag catttgtcc gaaattacct       660 gccaactggc caattccggc ttttgagcct gccattgtaa gggaacagca aaaggtgaac      720
ccgcgtactt atccttcggt aggctggaac gaaagccagt ggcgcaaata ccgctgggcc     780
tataaccgcc tggtagagaa ggtagacaat tatatggcca tggtattggg ttcgttaaaa     840
aaatatggta tagaagacaa taccatcatc atctttacca gcgatcatgg tgatggttat     900
gcggcacatg agtggaacca gaagcagatt ttgtatgagg aggctgccag gataccttt       960 atcatctcga agatcggaca atggaaagcc agaaccgatg atcagctggt ttgcaatggc    1020
atcgatatta tccccaccat atgtggcttt gccggaattg ctaaacctgt tggtttaaaa    1080
ggcctggatt taagtaaacg tattgccaac ccttcggtta aactacggga tactttagtg    1140
atagaaaccg attttgctga taacgaactg ttgctgggta ttaagggcag ggcagtgatt    1200
accaaagatt ttaaatacat tgtttatgac aagggggaga tccgggaaca attgtttgac    1260
ctggaaaaag acgcaggaga aatggataac ctggctgtta aacccgccta taaaaagaaa    1320
ttgaatgaaa tgcgcgctta cctgaaacta tggtgtaaac agcaccagga ttcgttttat    1380
```
gcattaaaaa aataa                                                           1395

<210> SEQ ID NO 2
<211> LENGTH: 464
<212> TYPE: PRT
<213> ORGANISM: Flavobacterium heparinum

<400> SEQUENCE: 2

Met Lys Met Tyr Lys Ser Lys Gly Trp Leu Ile Ala Met Leu Ile Leu
1               5                   10                  15

Ala Gly Phe Gly Asp Ala Gly Ala Gln Thr Ser Lys Val Ala Ala Ser
            20                  25                  30

Arg Pro Asn Ile Ile Ile Met Thr Asp Gln Gln Thr Ala Asp Ala
        35                  40                  45

Met Ser Asn Ala Gly Asn Lys Asp Leu His Thr Pro Ala Met Asp Val
    50                  55                  60

Leu Ala Ala Asn Gly Thr Arg Phe Thr Arg Ala Tyr Cys Ala Gln Pro
65                  70                  75                  80

Leu Cys Thr Pro Ser Arg Ser Ala Ile Phe Ser Gly Lys Met Pro His
                85                  90                  95

Glu Thr Gly Phe Thr Gly Asn Thr Pro Glu Lys Asp Gly Gln Trp Pro
            100                 105                 110

Asp Ser Val Leu Met Met Gly Lys Ile Phe Lys Ala Gly Tyr Lys
            115                 120                 125

Thr Gly Tyr Val Gly Lys Trp His Leu Pro Val Pro Val Thr Lys Val
    130                 135                 140

Ala Gln His Gly Phe Glu Thr Ile Glu Asn Thr Gly Met Gly Asp Tyr
145                 150                 155                 160

Thr Asp Ala Val Thr Pro Ser Gln Cys Ala Asn Phe Asn Lys Lys Asn
                165                 170                 175

Lys Asp Asn Pro Phe Leu Leu Val Ala Ser Phe Leu Asn Pro His Asp
            180                 185                 190

Ile Cys Glu Trp Ala Arg Gly Asp Asn Leu Lys Met Asp Val Leu Asp
        195                 200                 205

Ala Ala Pro Asp Thr Ala Phe Cys Pro Lys Leu Pro Ala Asn Trp Pro
    210                 215                 220

Ile Pro Ala Phe Glu Pro Ala Ile Val Arg Glu Gln Gln Lys Val Asn
225                 230                 235                 240

Pro Arg Thr Tyr Pro Ser Val Gly Trp Asn Glu Ser Gln Trp Arg Lys
                245                 250                 255

Tyr Arg Trp Ala Tyr Asn Arg Leu Val Glu Lys Val Asp Asn Tyr Met
            260                 265                 270

Ala Met Val Leu Gly Ser Leu Lys Lys Tyr Gly Ile Glu Asp Asn Thr
        275                 280                 285

Ile Ile Ile Phe Thr Ser Asp His Gly Asp Gly Tyr Ala Ala His Glu
    290                 295                 300

Trp Asn Gln Lys Gln Ile Leu Tyr Glu Glu Ala Ala Arg Ile Pro Phe
305                 310                 315                 320

Ile Ile Ser Lys Ile Gly Gln Trp Lys Ala Arg Thr Asp Asp Gln Leu
                325                 330                 335

Val Cys Asn Gly Ile Asp Ile Ile Pro Thr Ile Cys Gly Phe Ala Gly
            340                 345                 350

Ile Ala Lys Pro Val Gly Leu Lys Gly Leu Asp Leu Ser Lys Arg Ile
        355                 360                 365

Ala Asn Pro Ser Val Lys Leu Arg Asp Thr Leu Val Ile Glu Thr Asp
    370                 375                 380

Phe Ala Asp Asn Glu Leu Leu Leu Gly Ile Lys Gly Arg Ala Val Ile
385                 390                 395                 400

Thr Lys Asp Phe Lys Tyr Ile Val Tyr Asp Lys Gly Glu Ile Arg Glu
                405                 410                 415

Gln Leu Phe Asp Leu Glu Lys Asp Ala Gly Glu Met Asp Asn Leu Ala
            420                 425                 430

Val Lys Pro Ala Tyr Lys Lys Leu Asn Glu Met Arg Ala Tyr Leu
        435                 440                 445

Lys Leu Trp Cys Lys Gln His Gln Asp Ser Phe Tyr Ala Leu Lys Lys
    450                 455                 460

<210> SEQ ID NO 3
<211> LENGTH: 1323
<212> TYPE: DNA
<213> ORGANISM: Flavobacterium heparinum

<400> SEQUENCE: 3
caaacctcaa aagtagcagc ttccaggcct aacatcatta tcatcatgac agatcagcaa     60
acagctgatg ccatgagcaa tgctggtaat aaggacctgc atacacctgc aatggatgtt    120
ttggctgcaa acggtacccg ttttacacgt gcctattgtg cccagccgct ctgtacacct    180
tcacgctccg cgatatttag cggaaaaatg ccacatgaaa ccggctttac ggggaataca    240
ccggaaaagg acgacagtg gcccgattct gtgctgatga tgggcaaaat atttaaggca    300
ggaggctata aaaccggcta cgtcggaaaa tggcacctgc ctgttcctgt tactaaagta    360
gcacaacatg gatttgagac tattgagaat acaggtatgg gcgattatac cgatgcagtt    420
accccatcgc aatgcgccaa cttcaataaa aagaataaag acaacccatt tttactggta    480 gcatccttt tgaacccaca cgatatttgt gaatgggcaa ggggtgataa tttgaaaatg    540
gatgttctgg atgcagcgcc ggatacagca ttttgtccga aattacctgc caactggcca    600
attccggctt ttgagcctgc cattgtaagg gaacagcaaa aggtgaaccc gcgtacttat    660
ccttcggtag gctggaacga aagccagtgg cgcaaatacc gctgggccta taaccgcctg    720
gtagagaagg tagacaatta tatggccatg gtattgggtt cgttaaaaaa atatggtata    780
gaagacaata ccatcatcat ctttaccagc gatcatggtg atggttatgc ggcacatgag    840
tggaaccaga agcagatttt gtatgaggag gctgccagga tacctttat catctcgaag    900 atcggacaat ggaaagccag aaccgatgat cagctggttt gcaatggcat cgatattatc    960
cccaccatat gtggctttgc cggaattgct aaacctgttg gttaaaaagg cctggattta   1020
agtaaacgta ttgccaaccc ttcggttaaa ctacgggata ctttagtgat agaaaccgat   1080
tttgctgata cgaactgtt gctgggtatt aagggcaggg cagtgattac caaagatttt   1140
aaatacattg tttatgacaa gggggagatc cgggaacaat gtttgaccct ggaaaaagac   1200
gcaggagaaa tggataacct ggctgttaaa cccgcctata aaagaaatt gaatgaaatg   1260 cgcgcttacc tgaaactatg gtgtaaacag caccaggatt cgttttatgc attaaaaaaa   1320
taa                                                                  1323

<210> SEQ ID NO 4
<211> LENGTH: 440
<212> TYPE: PRT
<213> ORGANISM: Flavobacterium heparinum

```
<400> SEQUENCE: 4

Gln Thr Ser Lys Val Ala Ala Ser Arg Pro Asn Ile Ile Ile Met
1               5                   10                  15

Thr Asp Gln Gln Thr Ala Asp Ala Met Ser Asn Ala Gly Asn Lys Asp
            20                  25                  30

Leu His Thr Pro Ala Met Asp Val Leu Ala Ala Asn Gly Thr Arg Phe
            35                  40                  45

Thr Arg Ala Tyr Cys Ala Gln Pro Leu Cys Thr Pro Ser Arg Ser Ala
50                  55                  60

Ile Phe Ser Gly Lys Met Pro His Glu Thr Gly Phe Thr Gly Asn Thr
65                  70                  75                  80

Pro Glu Lys Asp Gly Gln Trp Pro Asp Ser Val Leu Met Met Gly Lys
                85                  90                  95

Ile Phe Lys Ala Gly Gly Tyr Lys Thr Gly Tyr Val Gly Lys Trp His
            100                 105                 110

Leu Pro Val Pro Val Thr Lys Val Ala Gln His Gly Phe Glu Thr Ile
            115                 120                 125

Glu Asn Thr Gly Met Gly Asp Tyr Thr Asp Ala Val Thr Pro Ser Gln
130                 135                 140

Cys Ala Asn Phe Asn Lys Lys Asn Lys Asp Asn Pro Phe Leu Leu Val
145                 150                 155                 160

Ala Ser Phe Leu Asn Pro His Asp Ile Cys Glu Trp Ala Arg Gly Asp
                165                 170                 175

Asn Leu Lys Met Asp Val Leu Asp Ala Ala Pro Asp Thr Ala Phe Cys
            180                 185                 190

Pro Lys Leu Pro Ala Asn Trp Pro Ile Pro Ala Phe Glu Pro Ala Ile
            195                 200                 205

Val Arg Glu Gln Gln Lys Val Asn Pro Arg Thr Tyr Pro Ser Val Gly
210                 215                 220

Trp Asn Glu Ser Gln Trp Arg Lys Tyr Arg Trp Ala Tyr Asn Arg Leu
225                 230                 235                 240

Val Glu Lys Val Asp Asn Tyr Met Ala Met Val Leu Gly Ser Leu Lys
                245                 250                 255

Lys Tyr Gly Ile Glu Asp Asn Thr Ile Ile Ile Phe Thr Ser Asp His
            260                 265                 270

Gly Asp Gly Tyr Ala Ala His Glu Trp Asn Gln Lys Gln Ile Leu Tyr
            275                 280                 285

Glu Glu Ala Ala Arg Ile Pro Phe Ile Ile Ser Lys Ile Gly Gln Trp
290                 295                 300

Lys Ala Arg Thr Asp Asp Gln Leu Val Cys Asn Gly Ile Asp Ile Ile
305                 310                 315                 320

Pro Thr Ile Cys Gly Phe Ala Gly Ile Ala Lys Pro Val Gly Leu Lys
                325                 330                 335

Gly Leu Asp Leu Ser Lys Arg Ile Ala Asn Pro Ser Val Lys Leu Arg
            340                 345                 350

Asp Thr Leu Val Ile Glu Thr Asp Phe Ala Asp Asn Glu Leu Leu Leu
            355                 360                 365

Gly Ile Lys Gly Arg Ala Val Ile Thr Lys Asp Phe Lys Tyr Ile Val
370                 375                 380

Tyr Asp Lys Gly Glu Ile Arg Glu Gln Leu Phe Asp Leu Glu Lys Asp
385                 390                 395                 400

Ala Gly Glu Met Asp Asn Leu Ala Val Lys Pro Ala Tyr Lys Lys Lys
                405                 410                 415
```

Leu Asn Glu Met Arg Ala Tyr Leu Lys Leu Trp Cys Lys Gln His Gln
            420                 425                 430

Asp Ser Phe Tyr Ala Leu Lys Lys
        435                 440

<210> SEQ ID NO 5
<211> LENGTH: 11
<212> TYPE: PRT
<213> ORGANISM: Artificial Sequence
<220> FEATURE:
<223> OTHER INFORMATION: Synthetic Sulfatase Consensus Sequence
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (4)..(4)
<223> OTHER INFORMATION: Xaa=any amino acid
<220> FEATURE:
<221> NAME/KEY: MISC_FEATURE
<222> LOCATION: (6)..(9)
<223> OTHER INFORMATION: Xaa=any amino acid
<220> FEATURE:
<221> NAME/KEY: MISC_FEATURE
<222> LOCATION: (10)..(10)
<223> OTHER INFORMATION: Xaa=serine or threonine

<400> SEQUENCE: 5

Cys Xaa Pro Xaa Arg Xaa Xaa Xaa Xaa Xaa Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Sulfatase Consensus Sequence
<220> FEATURE:
<221> NAME/KEY: MISC_FEATURE
<222> LOCATION: (1)..(1)
<223> OTHER INFORMATION: Xaa=cysteine or serine
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (4)..(4)
<223> OTHER INFORMATION: Xaa=any amino acid
<220> FEATURE:
<221> NAME/KEY: MISC_FEATURE
<222> LOCATION: (6)..(9)
<223> OTHER INFORMATION: Xaa=any amino acid
<220> FEATURE:
<221> NAME/KEY: MISC_FEATURE
<222> LOCATION: (10)..(10)
<223> OTHER INFORMATION: Xaa=serine or threonine

<400> SEQUENCE: 6

Xaa Xaa Pro Xaa Arg Xaa Xaa Xaa Xaa Xaa Gly
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic Putative Consensus Sequence
<220> FEATURE:
<221> NAME/KEY: MISC_FEATURE
<222> LOCATION: (5)..(5)

```
<223> OTHER INFORMATION: Xaa=any hydrophobic amino acid

<400> SEQUENCE: 7

Gly Lys Trp His Xaa
1               5

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 8
athgayatha thccnacnat h                                         21

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 9
datngtytca ttnccrtgyt g                                         21

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
catacacgta tgggcgatta t                                         21

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
gatgtgggga tgatgtcgat                                           20

<210> SEQ ID NO 12
<211> LENGTH: 35
<212> TYPE: DNA
<213> ORGANISM: Artificial Sequence
<220> FEATURE:
<223> OTHER INFORMATION: Synthetic Oligonucleotide
```

```
<400> SEQUENCE: 12
tgttctagac atatgaagat gtacaaatcg aaagg                              35

<210> SEQ ID NO 13
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 13
gtctcgagga tccttatttt tttaatgcat aaaacgaatc c                       41

<210> SEQ ID NO 14
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 14
gatattatcc ccaccatctg tggctttgcc ggaa                               34

<210> SEQ ID NO 15
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 15
ttccggcaaa gccacagatg gtggggataa tatc                               34

<210> SEQ ID NO 16
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 16
tctagacata tgcaaacctc aaaagtagca gct                                33

<210> SEQ ID NO 17
<211> LENGTH: 12
<212> TYPE: PRT
<213> ORGANISM: Flavobacterium heparinum

<400> SEQUENCE: 17

Met Gln Thr Ser Lys Val Ala Ala Ser Arg Pro Asn
1               5                   10

<210> SEQ ID NO 18
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 18
tctagacata tgcaaacctc aaaagtagca gct                                33

<210> SEQ ID NO 19
<211> LENGTH: 41
<212> TYPE: DNA
```

```
<210> SEQ ID NO 19
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 19
gtctcgagga tccttatttt tttaatgcat aaaacgaatc c          41

<210> SEQ ID NO 20
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 20
ccagccgctc gctacacctt cacg                            24

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 21
cgtgaaggtg tagcgagcgg ctgg                            24

<210> SEQ ID NO 22
<211> LENGTH: 10
<212> TYPE: PRT
<213> ORGANISM: Flavobacterium heparinum

<400> SEQUENCE: 22

Tyr Ile Val Tyr Asp Lys Gly Glu Ile Arg
1               5                   10

<210> SEQ ID NO 23
<211> LENGTH: 13
<212> TYPE: PRT
<213> ORGANISM: Flavobacterium heparinum

<400> SEQUENCE: 23

Thr Tyr Pro Ser Val Gly Trp Asn Glu Ser Gln Trp Arg
1               5                   10

<210> SEQ ID NO 24
<211> LENGTH: 28
<212> TYPE: PRT
<213> ORGANISM: Flavobacterium heparinum

<400> SEQUENCE: 24

Lys Met Pro His Glu Thr Gly Phe Thr Gly Asn Thr Pro Glu Lys Asp
1               5                   10                  15

Gly Gln Trp Pro Asp Ser Val Leu Met Met Gly Lys
            20                  25

<210> SEQ ID NO 25
<211> LENGTH: 31
<212> TYPE: PRT
<213> ORGANISM: Flavobacterium heparinum

<400> SEQUENCE: 25

Val Ala Gln His Gly Phe Glu Thr Ile Glu Asn Thr Gly Met Gly Asp
1               5                   10                  15
```

```
Tyr Thr Asp Ala Val Thr Pro Ser Gln Cys Ala Asn Phe Asn Lys
            20                  25                  30

<210> SEQ ID NO 26
<211> LENGTH: 24
<212> TYPE: PRT
<213> ORGANISM: Flavobacterium heparinum

<400> SEQUENCE: 26

Thr Asp Asp Gln Leu Val Cys Asn Gly Ile Asp Ile Ile Pro Thr Ile
1               5                   10                  15

Cys Gly Phe Ala Gly Ile Ala Lys
            20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is a, c, g, or t

<400> SEQUENCE: 27
tayathgtnt aygayaargg                                                  20

<210> SEQ ID NO 28
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 28
nccyttrtcr tanacdatrt a                                                21

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 29
carcayggnt tygaracnat                                                  20

<210> SEQ ID NO 30
<211> LENGTH: 21
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 30
datngtytca ttnccrtgyt g                                              21

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is a, c, g, or t

<400> SEQUENCE: 31
tayathgtnt aygayaargg                                                20

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 32
nccyttrtan acdatrta                                                  18

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 33
athgayatha thccnacnat                                                20

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 34
datngtnggd atdatrtcda t                                            21

<210> SEQ ID NO 35
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 35
gayathathc cnacnathtg ytt                                          23

<210> SEQ ID NO 36
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 36
aarcadatng tnggdatdat rtc                                          23

<210> SEQ ID NO 37
<211> LENGTH: 15
<212> TYPE: PRT
<213> ORGANISM: Flavobacterium heparinum

<400> SEQUENCE: 37

Phe Thr Arg Ala Tyr Cys Ala Gln Pro Leu Cys Thr Pro Ser Arg
1               5                   10                  15

<210> SEQ ID NO 38
<211> LENGTH: 1407
<212> TYPE: DNA
<213> ORGANISM: Flavobacterium heparinum

<400> SEQUENCE: 38
agtaaacata acatgaagat gtacaaatcg aaaggctggt tgatagccat gcttatactt    60
gcaggttttg gagatgcagg ggcgcaaacc tcaaaagtag cagcttccag gcctaacatc   120
attatcatca tgacagatca gcaaacagct gatgccatga gcaatgctgg taataaggac   180
ctgcatacac ctgcaatgga tgttttggct gcaaacggta cccgttttac acgtgcctat   240
tgtgcccagc cgctctgtac accttcacgc tccgcgatat ttagcggaaa aatgccacat   300
```

```
gaaaccggct tacgggaa tacaccggaa aaggacggac agtggcccga ttctgtgctg    360
atgatgggca aaatatttaa ggcaggaggc tataaaaccg gctacgtcgg aaaatggcac    420
ctgcctgttc ctgttactaa agtagcacaa catggatttg agactattga aatacaggt    480 atgggcgatt ataccgatgc agttacccca tcgcaatgcg ccaacttcaa taaaaagaat    540
aaagacaacc cattttact ggtagcatcc tttttgaacc cacacgatat ttgtgaatgg    600
gcaaggggtg ataatttgaa atggatgtt ctggatgcag cgccggatac agcattttgt    660
ccgaaattac ctgccaactg gccaattccg gcttttgagc ctgccattgt aagggaacag    720
caaaaggtga acccgcgtac ttatccttcg gtaggctgga acgaaagcca gtggcgcaaa    780
taccgctggg cctataaccg cctggtagag aaggtagaca attatatggc catggtattg    840
ggttcgttaa aaaaatatgg tatagaagac aataccatca tcatctttac cagcgatcat    900
ggtgatggtt atgcggcaca tgagtggaac cagaagcaga ttttgtatga ggaggctgcc    960 aggataccc tttatcatctc gaagatcgga caatggaaag ccagaaccga tgatcagctg   1020
gtttgcaatg gcatcgatat tatccccacc atatgtggct ttgccggaat tgctaaacct   1080 gttggttaa aaggcctgga tttaagtaaa cgtattgcca acccttcggt taaactacgg   1140
gatactttag tgatagaaac cgattttgct gataacgaac tgttgctggg tattaagggc   1200
agggcagtga ttaccaaaga ttttaaatac attgtttatg acaaggggga gatccgggaa   1260
caattgttgg acctggaaaa agacgcagga gaaatggata acctggctgt taaacccgcc   1320
tataaaaaga aattgaatga aatgcgcgct tacctgaaac tatggtgtaa acagcaccag   1380
gattcgtttt atgcattaaa aaataa                                        1407
```

<210> SEQ ID NO 39
<211> LENGTH: 468
<212> TYPE: PRT
<213> ORGANISM: Flavobacterium heparinum

<400> SEQUENCE: 39

Ser Lys His Asn Met Lys Met Tyr Lys Ser Lys Gly Trp Leu Ile Ala
1               5                   10                  15

Met Leu Ile Leu Ala Gly Phe Gly Asp Ala Gly Ala Gln Thr Ser Lys
            20                  25                  30

Val Ala Ala Ser Arg Pro Asn Ile Ile Ile Met Thr Asp Gln Gln
        35                  40                  45

Thr Ala Asp Ala Met Ser Asn Ala Gly Asn Lys Asp Leu His Thr Pro
    50                  55                  60

Ala Met Asp Val Leu Ala Ala Asn Gly Thr Arg Phe Thr Arg Ala Tyr
65                  70                  75                  80

Cys Ala Gln Pro Leu Cys Thr Pro Ser Arg Ser Ala Ile Phe Ser Gly
                85                  90                  95

Lys Met Pro His Glu Thr Gly Phe Thr Gly Asn Thr Pro Glu Lys Asp
            100                 105                 110

Gly Gln Trp Pro Asp Ser Val Leu Met Met Gly Lys Ile Phe Lys Ala
        115                 120                 125

Gly Gly Tyr Lys Thr Gly Tyr Val Gly Lys Trp His Leu Pro Val Pro
    130                 135                 140

Val Thr Lys Val Ala Gln His Gly Phe Glu Thr Ile Glu Asn Thr Gly
145                 150                 155                 160

Met Gly Asp Tyr Thr Asp Ala Val Thr Pro Ser Gln Cys Ala Asn Phe
                165                 170                 175

```
Asn Lys Lys Asn Lys Asp Asn Pro Phe Leu Leu Val Ala Ser Phe Leu
            180             185                 190

Asn Pro His Asp Ile Cys Glu Trp Ala Arg Gly Asp Asn Leu Lys Met
        195             200                 205

Asp Val Leu Asp Ala Ala Pro Asp Thr Ala Phe Cys Pro Lys Leu Pro
    210             215                 220

Ala Asn Trp Pro Ile Pro Ala Phe Glu Pro Ala Ile Val Arg Glu Gln
225             230             235                 240

Gln Lys Val Asn Pro Arg Thr Tyr Pro Ser Val Gly Trp Asn Glu Ser
            245             250                 255

Gln Trp Arg Lys Tyr Arg Trp Ala Tyr Asn Arg Leu Val Glu Lys Val
            260             265                 270

Asp Asn Tyr Met Ala Met Val Leu Gly Ser Leu Lys Lys Tyr Gly Ile
        275             280                 285

Glu Asp Asn Thr Ile Ile Ile Phe Thr Ser Asp His Gly Asp Gly Tyr
    290             295                 300

Ala Ala His Glu Trp Asn Gln Lys Gln Ile Leu Tyr Glu Glu Ala Ala
305             310             315                 320

Arg Ile Pro Phe Ile Ile Ser Lys Ile Gly Gln Trp Lys Ala Arg Thr
                325             330                 335

Asp Asp Gln Leu Val Cys Asn Gly Ile Asp Ile Ile Pro Thr Ile Cys
            340             345                 350

Gly Phe Ala Gly Ile Ala Lys Pro Val Gly Leu Lys Gly Leu Asp Leu
            355             360                 365

Ser Lys Arg Ile Ala Asn Pro Ser Val Lys Leu Arg Asp Thr Leu Val
    370             375                 380

Ile Glu Thr Asp Phe Ala Asp Asn Glu Leu Leu Leu Gly Ile Lys Gly
385             390             395                 400

Arg Ala Val Ile Thr Lys Asp Phe Lys Tyr Ile Val Tyr Asp Lys Gly
                405             410                 415

Glu Ile Arg Glu Gln Leu Phe Asp Leu Glu Lys Asp Ala Gly Glu Met
            420             425                 430

Asp Asn Leu Ala Val Lys Pro Ala Tyr Lys Lys Lys Leu Asn Glu Met
        435             440                 445

Arg Ala Tyr Leu Lys Leu Trp Cys Lys Gln His Gln Asp Ser Phe Tyr
    450             455                 460

Ala Leu Lys Lys
465
```